United States Patent [19]

Stapley et al.

[11] 4,017,487

[45] Apr. 12, 1977

[54] 7β-(D-5-AMINO-5-CARBOXYVALERAMIDO)-7-METHOXY-3-SUBSTITUTED-3-CEPHEM-4-CARBOXYLIC ACID ANTIBIOTICS

[75] Inventors: Edward O. Stapley, Metuchen, N.J.; Justo M. Mata, Madrid, Spain

[73] Assignee: Merck & Co., Inc., Rahway, N.J.

[22] Filed: Oct. 4, 1974

[21] Appl. No.: 512,837

Related U.S. Application Data

[60] Division of Ser. No. 203,896, Dec. 1, 1973, abandoned, and a continuation-in-part of Ser. No. 19,496, March 13, 1970, abandoned, Ser. No. 51,319, June 30, 1970, abandoned, Ser. No. 96,594, Dec. 9, 1970, and Ser. No. 115,779, Feb. 16, 1971.

[52] U.S. Cl. .............................. 260/243 C; 424/246
[51] Int. Cl.² ........................................ C07D 501/60
[58] Field of Search ................................ 260/243 C

[56] References Cited

UNITED STATES PATENTS 3,728,342  4/1973  Kukulja .................. 260/243 C

*Primary Examiner*—Nicholas S. Rizzo
*Assistant Examiner*—Jose Tovar
*Attorney, Agent, or Firm*—Richard A. Thompson; Julian S. Levitt

[57] ABSTRACT

Disclosed are 7β-(D-5-amino-5-carboxyvaleramido)-7-methoxy-3-cephem-4-carboxylic acids which are substituted in the three position of the "cephem" nucleus by a variety of alkyl, haloalkyl or oxygen, sulfur and nitrogen containing substitutents; and the salts, esters and amide derivatives thereof. Certain of the products are obtained by fermentation and others are obtained by synthetic means. The products exhibit activity against gram-negative and gram-positive bacteria.

2 Claims, No Drawings

7β-(D-5-AMINO-5-CARBOXYVALERAMIDO)-7-METHOXY-3-SUBSTITUTED-3-CEPHEM-4-CARBOXYLIC ACID ANTIBIOTICS

This is a division of application Ser. No. 203,896 filed, Dec. 1, 1973, now abandoned.

This is a Continuation-in-Part of applicant' abandoned Application Ser. No. 19,496, filed Mar. 13, 1970, applicants' abandoned Application Serial No. 51,319, filed June 30, 1970, applicants' abandoned Application Serial No. 96,594, filed Dec. 9, 1970, and applicants' copending Application Serial No. 115,779, filed Feb. 16, 1971.

This invention relates to a new class of antibiotic substances and to a method for their preparation. Specifically, these new antibiotics are cephalosporin-type products which contain a methoxy substituent at position 7 of the "cephem" nucleus. They are structurally related to the cephalosporin series of compounds but, unlike cephalosporin C which contains only a D-5-amino-5-carboxyvaleramido moiety at position 7, the instant products also contain a 7-methoxy substituent; and, whereas cephalosporin C is substituted by acetoxymethyl at position 3 of the ring, the products of this invention may contain, in addition to acetoxymethyl, a wide variety of other substituents. Illustrative of these substituents are, for example, methyl, halomethyl, hydroxymethyl, an acyloxymethyl moiety of the aliphatic, acyclic and aromatic variety, carbanoyloxymethyl, N-substituted and N,N-disubstituted carbamoyloxymethyl, alkylthiomethyl, heterocyclic substituted thiomethyl, trialkylammoniummethyl, pyridiniummethyl, nuclear substituted pyridiniummethyl, thiouroniummethyl, amidinothiomethyl in which the two nitrogen atoms may be substituted by from one to three alkyl radicals, aminothiocarbonylthiomethyl, N-substituted aminothiocarbonylthiomethyl, aroylthiomethyl, oxythiocarbonylthiomethyl, alkarylsulfonylmethyl, azidomethyl, aminomethyl, amidomethyl, polyhydroxybenzyl, N-lower alkyl-indo-3-ylmethyl and thiocyanatomethyl. These products can be depicted as follows:

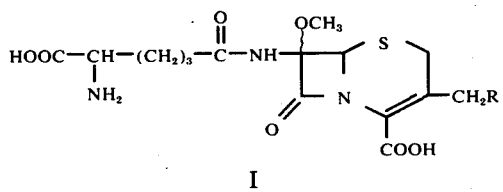

I wherein R is hydrogen, halo, for example, chloro, bromo, fluoro or iodo and the like, hydroxy, acyloxy, for example, lower alkanoyloxy such as acetoxy, n-propionyloxy and the like, mono-nuclear and bi-nuclear aromatic-carbonyloxy, for example, benzoyloxy, naphthoyloxy and the like, heterocyclic-carbonyloxy wherein the heterocycle is a six-membered nitrogen-containing heterocycle such as 4-pyridyl and the like, aralkanoyloxy such as phenacetyloxy, 3-phenylpropionyloxy, 2-naphthylacetoxy or hydrocinnamoyloxy and the like, cycloalkane carbonyloxy containing from 5–6 nuclear carbons, for example, cyclopentanecarbonyloxy or cyclohexanecarbonyloxy and the like, α-methoxy-p-sulfooxycinnamoyloxy or 6θ-methoxy-p-hydroxycinnamoyloxy and the like; a carbamoyloxy radical of the formula: —OOCNR¹R² wherein R¹ and R² are hydrogen, lower alkyl, for example, methyl, ethyl, n-propyl, tertiary-butyl and the like, halo lower alkyl such as chloromethyl, 2-chloroethyl or chlorotertiarybutyl and the like, lower alkoxycarbonyl such as ethoxycarbonyl and the like, aryl, for example, mononuclear and bi-nuclear aryl such as phenyl, naphthyl, and the like, alkarysulfonyl, for example, mono-nuclear alkarylsulfonyl such as p-tolylsulfonyl and the like and benzhydryl or, taken together with the nitrogen atom to which they are attached, R¹ and R² may be joined to form a mononuclear heterocycle such as pyrrolidinyl, piperidino or morpholino; a thio radical of the formula: —SR³ wherein R³ is lower alkyl such as methyl, ethyl, n-propyl and the like, a nitrogen-containing heterocycle as, for example, pyridyl such as 2-, 3- or 4-pyridyl, a lower alkyl substituted thiazolyl such as 4-methylthiazol-2-yl or 4-ethylthiazol-2-yl and the like, 1,3,4-thiadiazol-2-yl, a lower alkyl substituted 1,3,4-thiadiazol-2-yl such as 5-methyl-1,3,4-thiadiazol-2-yl and the like, 2-benzothiazolyl, a 4-lower alkyl-pyrimidinyl such as 4-methylpyrimidin-2-yl; an ammonium radical, for example, a tri-lower alkyl ammonium such as trimethylammonium or triethylammonium and the like or a pyridinium of the formula:

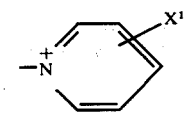

wherein X¹ is hydrogen, halogen, trifluoromethyl, cyano, carboxy, carbamoyl, N-lower alkyl and N,N-di-lower alkyl substituted carbamoyl such as N-methyl carbamoyl, N-ethyl carbamoyl, N,N-dimethylcarbamoyl, N,N-diethylcarbamoyl or N,N-di-isopropylcarbamoyl, carboxymethyl, lower alkanoyl such as acetyl or propionyl and the like, lower alkyl such as methyl, ethyl or n-propyl and the like, hydroxymethyl or sulfo, i.e., —SO₂(OH); a thiouronium radical of the formula:

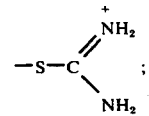

an amidinothio radical of the formula:

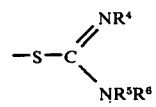

wherein R⁴, R⁵ and R⁶ are the same or different members selected from hydrogen or lower alkyl such as methyl, ethyl, n-propyl and the like; an aminothiocarbonylthio radical of the formula:

wherein R⁷ and R⁸ are the same or different members selected from hydrogen, lower alkyl such as methyl, ethyl, n-propyl and the like, hydroxy-lower alkyl such as 2-hydroxyethyl and the like, di-lower alkylamino-lower alkyl such as 2-(dimethylamino)ethyl, 2-(diethylamino)ethyl, 2-(di-n-propylamino)ethyl, or 3-(diethylamino)propyl and the like, morpholino substituted lower alkyl such as 2-morpholinoethyl and the like, N-aryl-N-lower alkylaminoalkyl such as 2-(N-phenyl-N-methylamino)ethyl or, taken together, the $R^7$ and $R^8$ radicals may be joined with the nitrogen atom to which they are attached to form morpholino, piperidino, pyrwhich two distinct products have been isolated and identified. These two products are characterized by the presence of an α-methoxy-p-sulfooxycinnamoyloxy or an α-methoxy-p-hydroxycinnamoyloxy moiety at position 3 of the cephem nucleus and correspond to the following planar formula:

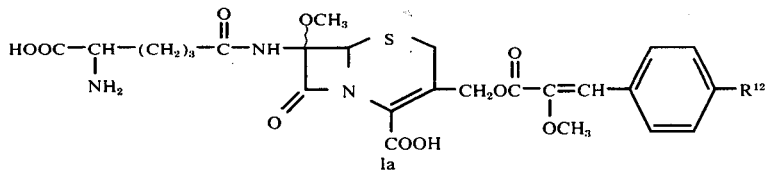

Ia rolidinyl or a piperazino radical of the formula:

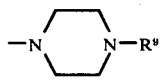

wherein $R^9$ is alkyl, such as methyl, ethyl, n-propyl, isopropyl, n-butyl, amyl, n-octyl, decyl and the like or phenyl; aroythio, for example, a mononuclear aroylthio such as benzoylthio; an oxythiocarbonylthio radical of the formula:

wherein $R^{10}$ is lower alkyl such as ethyl, n-propyl, isopropyl, n-butyl, n-hexyl and the like or lower cycloalkyl, i.e., a cycloalkyl containing from 5 to 6 nuclear carbon atoms such as cyclopentyl and cyclohexyl; alkarylsulfonyl, for example, a mononuclear alkarylsulfonyl such as p-tolylsulfonyl and the like; azido; amino, an amido radical of the formula:

wherein $R^{11}$ is an acyl radical as, for example, lower alkanoyl such as acetyl or propionyl or aralkanoyl as, for example, a mononuclear aralkanoyl such as 2-phenylacetyl and the like; polyhydroxyphenyl, for example, dihydroxyphenyl such as 2,4-dihydroxyphenyl or an N-lower alkyl indol-3-yl such as N-methylindol-3-yl and the like; thiocyanato or, taken together with the nuclear carbons to which they are attached, the R moiety and 3-carboxy radical may be joined to form a lactone ring. Also, included are pharmacologically acceptable salts, esters and amines of the instant products. These include organic and inorganic salts as, for example, acid addition salts, metal salts, quaternary salts and amine salts derived from tertiary organic nitrogen-containing bases. Suitable ester and amide derivatives include the mono- and di-esters such as are derived from alkanols, cycloalkanols, aromatic alcohols and aralkanols and mono- and di-amides such as are derived from ammonia, lower alkylamines, di-lower alkylamines, aralkylamines and heterocyclic amines. Examples of these derivatives and the methods for their preparation can be found in the sub-section entitled Synthetic Methods.

Antibiotic 810A: Essentially, the products of Formula I, supra, comprise two groups of fermentation products. One of these is a mixture of compounds from wherein $R^{12}$ is hydroxy or sulfooxy, i.e., —OSO$_3$H. These products are co-produced by cultivating under controlled conditions a new strain of actinomycete designated as MA-2837 in the culture collection of Merck & Co., Inc., Rahway, N.J. A sample of this culture has also been placed on permanent deposit with the culture collection of the Northern Utilization Research and Development Branch of the U.S. Department of Agriculture at Peoria, Ill., and has been assigned the culture number NRRL 3851. Twenty-five other cultures have also been identified as producers of this antibiotic mixture (Ia) and these, together with culture MA-2837, are described infra in the section entitled The Microorganism. Hereinafter the antibiotic mixture (Ia) comprising these two products will be referred to as Antibiotic 810A or simply, 810A.

Antibiotic 842A: The second group of fermentation products comprises 7β-(D-5-amino-5-carboxyvaleramido)-3-(carbamoyloxymethyl)-7-methoxy-3-cephem-4-carboxylic acid (Ib, infra) and its salts. This compound has the following planar formula:

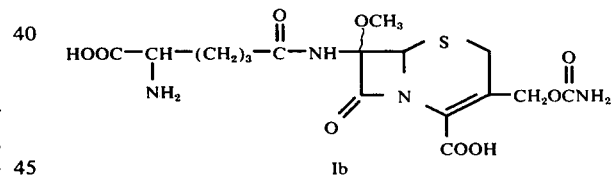

Ib

This product (Ib) is also produced by a new strain of actinomycete and a sample of this microorganism, designated as MA-2908, has been placed in the culture collection of Merck & Co., Inc., Rahway, N.J. A sample of this culture has also been placed on permanent deposit with the culture collection of the Northern Utilization Research and Development Branch of the U.S. Department of Agriculture at Peoria, Ill. This culture has been assigned the culture number NRRL 3802. In addition to its antibiotic activity this product (Ib) is also an intermediate in the preparation of the corresponding 3-hydroxy, 3-acyloxy and carbamoyloxy derivatives. This method for the preparation of these derivatives is described in the subsection entitled Synthetic Methods. Hereinafter, in this specification, the product Ib, i.e., 7β-(D-5-amino-5-carboxyvaleramido)-3-(carbamoyloxymethyl)-7-methoxy-3-cephem-4-carboxylic acid, will be referred to as Antibiotic 842A or, simply, 842A.

ACTIVITY

One major difficulty in antimicrobial therapy is the susceptibility of most antibiotics to enzymatic degradation. Penicillin G, for example, is effective against a wide variety of gram-positive and gram-negative microorganisms but in the presence of penicillinase it is degraded to a form which is ineffective against most pathogens.

One approach to this problem has been the development of new antibiotics which contain the cephem nucleus characteristic of cephalosporin C. Cephalosporin C possesses an inherent resistance to penicillinase and is active against both gram-negative and gram-positive bacteria; however, it is only moderately active and there exist enzymes other than penicillinase which are effective in destroying its activity. These enzymes are designated as cephalosporinases. The products (I) of this invention demonstrate resistance not only to penicillinase but to the cephalosporinases as well. They exhibit against activity both gram-negative and gram-positive bacteria but the order of activity and the range of organisms against which they are effective is not identical.

Antibiotic 842A is characterized by an enhanced activity against gram-negative microorganisms. Unlike cepahlosporin C which has a relatively low antibacterial activity, this product exhibits a significant in vivo gram-negative effect with a potency which, in general, is greater than cephalothin. This activity includes effectiveness in vivo on *Proteus morganii* and an effectiveness against the following gram-negative bacteria: *Escherichia coli, Proteus vulgaris, Proteus mirabilis, Proteus morganii, Salmonella schottmuelleri, Klebsiella pneumoniae AD, Klebsiella pneumoniae B,* and *Paracolobactrum arizonae.*

Antibiotic 842A constitutes a preferred embodiment of this invention. In addition to a generally increased gram-negative effect and an increased potency when compared to cephalothin and a greater resistance to cephalosporinases, 842A is characterized by a low order of toxicity and appears rapidly in the blood. Within four hours after administration approximately 80% is eliminated in the urine. In addition it is more resistant to enzymatic degradation than cephalosporin C and resistance to it develops slowly and it is bactericidal. Given orally it protects against infections due to *Paracolobactrum arizonae* 3720, *Proteus vulgaris* 1810, and *Salmonella schottmuelleri* 3010; and when administered subcutaneously, it is from two to ten times more effective than cephalothin against the same infections.

Antibiotic 810A is a broad spectrum agent which exhibits an approximately balanced gram-negative and gram-positive effect. This includes activity in vivo against the following gram-negative organisms: *Proteus vulgaris, Proteus mirabilis, Salmonella pullorum, Escherichia coli,* and *Klebsiella pneumoniae* and in vivo activity against the following gram-positive organisms: *Staphylococcus aureus, Streptococcus pyogenes* and *Diplococcus pneumoniae.*

Of the several products comprising the Antibiotic 810A, the 7β-(D-5-amino-5-carboxyvaleramido)-3-(α- methoxy-p-sulfooxycinnamoyloxymethyl)-7-methoxy-3-cephem-4-carboxylic acid species, corresponding to Formula Ia, supra, wherein R is sulfooxy, and the salts thereof such as the sodium salt, constitutes a preferred embodiment of this invention. This product has the following planar formula:

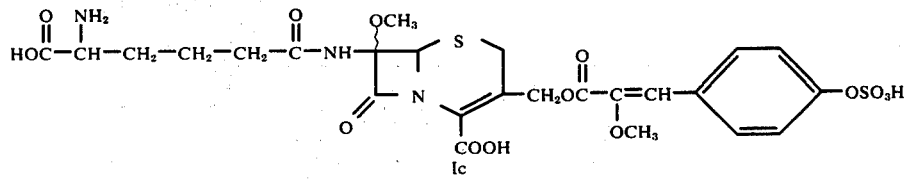

Ic

This compound has a greater resistance to cephalosporinases than cephalothin and is characterized by a low order of toxicity in mice. In addition it is more resistant to enzymatic degradation than cephalosporin C and it is bactericidal. Given orally it protects against infections due to *Proteus vulgaris* and, when administered intraperitoneally, it is effective against a variety of gram-negative and gram-positive infections.

THE MICROORGANISMS

810A Cultures: The microorganism which produces Antibiotic 810A was originally isolated as a single colony from soil. This colony was passed onto a streak plate of the following composition:

| Medium A: | |
|---|---|
| Yeast Extract | 10.0 g. |
| Dextrose | 10.0 g. |
| Agar | 20.0 g. |
| Distilled Water | 1000.0 ml. |

After several days of growth the microorganism produced the Antibiotic 810A. This antibiotic was then reproduced in shake flasks and differentiated from known antibiotics on the basis of various biological and chemical studies. Comparison of this data with that obtained via other known antibiotics established 810A as a new entity.

810A Taxonomy and Morphology: The microorganism (Culture MA-2837) which produces Antibiotic 810A has been identified as *Streptomyces griseus*. The taxonomy employed in this determination if described in "Bergley's Manual of Determinative Bacteriology," Seventh Edition; and in "The Actinomycetes", Vol. 2, by S. A. Waksman (1961). Using that procedure the culture was found to be a strain of *Streptomyces griseus* which closely resembles Streptomyces griseinus in description, melanin production and carbon utilization as described in Waksman and in the "International Journal of Systematic Bacteriology," Vol. 18: page 236 (1968). However, in both Waksman and in the International Journal of Systematic Bacteriology, *Streptomyces griseinus* is narrowly defined as the "grisein-producing strain of *Streptomyces griseus*" or as "producing grisein or grisein-like substances". *Streptomyces griseus* (MA-2837) is a strain that differs from the classic description in Bergey and in Waksman inasmuch as it possesses an aerial mycelium which is predominantly tannish yellow and greenish yellow on some media and with a slightly different carbon utilization pattern. Waksman, on pages 111 and 133 of "The Actinomycetes" describes that *Streptomyces griseus* series as one which encompasses many related species and strains, as characterized by colorless to olive-buff substrate growth, aerial mycelium that is yellowish with a greenish tint, or greenish-grey or sear or grass-green to grey, melanin negative, sphorophores straight or flexuous and produced in tufts, spores oval. The following Tables compare the characteristics of the culture which produces Antibiotic 810A and the *Streptomyces griseus* and *Streptomyces griseinus* cultures.

The characterization of the parent isolate MA-2837 as compared with *Streptomyces griseus* described in Bergey[1] and Waksman[2] and, also, the characterization of MA-2837 as compared with *Streptomyces griseinus* as described in Waksman[2], are set forth in Tables I and Ia, infra.

TABLE I

COMPARISON OF CULTURAL CHARACTERISTICS OF MA-2837 CULTURE

| MA-2837 | Streptomyces griseus (Bergey[1]) | Streptomyces griseus (Waksman[2]) | Streptomyces griseinus (Waksman[2]) |
|---|---|---|---|
| Sporophores are monopodially branched forming tufts, with spore chains straight to slightly flexuous. Spores are spherical to oval, $0.9\mu$ in diameter to $0.9 \times 1.2\mu$, in chains of approximately 10–15 spores. Vegetative hyphae $0.9\mu$ in width (Glycerol-asparagine agar-970X). | Aerial mycelium: Abundant, powdery, water green. Sporophores produced in tufts. Spores spherical to ellipsoidal, 0.8 by 0.8 to 1.7 microns. Vegetative growth: Colonies smooth or folded, colorless, later turning olive-buff. | Sporophores straight produced in tufts. Spores spherical to oval, 0.8 by 0.8 to $1.7\mu$; surface smooth. | Straight sporophores produced in clusters or tufts, without spirals. Spores rod-shaped, 1.0 to 1.8 by 0.8 to $1.0\mu$. |

[1]Bergey's "Manual of Determinative Bacteriology", Seventh Edition (1957).
[2]Waksman, S. A., "The Actinomycetes", Vol. 2 (1961).

TABLE Ia

COMPARISON OF CULTURAL CHARACTERISTICS OF MA-2837 CULTURE

| Medium | MA-2837 | S. griseus (Bergey) | S. griseus (Waksman) | S. griseinus (Waksman) |
|---|---|---|---|---|
| Tomato paste-oatmeal Agar | Vegetative Growth: Reverse-brown, flat, spreading<br>Aerial Mycelium: Center-tan to grayish-yellow; edge-tannish yellow<br>Soluble Pigment: Tan | | | |
| Glycerol-asparagine Agar | Vegetative Growth: Reverse-tan, flat, spreading<br>Aerial Mycelium: Powdery, tannish-yellow<br>Soluble Pigment: Light, tannish yellow | | | |
| Czapek-Dox Agar (Sucrose nitrate agar) | Vegetative Growth: Reverse-yellowish orange, flat, spreading<br>Aerial Mycelium: Powdery, tannish-yellow (several shades but predominantly tannish-yellow); growth light in center and heavier on edges<br>Soluble Pigment: Light, tannish yellow | | Growth thin, spreading, colorless, becoming olive-buff. Aerial mycelium thick, powdery, water green, pigment insoluble. | Substrate growth wrinkled, reverse cream-colored to brownish. Aerial mycelium white to cream-colored with light greenish tinge. No soluble pigment |
| Egg Albumin agar | Vegetative Growth: Reverse-grayish tan, flat, spreading<br>Aerial Mycelium: Tan-yellow with greenish cast, edge tannish yellow, light growth in center, heavier along edges.<br>Soluble Pigment: light tannish yellow | | | |
| Nutrient Agar | Vegetative Growth: Reverse-brownish yellow<br>Aerial Mycelium: Velvety, tannish yellow, edge tannish yellow<br>Soluble Pigment: Light brown | | Growth abundant, almost transparent, cream-colored. Aerial mycelium powdery, white to light grey. No soluble pigment. | |
| Agar | | Abundant, cream-colored almost transparent growth, aerial mycelium powdery, white to light grey. No soluble pigment. | | |
| Synthetic Agar | | Thin, spreading, colorless growth becoming olive-buff Aerial mycelium | | |

TABLE Ia-continued
COMPARISON OF CULTURAL CHARACTERISTICS OF MA-2837 CULTURE

| Medium | MA-2837 | S. griseus (Bergey) | S. griseus (Waksman) | S. griseinus (Waksman) |
|---|---|---|---|---|
| | | thick, powdery, water-green. | | |
| Gelatin Stab | Flaky cream-colored growth settling in bottom of tube. Complete liquefaction. | | Greenish yellow or cream-colored surface growth with brownish tinge. Rapd liquefaction. | Growth cream-colored with brownish tinge. Aerial mycelium absent or scant, white. Rapid liquefaction. |
| Nutrient Gelatin Agar | Vegetative Growth: Cream Aerial Mycelium: Pale, tannish yellow Soluble Pigment: None Liquefaction of gelatin-good. | | | |
| Litmus Milk | Partial ring Vegetative Growth: Brownish Aerial Mycelium: Slight, whitish Peptonization, becoming alkaline | | Cream-colored ring; coagulation with rapid peptoniaztion, becoming alkaline. | Growth cream-colored. Coagulation and peptonization. |
| Skim Milk | Partial ring Vegetative Growth: Brownish Aerial Mycelium: None Soluble Pigment: Light brown Peptonization, becoming alkaline | | | |
| Skim Milk Agar | Vegetative Growth: Cream, flat, spreading Aerial Mycelium: Sparse, yellowish white to cream Soluble Pigment: Very light brown Hydrolysis of casein | | | |
| Glucose Agar | | | Growth elevated in center, radiate, cream-colored to orange, erose margin | |
| Glucose Broth | | Abundant, yellowish pellicle with greenish tinge, much folded | | |
| Starch Agar | | Thin, spreading transparent growth Starch is hydrolyzed. | Growth thin, spreading, transparent, hydrolysis strong | Colorless to cream-colored growth Aerial mycelium grayish-olive. Hydrolysis rapid |
| Nutrient Starch Agar | Vegetative Growth: Cream Aerial Mycelium: Pale tannish yellow Soluble Pigment: None Hydrolysis good | | | |
| Potato Plug | Vegetative Growth: Light brown Aerial Mycelium: Moderate, tan Slight browning of potato. | Yellowish, wrinkled growth covered with white, powdery aerial mycelium. | Growth wrinkled, yellowish to brownish, covered with white, powdery aerial mycelium. | Growth wrinkled, yellowish-white. Aerial mycelium grayish white with olive tinge. |
| Calcium Malate Agar | Vegetative Growth: Flat, spreading, translucent and colorless at edges, opaque and cream-colored in center. Aerial Mycelium: Moderate, cream to yellow, edges tannish yellow Soluble Pigment: None | | Green or yellow soluble pigment produced on calcium malate and succinate media. | No soluble pigments on calcium malate or succinate media |
| Nutrient Tyrosine Agar | Vegetative Growth: Flat spreading, cream-colored Aerial Mycelium: Yellowish tan with greenish cast, edges tannish yellow Soluble Pigment: Very light brown Tyrosine crystals decomposed. | | Dark pigment often produced | No pigment produced |
| Peptone-iron-yeast Extract Agar | Vegetative Growth: Cream-colored Aerial Mycelium: None Soluble Pigment: None Melanin negative | | | |
| Production of H$_2$S | Negative | | Negative | Negative |
| Loeffler's Blood Serum Slants | Vegetative Growth: Tan Aerial Mycelium: Slight, yellowish | | | |

TABLE Ia-continued
COMPARISON OF CULTURAL CHARACTERISTICS OF MA-2837 CULTURE

| Medium | MA-2837 | S. griseus (Bergey) | S. griseus (Waksman) | S. griseinus (Waksman) |
|---|---|---|---|---|
| | Soluble Pigment: Brownish | | | |
| | Complete liquefaction. | | | |
| Temperature Range (yeast extract-dextrose-salts agar slants) | 28° C - good growth<br>37° C - good growth<br>50° C - no growth | Optimum temperature 37° C. | | |
| Microaerophilic Growth (yeast extract-dextrose-salts stab-40 mm depth) | Good growth covering surface and along entire stab line. | Aerobic | | |
| Reduction of nitrates to nitrites | Negative | Positive | Positive | Positive |

These observations were made after three weeks incubation at 28° C. except where otherwise noted. The pH of the media used in these studies was approximately neutral, that is, 6.8 to 7.2. The physiological tests were run at the end of seven and twenty-two days. The colors used in the description are in accordance with the definitions of the "Color Harmony Manual," Fourth Edition, 1958; Container Corporation of America.

810A Carbohydrate Utilization:

The *Streptomyces griseus* culture (MA-2837) was also tested for its ability to utilize or assimilate various carbohydrates by growing the microorganism in basal synthetic medium (T. G. Pridham and D. Gottlieb, Journal of Bacteriology, Vol. 56: page 107 (1948) containing 1% of the carbohydrate at 28° C. for three weeks. Table II infra, indicates the utilization or assimilation of these carbohydrate sources by the *Streptomyces griseus* culture (MA-2837). The explanation of the symbols in Table II are as follows: + indicates good growth, ± indicates poor growth, and − indicates no growth on the particular carbohydrate.

TABLE II

| Carbohydrate | MA-2837 Culture | Carbohydrate | MA-2837 Culture |
|---|---|---|---|
| Glucose | + | Lactose | + |
| Arabinose | + | Inositol | ± |
| Xylose | + | Sucrose | ± |
| Maltose | + | Rhamnose | ± |
| Mannose | + | Raffinose | ± |
| Fructose | − | Cellulose | − |
| Mannitol | + | | |

The characteristics described in Tables I, Ia and II were used to reduce the *Streptomyces griseus* culture (MA-2837) to a species classification via the keys described in "Bergey's Manual of Determinative Bacteriology," Seventh Edition, pages 694–829 (1959) and in "The Actinomycetes," Vol. 2: pages 61–292 (1961). A comparison of the culture (MA-2837) with known species shows that it is similar to *Streptomyces griseus*. There are morphological differences as, for example, in the color of the aerial mycelium which, in *Streptomyces griseus*, is predominantly tannish yellow and greenish yellow but, in view of the significant number of similarities and the only minor differences there is no justification for a new species name. As a result, the microorganism (MA-2837) which produces Antibiotic 810A has been identified as a strain of *Streptomyces griseus*.

In addition to the foregoing culture (MA-2837), 25 additional cultures have been identified as producers of the Antibiotic 810A. These include: three cultures of *Streptomyces griseus*, eleven cultures of *Streptomyces viridochromogenes*, five cultures of *Streptomyces fimbriatus*, three cultures of *Streptomyces halstedii*, one culture of *Streptomyces rochei*, one culture of *Streptomyces cinnamonensis* and one culture of *Streptomyces chartreusis*. These strains of *Streptomyces* are identified as cultures MA-4160, MA-4174, MA-4171, MA-4177, MA-4178, MA-4180, MA-4164, MA-4165, MA-4166, MA-4167, MA-2892, MA-3265, MA-4162, MA-4163, MA-4159, MA-4169, MA-4170, MA-4179, MA4161, MA-4168, MA-4175, MA-4181, MA-2938, MA-4176 and MA-4173 in the culture collection of Merck & Co., Inc., Rahway, N.J. These cultures have been placed on permanent deposit with the culture collection of the Northern Utilization Research and Development Branch of the U.S. Department of Agriculture at Peoria, Ill.

The assigned NRRL culture numbers are as follows:

| | |
|---|---|
| *Streptomyces griseus:* | |
| MA-4160 | NRRL 3951 |
| MA-4174 | NRRL 3953 |
| MA-4171 | NRRL 3952 |
| *Streptomyces viridochromogenes:* | |
| MA-4177 | NRRL 3970 |
| MA-4178 | NRRL 3971 |
| MA-4180 | NRRL 3972 |
| MA-4164 | NRRL 3966 |
| MA-4165 | NRRL 3967 |
| MA-4166 | NRRL 3968 |
| MA-4167 | NRRL 3969 |
| MA-2892 | NRRL 3962 |
| MA-3265 | NRRL 3963 |
| MA-4162 | NRRL 3964 |
| MA-4163 | NRRL 3965 |
| *Streptomyces fimbriatus:* | |
| MA-4159 | NRRL 3954 |
| MA-4169 | NRRL 3956 |
| MA-4170 | NRRL 3957 |
| MA-4179 | NRRL 3958 |
| MA-4161 | NRRL 3955 |
| *Streptomyces halstedii:* | |
| MA-4168 | NRRL 3959 |
| MA-4175 | NRRL 3960 |
| MA-4181 | NRRL 3961 |
| *Streptomyces rochei:* | |
| MA-2938 | NRRL 3973 |
| *Streptomyces cinnamonensis:* | |
| MA-4176 | NRRL 3974 |
| *Streptomyces chartreusis:* | |
| MA-4173 | NRRL 3975 |

The characterization of the aforementioned isolates for comparison with *Streptomyces griseus*, *Streptomyces viridochromogenes*, *Streptomyces fimbriatus*,

*Streptomyces halstedii, Streptomyces rochei, Streptomyces cinnamonensis* and *Streptomyces chartreusis* are set forth below in Tables IIa–IIe.

TABLE IIa

CULTURAL CHARACTERISTICS OF STRAINS OF
*STREPTOMYCES GRISEUS* PRODUCING ANTIBIOTIC 810A

| Medium | MA-4160 | MA-4174 | MA-4171 |
|---|---|---|---|
| Morphology | Sporophores form tufts with spore chains straight to slightly flexuous. Spores are spherical to oval - $0.9\mu$ dia. to $0.9\mu \times 1.2\mu$ - in chains of approximately 10–15 spores. | | |
| Tomato Paste - Oatmeal Agar | Vegetative Growth: Good, flat, spreading tan | | |
| | Aerial Mycelium: Powdery; tan with greenish cast | Aerial Mycelium: Powdery; tan with strong green overtone | Aerial Mycelium: Powdery; tan with strong green overtone |
| | Soluble Pigment: Light brown | | |
| Glycerol-asparagine Agar | Vegetative Growth: Good, flat, tan | | |
| | Aerial Mycelium: Powdery, tan with greenish cast and vectors of gray-green | | |
| | Soluble Pigment: Light brown | | |
| Czapek-Dox Agar | Vegetative Growth: Flat, spreading transparent | | |
| | Aerial Mycelium: Moderate; tan | Aerial Mycelium: Moderate; tan | Aerial Mycelium: Moderate; grayish |
| | Soluble Pigment: Light brown | Soluble Pigment: Light brown | Soluble Pigment: None |
| Yeast Extract - Dextrose + Salts Agar | Vegetative Growth: Flat, spreading, tan | | |
| | Aerial Mycelium: Good; powdery, beige | | |
| | Soluble Pigment: Light brown | | |
| Soluble Pigment on Peptone-Iron-Yeast Extract Agar | None | None | None |

TABLE IIb

CULTURAL CHARACTERISTICS OF STRAINS OF
*STREPTOMYCES VIRIDOCHROMOGENES* PRODUCING ANTIBIOTIC 810A

| Medium | MA-2892 | MA-3265 | MA-4162 | MA-4163 |
|---|---|---|---|---|
| Morphology | Sporophores are short, compact spirals occurring as side branches on aerial hyphae. Spores are spherical to oval - 0.9 to $1.2\mu$ diameter and $0.9 - 1.2 \times 1.2 - 1.7\mu$ - in chains of approximately 10–15 spores. | | | |
| Tomato Paste-Oatmeal Agar | Vegetative Growth: Reverse brown | Vegetative Growth: Reverse tan | Vegetative Growth: Reverse dark brown | Vegetative Growth: Reverse brown |
| | Aerial Mycelium: Velvety; dark gray & white | Aerial Mycelium: Velvety; light gray & white | Aerial Mycelium: Velvety; bluish-gray & white | Aerial Mycelium: Velvety; medium gray & white |
| | Soluble Pigment: Light brown | Soluble Pigment: None | Soluble Pigment: Light brown | Soluble Pigment: Light brown |
| Glycerol-aspara-gine Agar | Vegetative Growth: Reverse dark brown | Vegetative Growth: Reverse dark brown | Vegetative Growth: Reverse dark brown | Vegetative Growth: Reverse brown |
| Aerial Mycelium: | Aerial Mycelium: Dark gray and cream | Aerial Mycelium: Light gray | Aerial Mycelium: Cream & Light gray | Cream & gray |
| | Soluble Pigment: Light brown | Soluble Pigment: None | Soluble Pigment: Light brown | Soluble Pigment: Light brown |
| Czapek-Dox Agar | Vegetative Growth: Dark brown | Vegetative Growth: Dark brown | Vegetative Growth: Dark brown | Vegetative Growth: tan |
| | Aerial Mycelium: Very scant | Aerial Mycelium: Light gray & white | Aerial Mycelium: Very scant | Aerial Mycelium: Very scant |
| | Soluble Pigment: Dark brown | Soluble Pigment: Light brown | Soluble Pigment: Light brown | Soluble Pigment: Light brown |
| Yeast Extract-Dextrose Agar | Vegetative Growth: Dark brown | Vegetative Growth: Reverse brown | Vegetative Growth: Dark brown | Vegetative Growth: Dark brown |
| | Aerial Mycelium: Very scant | Aerial Mycelium: Light gray | Aerial Mycelium: Very scant | Aerial Mycelium: Very scant |
| | Soluble Pigment: Light brown | Soluble Pigment: None | Soluble Pigment: Light brown | Soluble Pigment: Light brown |
| Soluble Pigment on Peptone-Iron-Yeast Extract Agar | Dark brown | | | |
| Medium | MA-4164 | MA-4165 | MA-4166 | MA-4167 |
| Morphology | Sporophores are short, compact spirals occurring as side branches on aerial hyphae. Spores are spherical to oval - 0.9 to 1.2 diameter and $0.0 - 1.2 \times 1.2 - 1.7$ - in chains of approximately 10–15 spores. | | | |
| Tomato Paste-Oatmeal Agar | Vegetative Growth: Reverse dark brown | | | |
| | Aerial Mycelium: Velvety; blue-gray & cream | Aerial Mycelium: Velvety; medium gray & cream | Aerial Mycelium: Velvety; medium gray & cream | Aerial Mycelium: Velvety; dark gray & cream |
| | Soluble Pigment: Light brown | | | |
| Glycerol-aspara-gine Agar | Vegetative Growth: Reverse dark brown | Vegetative Growth: Reverse dark brown | Vegetative Growth: Dark gray | Vegetative Growth: Reverse tan |
| | Aerial Mycelium: | Aerial Mycelium: | Aerial Mycelium: | Aerial Mycelium: |

TABLE IIb-continued
CULTURAL CHARACTERISTICS OF STRAINS OF *STREPTOMYCES VIRIDOCHROMOGENES* PRODUCING ANTIBIOTIC 810A

|  |  |  |  |  |
|---|---|---|---|---|
|  | Dark gray & cream | Medium gray & cream | Scant-greyish | Light gray & cream |
|  |  | Soluble Pigment: Light brown |  |  |
| Czapek-Dox Agar | Vegetative Growth: Brown | Vegetative Growth: Reverse brown | Vegetative Growth: Brown | Vegetative Growth: Tan |
|  | Aerial Mycelium: Very scant | Aerial Mycelium: Light gray & cream | Aerial Mycelium: Very scant | Aerial Mycelium: Very scant |
|  | Soluble Pigment: Brown | Soluble Pigment: Light brown | Soluble Pigment: Brown | Soluble Pigment: Light brown |
| Yeast Extract-Dextrose Agar |  | Vegetative Growth: Dark brown |  |  |
|  |  | Aerial Mycelium: Very scant |  |  |
|  |  | Soluble Pigment: Light brown |  |  |
| Soluble Pigment on Peptone-Iron-Yeast Extract Agar |  | Dark brown |  |  |

| Medium | MA-4177 | MA-4178 | MA-4180 |
|---|---|---|---|
| Morphology | Sporophores are short, compact spirals occurring as side branches on aerial hyphae. Spores are spherical to oval - 0.9 to 1.2μ diameter and 0.9 – 1.2 × 1.2 – 1.7μ - in chains of approximately 10–15 spores. | | |
| Tomato Paste-Oatmeal Agar | Vegetative Growth: Reverse tan | Vegetative Growth: Reverse brown | Vegetative Growth: Reverse brown |
|  | Aerial Mycelium: Velvety; dark gray & white | Aerial Mycelium: Velvety; dark gray | Aerial Mycelium: Velvety; dark gray & cream |
|  |  | Soluble Pigment: Light brown |  |
| Glycerol-asparagine Agar | Vegetative Growth: Reverse brown | Vegetative Growth: Reverse dark brown | Vegetative Growth: Reverse dark brown |
|  | Aerial Mycelium: Dark gray | Aerial Mycelium: Dark gray | Aerial Mycelium: Mixture of light & dark gray |
|  |  | Soluble Pigment: Light brown |  |
| Czapek-Dox Agar | Vegetative Growth: Tan | Vegetative Growth: Dark brown | Vegetative Growth: Tan |
|  |  | Aerial Mycelium: Very scant |  |
|  |  | Soluble Pigment: Light brown |  |
| Yeast Extract-Dextrose Agar | Vegetative Growth: Dark brown | Vegetative Growth: brown | Vegetative Growth: Brown |
|  | Aerial Mycelium: Scant-grayish | Aerial Mycelium: Very scant | Aerial Mycelium: Very scant |
|  |  | Soluble Pigment: Light brown |  |
| Soluble Pigment on Peptone-Iron-Yeast Extract Agar |  | Dark brown |  |

TABLE IIc
CULTURAL CHARACTERISTICS OF STRAINS OF *STREPTOMYCES FIMBRIATUS* PRODUCING ANTIBIOTIC 810A

| Medium | MA-4159 | MA-4169 | MA-4170 | MA-4179 | MA-4161 |
|---|---|---|---|---|---|
| Morphology | Sporophores are short, compact spirals and some loops, occurring as side branches on aerial hyphae. Spores are spherical to oval - 0.9μ diameter and 0.9 × 1.2μ - chains of approximately 10–15 spores. | | | | Sporophores are short hooks & loops, occurring as side branches on aerial mycelium. Spores are in chains of less than 10 spores - spherical to oval, 0.9μ diameter & 0.9 × 1.2μ |
| Tomato Paste - Oatmeal Agar | Vegetative Growth: Reverse tan | Vegetative Growth: Reverse tan | Vegetative Growth: Reverse tan | Vegetative Growth: Reverse tan | Vegetative Growth: Tan |
|  | Aerial Mycelium: Moderate; light gray | Aerial Mycelium: Moderate; light gray | Aerial Mycelium: Moderate; light gray & cream | Aerial Mycelium: Sparse, grayish | Aerial Mycelium: Scant; grayish |
|  |  |  | Soluble Pigment: Light brown |  |  |
| Glycerol-asparagine Agar | Vegetative Growth: Dark brownish-gray | Vegetative Growth: Dark brownish-gray | Vegetative Growth: Dark brownish-gray | Vegetative Growth: Dark brownish-gray | Vegetative Growth: Reverse tan with reddish tan vector |
| Czapek-Dox Agar | Vegetative Growth: Dark brownish-gray | Vegetative Growth: Dark brownish-gray | Vegetative Growth: Dark brownish-gray | Vegetative Growth: Dark brownish-gray | Vegetative Growth: Tan |
|  | Aerial Mycelium: Very scant | Aerial Mycelium: Moderate; gray | Aerial Mycelium: Moderate; gray | Aerial Mycelium: Very scant | Aerial Mycelium: Very scant |
|  | Soluble Pigment: Brown | Soluble Pigment: Brown | Soluble Pigment: Brown | Soluble Pigment: Brown | Soluble Pigment: Light brown |
| Yeast Extract Dextrose + Salts Agar | Vegetative Growth: Dark brownish-gray | Vegetative Growth: Dark brownish-gray | Vegetative Growth: Dark brownish-gray | Vegetative Growth: Dark brownish-gray | Vegetative Growth: Brown |
|  |  |  | Aerial Mycelium: Very scant |  |  |

TABLE IIc-continued

CULTURAL CHARACTERISTICS OF STRAINS OF *STREPTOMYCES FIMBRIATUS* PRODUCING ANTIBIOTIC 810A

| Medium | MA-4159 | MA-4169 | MA-4170 | MA-4179 | MA-4161 |
|---|---|---|---|---|---|
| Soluble Pigment on Peptone-Iron-Yeast Extract Agar | | | Soluble Pigment: Brown Dark brown | | |

TABLE IId

CULTURAL CHARACTERISTICS OF STRAINS OF *STREPTOMYCES HALSTEDII* PRODUCING ANTIBIOTIC 810A

| Medium | MA-4168 | MA-4175 | MA-4181 |
|---|---|---|---|
| Morphology | Sporophores are long, loose spirals occurring as side branches on aerial hyphae. Spores are spherical to oval - 0.9μ diameter and 0.9 × 1.2μ - in chains of more than 10 spores. | | |
| Tomato Paste-Oatmeal Agar | Vegetative Growth: Reverse brown<br>Aerial Mycelium: Powdery; dark grey | Vegetative Growth: Reverse tan<br>Aerial Mycelium: Dark grey & white; powdery<br>Soluble Pigment: None | Vegatative Growth: Reverse brown<br>Aerial Mycelium: Dark grey & white |
| Glycerol-asparagine Agar | Vegetative Growth: Reverse brown to<br>Aerial Mycelium: Powdery; dark grey and white | Vegetative Growth: Reverse greyish<br>Aerial Mycelium: Powdery, predominantly dark grey mixed with light grey and white<br>Soluble Pigment: None | Vegetative Growth: Reverse greyish<br>Aerial Mycelium: Dark grey; powdery |
| Czapok-Dox Agar | Vegetative Growth: Cream<br><br>Aerial Mycelium: Greyish cream | Vegetative Growth: Reverse reddish brown<br>Aerial Mycelium: Greyish cream<br>Soluble Pigment: None | Vegetative Growth: Cream<br><br>Aerial Mycelium: Very scant |
| Yeast Extract Dextrose + Salts Agar | Vegetative Growth: Tan<br>Aerial Mycelium: Greyish; scant | Vegetative Growth: Tan<br>Aerial Mycelium: Scant; greyish<br>Soluble Pigment: None | Vegetative Growth: Brown<br>Aerial Mycelium: Scant; greyish |
| Soluble Pigment Peptone-Iron-Yeast Extract Agar | | None | |

TABLE IIe

CULTURAL CHARACTERISTICS OF *STREPTOMYCES* SPECIES PRODUCING ANTIBIOTIC 810A

| Medium | MA-2938 | MA-4176 | MA-4173 |
|---|---|---|---|
| | *Streptomyces rochei* | *Streptomyces cinnamonensis* | *Streptomyces chartreusis* |
| Morphology | Sporophores form compact spirals occurring as side chains of approximately 10–15 spores - spherical to oval, 0.9μ diameter & 9 × 1.2μ | Sporophores are hooks, loops, & a few loose spirals, occurring as side branches on aerial hyphae Spores are in chains of more than 10 spores - spherical to oval, 0.9μ diameter & 0.9 × 1.2μ | Sporophores are compact spirals, occurring as side branches on aerial hyphae. spores are in chains of more than 10 spores - spherical to oval, 0.9 – 1.2μ diameter. & 0.9 – 1.2 × 1.2 – 1.7μ |
| Tomato Paste-Oatmeal Agar | Vegetative Growth: Reverse reddish-brown<br><br>Aerial Mycelium: Medium gray<br><br>Soluble Pigment: None | Vegetative Growth: Tan<br><br><br>Aerial Mycelium: Beige with pink tint; velvety<br><br>Soluble Pigment: Brown | Vegetative Growth: Light brown with vectors of orange-brown<br>Aerial Mycelium: Powdery; dark gray with blue-green tint<br>Soluble Pigment: Brown |
| Glycerol-asparagine Agar | Vegetative Growth: Reverse reddish-brown<br><br>Aerial Mycelium: Medium gray<br>Soluble Pigment: None | Vegetative Growth: Revese dark reddish-brown<br>Aerial Mycelium: Beige with pink tint<br>Soluble Pigment: Brown | Vegetative Growth: Brown<br><br><br>Aerial Mycelium: Very scant<br><br>Soluble Pigment: Light brown |
| Czapek-Dox Agar | Vegetative Growth: Reddish brown<br>Aerial Mycelium: Very scant<br><br>Soluble Pigment: None | Vegetative Growth: Reverse dark brown<br>Aerial Mycelium: Moderate; beige with pink tint<br>Soluble Pigment: Brown | Vegetative Growth: Orange-brown<br>Aerial Mycelium: Very scant<br><br>Soluble Pigment: Light brown |
| Yeast Extract Dextrose + Salts | Vegetative Growth: Tan<br>Aerial Mycelium: | Vegetative Growth: Brown<br>Aerial Mycelium: Sparse | Vegetative Growth: Brown<br>Aerial Mycelium: |

TABLE IIe-continued
CULTURAL CHARACTERISTICS OF STREPTOMYCES SPECIES PRODUCING ANTIBIOTIC 810A

| Medium | MA-2938 | MA-4176 | MA-4173 |
| --- | --- | --- | --- |
| Agar | Grayish<br>Soluble Pigment:<br>Light brown | creamish-white<br>Soluble Pigment:<br>Light brown | Very scant<br>Soluble Pigment: Brown |
| Soluble Pigment on Peptone-Iron-Yeast Extract Agar | None | Dark Brown | Dark Brown |

The foregoing description of the microorganisms producing Antibiotic 810A is simply illustrative of the type of strains which can be used and it should be understood that this invention is not limited to an organism meeting these particular descriptions. This invention includes the use of other microorganisms including strains of actinomycetes isolated from nature or obtained by mutation as, for example, those obtained by natural selection or those produced by mutating agents as, for example, X-ray irradiation, ultraviolet irradiation, nitrogen mustards and the like which, under suitable conditions will yield an identical antibiotic.

842A Culture: The microorganism which produces Antibiotic 842A is a previously unknown strain of actinomycete. The original isolate was obtained as a single colony from soil on an agar slant and grown in a medium having the following composition:

| Medium B: | |
| --- | --- |
| Yeast Extract | 10.0 g. |
| Glucose | 10.0 g. |
| *Phosphate Buffer | 2.0 ml. |
| $MgSO_4 \cdot 7H_2O$ | 0.05 g. |
| Distilled Water<br>pH 6.5 | 1000.0 ml. |
| *Phosphate Buffer: | |
| $KH_2PO_4$ | 91.0 g. |
| $Na_2HPO_4$ | 95.0 g. |
| Distilled Water | 1000.0 ml. |

After several days of growth it was found that no sporulation could be detected. The microorganism produced an antibiotic which was differentiated from known antibiotics on the basis of its profile in various biological and chemical studies. Comparison of this data with that obtained via other known antibiotics established 842A as a new entity. 842A Taxonomy: The microorganism (Culture MA-2908) which produces 842A has been identified as a new species of actinomycetes. The taxonomy employed in this determination is described in Bergey's Manual of Determinative Bacteriology, Seventh edition; and in "The Actinomycetes," Vol. 2, "Classication, Identification and Description of Genera and Species," S. A. Waksman (1961). Using that procedure the culture was found to belong to the genus Streptomyces and it possesses many of the attributes of the known species Streptomyces fradiae. Biochemically it is an essentially perfect match with the latter. Morphologically, however, there are important differences. For example, the color of the aerial mycelium of S. fradiae is a seashell pink whereas the culture MA-2908 is usually cream colored. Also, the vegetative growth in the MA-2908 culture shows pigment differences on the various media employed, and, as stated below, no sporulation was detected on standard taxonomic media. On the basis of these differences, the culture was assigned a new species name: Streptomyces lactamdurans. Table III, infra, describes the biochemical attributes of the Streptomyces lactamdurans species and those of the known Streptomyces fradiae. All of the readings in Table III were taken after three weeks incubation at 28° C. except where otherwise noted. The pH of the media used in these studies was approximately neutral, namely, 6.8 to 7.2. The physiological tests were run at the end of seven and twenty-one days.

TABLE III

842A Biochemical Comparison

| Test | Streptomyces lactamdurans | Streptomyces fradiae |
| --- | --- | --- |
| aerial mycelium | straight, some branching | straight branching-filaments |
| conidia | none detected | rod-shaped |
| soluble pigment | none | none |
| optimum temperature | 28° C. | 25° C. |
| invertase | negative | negative |
| reduction of nitrate | negative | negative |
| gelatin liquefaction | positive | positive |
| cellulose utilization | negative | negative |
| litmus milk | alkaline; peptonization | alkaline; peptonization |

842A Morphology:

Sporophores were not detected when the culture was grown on the media listed in the description of culture characteristics even though repeated observations were made up to 8 weeks. However, stained impression slides showed long filaments, many segmented into sub-units of various sizes, generally rod shaped and approximately 0.9 by 1.7 microns in size.

Tomato-Paste-Oatmeal Agar

Vegetative growth — reverse — orange; flat, dry appearing, wrinkled
Aerial Mycelium — sparse, cream
No soluble pigment

Czapek-Dox Agar

Vegetative — flat, deep cream
Aerial Mycellium — powdery, creamish white
No soluble pigment

Glycerol-Asparagine Agar

Vegetative growth — flat, reverse — golden yellow to orange
Aerial Mycelium — powdery, cream with pale peach tones
Soluble pigment — pale amber

Egg Albumin Agar

Vegetative growth — flat, cream to yellow

Aerial Mycellium — powdery, cream
No soluble pigment

Calcium Malate Agar

Vegetative growth — flat, reverse — yellow edged with orange
Aerial Mycelium — powdery, white to cream edged with peach
No soluble pigment

Nutrient Tyrosine Agar

Vegetative growth — flat, tan to orange
Aerial Mycelium — sparse, cream with white
No soluble pigment
Tyrosine crystals decomposed

Molasses — Yeast Hydrolysate Agar

Vegetative growth — flat; reverse — orange
Aerial Mycelium — powdery, creamish white
No soluble pigment

Nutrient Agar

Vegetative growth — flat, golden yellow
Aerial Mycelium — powdery, cream
No soluble pigment

Litmus Milk

Sparse growth ring — tan vegetative growth — no aerial mycelium
Peptonization: alkaline reaction;
pH 7.3 – 7.4 (Control pH — 6.7)

Slim Milk

Sparse growth ring — tan to orange
Vegetative growth — no aerial mycelium
Light tan soluble pigment
Peptonization — alkaline reaction
pH 7.2 (Control pH — 6.6)

Skim Milk Agar

Vegetative growth — flat, orange
Aerial Mycelium — moderate, cream to pale coral
Light tan soluble pigment
Hydrolysis of casein

Gelatin Stab

Sparse cream to orange colored flaky vegetative growth suspended throughout tube
No soluble pigment
Complete liquefaction

Nutrient Gelatin Agar

Vegetative growth — flat, orange
Aerial Mycelium — sparse, powdery, cream
No soluble pigment
Liquefaction of gelatin

Nutrient Starch Agar

Vegetative growth — flat, orange
Aerial Mycelium — sparse, powdery, pinkish cream
No soluble pigment
Moderate hydrolysis of starch

Synthetic Starch Agar

Vegetative growth — flat; reverse — cream edged with orange
Aerial Mycelium — powdery, white edged with peach
No soluble pigment
Moderate hydrolysis of starch

Loeffler's Blood Serum Agar

Vegetative growth — cream colored to orange
Aerial Mycelium — none
No soluble pigment
No liquefaction

Peptone-Iron-Yeast Extract Agar

Vegetative growth — cream
Aerial-sparse-whitish
No soluble pigment

Microaerophilic Growth (Yeast extract-dextrose stab — 40 mm. depth of stab.)
Good surface growth and along upper ¼ of stab line.

Temperature – Yeast extract-dextrose slants

Good growth at 28° C.
Sparse growth at 37° C.
No growth at 50° C.

Yeast Extract — Dextrose Agar

Vegetative growth — flat, golden yellow
Aerial Mycelium — powdery, cream to pale flesh pink
No soluble pigment

Potato plug

Vegetative growth — dry, flat, cream to orange
Aerial Mycelium — sparse, creamish
No soluble pigment
Reduction of Nitrates to Nitrates — Negative All readings were taken after 3 weeks incubation at 28° C. except where noted otherwise. Physiological tests were run at 7 and 21 days.

The morphological differences between *Streptomyces lactamdurans* and *Streptomyces fradiae* are set forth in Table IV, infra. The observations were made on the media indicated in Table IV at growth intervals of one week, three weeks and eight weeks. The aerial mycelium of *S. lactamdurans* is short and straight with little branching. It appears to be about the same size as the vegetative mycelium, i.e., 0.9 micrometer in width. It is light, powdery and scrapes off easily. The vegetative mycelium is gram-positive; it is not acid-fast. It clings to and in some media is imbedded in the agar. There is some fragmentation into rods in shake-flask growth but this is not extensive. Vegetative mycelium from shaker and stationary flasks (seed medium four to six days, 28° C.) showed some "buds" and short, thickened, almost club-shaped segments on mycelium but these were not numerous. All of the readings in Table IV were taken after three weeks incubation at 28° C. except where otherwise noted. The pH of the media used in these studies was approximately neutral, that is, 6.8 to 7.2. The physiological tests were run at the end of seven and twenty-one days. The colors used in the description are in accordance with the definitions of the "Color Harmony Manual," Fourth Edition, 1958; Container Corporation of America.

TABLE IV

842A; Morphological Comparison of *Streptomyces lactamdurans* and *Streptomyces fradiae*

| Medium | *Streptomyces lactamdurans* | | *Streptomyces fradiae* | |
|---|---|---|---|---|
| Czapek-Dox Agar | Vegetative Growth: | Flat, deep cream | Vegetative Growth: | Colorless |
| | Aerial; Mycelium: | Powdery, creamish white | Aerial Mycelium: | Seashell pink |
| | No Soluble Pigment | | | |
| Nutrient Agar | Vegetative Growth: | Flat, cream to golden yellow | Vegetative Growth: | Orange-yellow |
| | Aerial Mycelium: | Powdery, cream | | |
| | No Soluble Pigment | | | |
| Glycerol-Asparagine Agar | Vegetative Growth: | Flat, reverse - golden yellow to orange | Vegetative Growth: | Buff-colored |
| | Aerial Mycelium: | Powdery, cream with pale peach tones | | |
| | Soluble Pigment: | Pale amber | | |
| Yeast Extract - Dextrose Agar | Vegetative Growth: | Flat, golden yellow | Vegetative Growth: | Buff-colored |
| | Aerial Mycelium: | Powdery, cream to pale flesh pink | | |
| | No Soluble Pigment | | | |
| Synthetic Starch Agar | Vegetative Growth: | Flat, reverse - cream edged with orange | Vegetative Growth: | Colorless |
| | Aerial Mycelium: | Powdery, white edged with peach | Aerial Mycelium: | Seashell pink |
| | No Soluble Pigment | | | |
| | Moderate Hydrolysis of Starch | | | |
| Potato Plug | Vegetative Growth: | Dry, flat, cream to orange | Vegetative Growth: | Orange |
| | Aerial Mycelium: | Sparse, creamish | | |
| | No Soluble Pigment | | | |
| Gelatin Stab | Vegetative Growth: | Sparse cream to orange flakes suspended throughout the tube | Vegetative Growth: | Cream to brown |
| | Aerial Mycelium: | | | |
| | No Soluble Pigment | | | |
| | Complete Liquefaction | | | |
| Litmus Milk | Vegetative Growth: | Tan; sparse growth ring | Vegetative Growth: | Cream colored |
| | Aerial Mycelium: | None | | |
| | Peptonization, alkaline reaction; pH 7.3 - 7.4 (Control pH: 6.7) | | | |

842A Carbohydrate Utilization: The *Streptomyces lactamdurans* culture (MA-2908) was also tested for its ability to utilize or assimilate various carbohydrates by growing the microorganism in a basal synthetic medium (T. G. Pridham and D. Gottlieb; Journal of Bacteriology, Vol. 56: page 107 (1948) which contains 1% of the carbohydrate at 28° C. for three weeks. Table V indicates the utilization or assimilation of these carbohydrate sources by the *Streptomyces lactamdurans* culture (MA-2908). The explanation of the symbols in Table V are as follows: + indicates good growth, ± indicates poor growth and − indicates no growth on the particular carbohydrate.

TABLE V

| Carbohydrate | MA-2908 Culture | Carbohydrate | MA-2908 Culture |
|---|---|---|---|
| Glucose | + | Rhanmose | − |
| Arabinose | + | Cellulose | − |
| Maltose | + | Fructose | ± |
| Raffinose | + | Imositol | − |
| Sucrose | − | Acetate | ± |
| Xylose | + | Citrate | ± |
| Mannitol | + | Paraffin | − |
| Lactose | − | Glycerol | ± |
| Mannose | − | | |

The characteristics described in Tables III, IV and V were used to reduce the *Streptomyces lactamdurans* culture (MA-2908) to a species classification via the keys described in Bergey's Manual of Determinative Bacteriology, Seventh Edition, pages 694–829 (1957) and in The Actinomycetes, Vol. 2: pages 61–292 (1961). A comparison of the detailed characteristics of the *Streptomyces lactamdurans* culture with known species showed that the culture is biochemically similar to *Streptomyces fradiae*. However, as indicated above, there are important morphological differences as, for example, in the color of the aerial mycelium of *S. fradiae* which is seashell pink as compared to the cream color of the culture. Also, the vegetative growth with *S. fradiae* shows pigment differences on the various media and no sporulation was detected with the culture MA-2908. On the basis of these differences and the characteristics described in the foregoing Tables the microorganism producing antibiotic 842A (MA-2908) was assigned the new species name *Streptomyces lactamdurans*.

The foregoing description of the microorganism which produces antibiotic 842A is simply illustrative of the type of strains of microorganisms which can be used and it should be understood that the present invention is not limited to organisms meeting these particular descriptions. This invention includes the use of other microorganisms, including strains of actinomycetes either isolated from nature or obtained by mutation as, for example, those obtained by natural selection or those produced by mutating agents, for example, X-ray irradiation, ultraviolet irradiation, nitrogen mustards and the like which, under suitable conditions, will afford the 842A product.

IN VITRO AND IN VIVO STUDIES

Antibiotic 810A; In vitro: The in vitro biological characterization of Antibiotic 810A was established by the disc-plate agar diffusion method. These tests were performed by placing 7 mm. discs, wet with the antibiotic solution, on the surface of petri plates poured with 5 ml. of Difco Nutrient Agar and 0.2% Yeast Extract seeded with 5 or 10 ml. of inoculum per 150 ml. of medium and incubated at 25° C. or 37° C. for 16 hours.

The method and philosophy of these tests are described in the publication: "Cross Resistance Studies and Antibiotic Identification," Applied Microbiology, Vol. 6: pages 392–398 (1958). The following Tables VI, VII, and VIII set forth the results of these antibacterial and cross-resistance tests and indicate the test organisms used and the conditions employed.

TABLE VI

810A ANTIBACTERIAL SPECTRUM; In Vitro Activity

| Test Organism | Test Conditions | | Inhibition Zone Diameter, mm* |
|---|---|---|---|
| | Inoculum** ml/150 ml | Incubation Temp. ° C. | 810A 5 mg/ml |
| Escherichia coli | 5 | 25 | 15 |
| Bacilius species | 5 | 25 | 22 |
| Proteus vulgaris | 5 | 37 | 29 |
| Pseudomonas aeruginosa | 5 | 25 | 7 |
| Serratia marcescens | 5 | 25 | 7 |
| Staphylococcus aureus | 5 | 25 | 26 |
| Bacillus subtilis | 5 | 25 | 33 |
| Sarcina lutea | 5 | 25 | 26 |
| Staphylococcus aureus (Streptomycin-Streptothricin-resistant) | 5 | 37 | 19 |
| Streptococcus faecalis | 15 | 37 | 7 |
| Alcaligenes faecalis | 5 | 37 | 25 |
| Brucella bronchiseptica | 10 | 37 | 21 |
| Salmonella gallinarum | 10 | 25 | 15 |
| Vibria percolans | 10 | 27 | 36 |
| Xanthomonas vesicatoria | 5 | 25 | 15 |

*7 mm = disc size (no inhibition zone observed)
**Overnight culture dilutes to a reading of 60 mµ on the Lumetron colorimeter.

TABLE VII

810A CROSS-RESISTANCE; In Vitro Study

| Escherichia coli - Strain | Test Conditions | | Inhibition Zone Diameter, mm* |
|---|---|---|---|
| | Inoculum*** ml/150 ml | Incubation Temp. ° C. | 810A 5 mg/ml |
| Sensitive parent | 5 | 25 | 15 |
| Streptomycin-resistant | 5 | 25 | 13 |
| Streptothricin-resistant | 10 | 25 | 17 |
| OXAMYCIN-resistant | 10 | 25 | 10 |
| Pleocidin-resistant | 10 | 37 | 26 |
| Chloramphenicol-resistant | 10 | 25 | 7 |
| Chlortetracycline-resistant | 10 | 25 | 7 |
| Oxytetracycline-resistant | 10 | 25 | 7 |
| Neomycin-resistant | 10 | 37 | 20 |
| Tetracycline-resistant | 10 | 25 | 7 |
| Viomycin-resistant | 10 | 37 | 17 |
| Polymyxin-resistant | 10 | 25 | 13 |
| Grisein-resistant | 5 | 25 | 15 |

*7 mm = disc size (no inhibition zone observed)
**Tests performed versus a series of strains of E. coli isolated from the same parent culture following exposure to the individual antibiotics
***Overnight culture diluted to a reading of 60 mµ on the Lumetron colorimeter.

TABLE VIII

810A SPECIAL EFFECTS SPECTRUM; In Vitro Study

| Escherichia coli W-MB-60 (with special addition noted) | Test Conditions | | Inhibition Zone Diameter, mm* |
|---|---|---|---|
| | Inoculum** ml/150 ml | Incubation Temp. ° C. | 810A 5 mg/ml |
| Control (no additions) | 5 | 25 | 13 |
| 0.1 M Phosphate Buffer - PH 5 | 5 | 25 | 13 |
| 0.1 M Phosphate Buffer - pH 7 | 5 | 25 | 16 |
| 0.1 M Phosphate Buffer - pH 9 | 5 | 25 | 18 |
| Human Blood Plasma 20% | 5 | 25 | 15 |
| Cation Exchange Resin (Dow ET 91-1%; agar concentration reduced to 1% for resin plate only) | 5 | 25 | 12 |

*7 mm disc size (no inhibition zone observed)
**Overnight culture diluted to a reading of 60 mµ on the Lumetron colorimeter.

Antibiotic 810A; In vivo: The in vivo biological characterization indicates that 810A is a broad spectrum antibiotic which protects against infection with two species of Proteus, two of Salmonella, two strains of

*Escherichia coli*, one of Klebsiella and three gram-positive organisms: *Staphylococcus aureus, Streptococcus pyogenes* and *Diplococcus pneumoniae*.

Methods: The method employed in this characterization is as follows: Female white Swiss mice, average weight 20–23 grams, were infected intraperitoneally with 3–20 times the number of organisms calculated to be lethal for 50% of the infected control animals (3–20 $LD_{50}$ doses). At the time of infection and again six hours later, therapy was given by the designated route. Controls of the virulence of the culture and the toxicity of the antibiotic for uninfected mice were included in the tests. Seven days after infection the test was considered complete and the amount of the antibiotic (I) that would be required to protect 50% of the infected and treated animals was calculated by the method of Knudsen and Curtis; J. Amer. Stat. Assoc. Vol. 42: page 282 (1947).

Results: The results of these tests are listed in Table IV, infra. This data indicates that the antibiotic 810A obtained from culture MA-2837 is a broad spectrum agent, protecting against both gram-positive and gram-negative organisms.

Although effective orally (p.o.) 810A is most effective via the subcutaneous (s.c.) or intraperitoneal (i.p.) route. The antibiotic mixture did not kill uninfected mice when two doses containing 1 mg. each of the product were administered intraperitoneally or when two doses of 18 mg. each were administered subcutaneously or orally.

TABLE IX

| Test Organism | 810A In Vivo Activity Route of Therapy | $ED_{50}$ in Micrograms × Two Doses |
|---|---|---|
| *Proteus vulgaris* | i.p. | 33 |
| | s.c. | 500 |
| | p.o. | 12100 |
| *Proteus mirabilis* | i.p. | 200 |
| | p.o. | >5000 |
| *Salmonella schottmuelleri* | i.p. | 419 |
| | s.c. | 9000 |
| *Escherichia coli* | i.p. | 3750 |
| *Escherichia coli* | i.p. | 1330 |
| *Klebsiella pneumoniae* | i.p. | 2500 |
| *Salmonella gallinarum* | i.p. | 1670 |
| *Salmonella pullorum* | i.p. | 625 |
| *Diplococcus pneumoniae* | i.p. | 258 |
| *Staphylococcus aureus* | i.p. | 927 |
| *Streptococcus pyogenes* | i.p. | 625 |

Antibiotic 842A; In vitro: The in vitro biological characterization was established by the disc-plate agar diffusion method. These tests were performed by placing 7 mm. discs, wet with the antibiotic solution, on the surface of petri plates poured with 5 ml. of Difco Nutrient Agar and 0.2% Yeast Extract seeded with 5 or 10 ml. of standard cell suspension (OD = 0.22 at 660 m$\mu$) per 150 ml. of medium and incubated at 25° or 37° C. for 16 hours as indicated. The method and philosophy of these tests are described in the publication: "Cross Resistance Studies and Antibiotic Identification," Applied Microbiology, Vol. 6: pages 392–398 (1958). The following Tables set forth the results of these antibacterial spectrum and cross-resistance tests, and indicate the test organisms used and the conditions employed.

TABLE X

842A ANTIBACTERIAL SPECTRUM; IN VITRO ACTIVITY

| | Test Conditions | | INHIBITION ZONE DIAMETER, mm* | | |
|---|---|---|---|---|---|
| Test Organism | Inoculum ml/150 ml | Incubation Temp. ° C. | Crude 842A (lb) 8 mg/ml | Free Acid 166 µg/ml | Sodium Salt 192 µg/ml |
| *Escherichia coli* | 5 | 25 | 16 | 20 | 18 |
| *Bacillus sp.* | 5 | 25 | 7 | 8 | 7 |
| *Proteus vulgaris* | 5 | 37 | 21 | 22 | 24 |
| *Pseudomonas aeruginosa* | 5 | 25 | 7 | 7 | 7 |
| *Serratia marcescens* | 5 | 25 | 7 | 7 | 7 |
| *Staphylococcus aureus* | 5 | 25 | 7 | 7 | 7 |
| *Bacillus subtilis* | 5 | 25 | 16 | 13 | 18 |
| *Sarcina lutea* | 5 | 25 | 9 | 10 | 9 |
| *Staphylococcus aureus* (Streptomycin-Streptothricin-resistant) | 5 | 37 | 7 | 11 | 10 |
| *Streptococcus faecalis* | 15 | 37 | 7 | 7 | 7 |
| *Alcaligenes faecalis* | 5 | 37 | 22 | 27 | 7 |
| *Brucella bronchiseptica* | 10 | 37 | 28 | 24 | 26 |
| *Salmonella gallinarum* | 10 | 25 | 20 | 21 | 25 |
| *Vibrio percolans* | 10 | 27 | 37 | 56 | 38 |
| *Xanthemenia vesicateria* | 5 | 25 | 12 | 19 | 17 |

*7 mm = disc size (No inhibition zone observed)

TABLE XI

842A CROSS RESISTANCE; IN VITRO STUDY

| | Test Conditions | | INHIBITION ZONE DIAMETER, mm** | | |
|---|---|---|---|---|---|
| *Escherichia coli* - Strain | Inoculum ml/150 ml | Incubation Temp. ° C. | Crude 842A (lb) 8 mg/ml | Free Acid 166 µg/ml | Sodium Salt 192 µg/ml |
| Sensitive parent | 5 | 25 | 16 | 20 | 18 |
| Streptomycin-resistant | 5 | 25 | 14 | 19 | 16 |
| Streptothricin-resistant | 10 | 25 | 13 | 14 | 18 |
| OXMYCIN-resistant | 10 | 25 | 13 | 13 | 17 |
| Pleocidin-resistant | 10 | 37 | 15 | 18 | 17 |
| Chloramphenicol-resistant | 10 | 25 | 13 | 17 | 16 |
| Chlortetracycline-resistant | 10 | 25 | 21 | 20 | 23 |
| Oxytetracycline-resistant | 10 | 25 | 20 | 23 | 24 |
| Neomycin-resistant | 10 | 37 | 18 | 17 | 17 |
| Tetracycline-resistant | 10 | 25 | 16 | 20 | 20 |
| Viomycin-resistant | 10 | 37 | 15 | 16 | 30 |
| Polymyxin-resistant | 10 | 25 | 23 | 21 | 7 |

TABLE XI-continued

842A CROSS RESISTANCE; IN VITRO STUDY

| Escherichia coli - Strain | Test Conditions | | INHIBITION ZONE DIAMETER, mm** | | |
|---|---|---|---|---|---|
| | Inoculum ml/150 ml | Incubation Temp. °C. | Crude 842A (Ib) 8 mg/ml | Free Acid 166 μg/ml | Sodium Salt 192 μg/ml |
| Grisoin-resistant | 5 | 25 | 18 | 21 | 16 |

*Tests performed versus a series of strains of E. coli isolated from the same parent culture following exposure to the individual antibiotics
**7 mm = disc size (no inhibition zone observed)

TABLE XIa

842A SPECIAL EFFECT SPECTRUM; IN VITRO STUDY

| Escherichia coli W-MB-60 (with special addition noted) | Test Conditions | | INHIBITION ZONE DIAMETER, mm* | | |
|---|---|---|---|---|---|
| | Inoculum ml/150 ml. | Incubation Temp. °C. | Crude 842A (Ib) 8 mg/ml | Free Acid 166 μg/ml | Sodium Salt 192 μg/ml |
| Control (no additions) | 5 | 25 | 16 | 20 | 18 |
| 0.1 M Phosphate Buffer -pH 5 | 5 | 25 | 19 | 20 | 15 |
| 0.1 M Phosphate Buffer -pH 7 | 5 | 25 | 22 | 29 | 25 |
| 0.1 M Phosphate Buffer -pH 9 | 5 | 25 | 21 | 22 | 24 |
| Human Blood Plasma 20% | 5 | 25 | 17 | 22 | 21 |
| *Cation Exchange Resin (Dow ET 91)1% | 5 | 25 | 20 | 21 | 18 |

*(Agar concentration reduced to 1% for resin plate only)

Antibiotic 842A: In Vivo

When 842A is given subcutaneously to mice it is generally more active than cephalothin and approximately equal to cephaloridine, ampicillin and chloromycetin in protecting against infection from gram-negative organisms. It is remarkably nontoxic and is rapidly excreted in the urine with approximately 79% of the subcutaneously injected 842A recovered within four hours.

In in vivo studies Antibiotic 842A protects against infection with three species of Proteus, two of Salmonella, one strain of *Escherichia coli*, two of Klebsiella and also against *Paracolobactrum arizonae, Aerobacter aerogenes, Pasteurella multocida* and *Diplococcus pneumoniae* 2400.

The method employed in these studies is the same as described above with regard to the in vivo characterization of 810A. The results of these tests are described below in Table XIb:

TABLE XIb

| Test Organism | 842A In Vivo Activity ED$_{50}$ by Subcutaneous Route × Two Doses |
|---|---|
| Proteus vulgaris | 51 μg. |
| Proteus mirabilis | 276 μg. |
| Proteus morganii 3202 | 276 μg |
| Salmonella schottmuelleri | 103 μg. |
| Klebsiella pneumoniae AD | 125 μg. |
| Klebsiella pneumoniae B | 125 μg. |
| Paracolobactrum arizonae | 125 μg. |
| Escherichia coli | 200 μg. |
| Aerobacter aerogenes | 49 μg. |
| Pasteurella multocida | 57 μg. |
| Salmonella typhosa | 33 μg. |
| Diplococcus pneumoniae 2400 | 566 μg. |

THE ANTIBIOTICS

810A Fermentation: The Antibiotic 810A is produced during the aerobic fermentation of suitable aqueous nutrient mediums under controlled conditions via inoculation with the *Streptomyces griseus* culture MA-2837. Aqueous mediums such as those employed for the production of other antibiotics are also suitable for producing Antibiotic 810A. Such mediums contain sources of carbon and nitrogen assimilable by the microorganism and inorganic salts.

In general, carbohydrates such as sugars, for example, glucose, arabinose, maltose, xylose, mannitol and the like and starches such as grains, for example, oats, rye, corn starch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1 and 6% by weight of the medium. These carbon sources can be used individually or several such carbon sources may be combined in the medium. In general any proteinaceous material may be used as a nitrogen source in the fermentation process. Suitable nitrogen sources include, for example, yeast hydrolysates, yeast autolysate, soybean meal, hydrolysates of casein, corn steep liquor, distiller's solubles or tomato paste and the like. The sources of nitrogen, either alone or in combination, are used in amounts ranging from about 0.2 to 6% by weight of the aqueous medium. Typical of the mediums which are suitable for the preparation of Antibiotic 810A are those listed below. These mediums and others described in the examples which follow are merely illustrative of the wide variety of media which may be employed and are not intended to be limitative.

| Medium I: | |
|---|---|
| Difco Yeast Extract | 10.0 g. |
| Glucose | 10.0 g. |
| *Phosphate Buffer | 2.0 ml. |
| MgSO$_4$ . 7H$_2$O | 0.05 g. |
| Distilled Water | 1000.0 ml. |
| Difco Agar | 25.0 g. |
| *Phosphate Buffer: | |
| KH$_2$PO$_4$ | 91.0 g. |
| Na$_2$HPO$_4$ | 95.0 g. |
| Distilled Water | 1000.0 ml. |
| Medium II: | |
| Beef Extract | 3.0 g. |
| *NZ Amine | 10.0 g. |
| Dextrose | 10.0 g. |
| NaCl | 5.0 g. |
| Distilled H$_2$O | 1000.0 ml. |
| pH adjusted to 7.2 with NaOH | |

*an enzymatic digested casein

Medium III:

-continued

| | |
|---|---|
| Dextrose | 10.0 g. |
| Asparagine | 1.0 g. |
| K$_2$HPO$_4$ | 0.1 g. |
| MgSO$_4$ . 7H$_2$O | 0.5 g. |
| Yeast Extract | 0.5 g. |
| *Trace Element Mix No. 2 | 10.0 ml. |
| Distilled H$_2$O | 1000.0 ml. |
| pH adjusted to 7.2 with NAOH | |

*Trace Element Mix No. 2:

| | |
|---|---|
| FeSO$_4$ . 7H$_2$O | 1.0 g. |
| MnSO$_4$ . H$_2$O | 1.0 g. |
| CuCl$_2$ . 2H$_2$O | 25.0 mg. |
| CaCl$_2$ | 100.0 mg. |
| H$_3$BO$_3$ | 56.0 mg. |
| (NH$_4$)$_6$MO$_7$O$_{24}$ . 4H$_2$O | 19.0 mg. |
| ZnSO$_4$ . 7H$_2$O | 200.0 mg. |
| Distilled H$_2$O | 1000.0 ml. |

Medium IV:

| | |
|---|---|
| V( Juice | 100.0 ml. |
| Staley's 4S Soybean Meal | 20.0 g. |
| Dextrose | 2.0 g. |
| Agar | 25.0 g. |
| Distilled H$_2$O | to 1000.0 ml. |
| pH 7.9–8.0 | |

Medium V:

| | |
|---|---|
| Yeast Autolysate (Ardamine) | 10.0 g. |
| Glucose | 10.0 g. |
| *Phosphate Buffer | 2.0 ml. |
| MGSO$_4$ . 7H$_2$O | 0.05 g. |
| Distilled H$_2$O | 1000.0 ml. |
| pH - adjust to 6.5 using NaOH | |

*Phosphate Buffer Solution:

| | |
|---|---|
| KH$_2$PO$_4$ | 91.0 g. |
| Na$_2$HPO$_4$ | 95.0 g. |
| Distilled H$_2$O | 100.0 ml. |

Medium VI:

| | |
|---|---|
| Corn Steep Liquor (wet basis) | 40.0 g. |
| Dextrose | 20.0 g. |
| NaCl | 2.5 g. |
| MgSOj$_4$ . 7H$_2$O | 0.5 g. |
| Polyglycol 2000 | 0.25 % by volume (add to each flask individually) |
| Distilled H$_2$O | 1000.0 ml. |
| pH - adjust to 7.0 with NaOH | |

| Medium VII: | Seed | Production |
|---|---|---|
| L-Asparagine | 5.0 g. | 5.0 g. |
| L-Histidine | 4.0 g. | 4.0 g. |
| DL-Phenylalanine | — | 2.0 g. |
| Monosodium glutamate | — | 1.5 g. |
| NaCl | 5.0 g. | 5.0 g. |
| K$_2$HPO$_4$ | 2.0 g. | 2.0 g. |
| CaCl$_2$ . 2H$_2$O | 0.4 g. | 0.4 g. |
| MnSO$_4$ . H$_2$O | 0.1 g. | 0.1 g. |
| FeSOj$_4$ . 7H$_2$O | 0.1 g. | 0.1 g. |
| ZnSOj$_4$ . 7H$_2$O | 0.05 g. | 0.05 g. |
| MgSO$_4$ . 7H$_2$O | 1.0 g. | 1.0 g. |
| Glycerol | 20.0 g. | 20.0 g. |
| Sucrose | 2.5 g. | 2.5 g. |
| Distilled H$_2$O | *1000.0 ml. | *1000.0 ml. |

*pH adjusted to 7.0 with NaOH
**pH adjusted to 7.1 with NaOH

Medium VIII:

| | |
|---|---|
| Meat Extract | 0.3% |
| NaCl | 0.5% |
| NZ Amine | 1% |
| Dextrose | 1% |
| pH 7.0 | |

The fermentation is carried out at temperatures ranging from about 20° to 37° C; however, for optimum results it is preferable to conduct the fermentation at temperatures of from about 22° to 30° C. The pH of the nutrient mediums suitable for growing the *Streptomyces griseus* culture (MA-2837) and producing Antibiotic 810A should be in the range of from about 5.5 to 8.0.

A small scale fermentation of Antibiotic 810A is conveniently carried out by inoculating a suitable nutrient medium with the antibiotic-producing culture and permitting the fermentation to proceed at a constant temperature of from about 24°–28° C. on a shaker over an extended period as, for example, for several days. At the end of the incubation period the mycelium is removed and the supernatant liquid is assayed.

In practice this fermentation is conducted in a sterilized flask via a one, two, three or four stage seed development. The nutrient medium for the seed stage may be any suitable combination of carbon and nitrogen sources ask, for example, any one of Mediums I–VIII described above. The seed flask is shaken in a constant temperature chamber at about 28° C. for a period of from one to about three days and the resulting growth is used to inoculate either a second stage seed or the production medium. Intermediate stage seed flasks, when used, are developed in essentially the same manner, that is, the contents of the flask are used to inoculate the production medium, the inoculated flasks are shaken at a constant temperature for several days and at the end of the incubation period the contents of the flask are centrifuged to remove the mycelium. The supernatant liquid or broth is then concentrated and purified to afford the Antibiotic 810A.

For larger scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with the producing culture and the fermentation is permitted to proceed for a period of several days as, for example, from two to four days while agitating and/or aerating the nutrient medium and maintaining the temperature at about 24°–28° C. Through changes in inoculum development and changes in production medium it is possible to achieve a several-fold improvement in production and increase the potency of the antibiotic.

810A Assay Procedure Using *Proteus vulgaris*: Antibiotic 810A was conveniently assayed by a disc-plate procedure using *Proteus vulgaris* MB-838 (ATCC 21100 and NRRL B-3361) maintained as a slant culture on nutrient agar (Difco) plus 0.2% yeast extract (Difco) as the test organism. The inoculated slants are incubated at 37° C. for 18–24 hours and stored at refrigerator temperatures until used, fresh slants being prepared each week.

The inoculum for the assay plates is prepared each day by inoculating a 250 ml. Erlenmeyer flask containing 50 ml. of nutrient broth (Difco) plus 0.2% yeast extract (Difco) with a scraping from the slant. The flask is incubated at 37° C. on a shaking machine for 18–24 hours. The broth culture is then adjusted to 40% transmittance at a wavelength of 660 nm, using a Bausch & Lomb Spectronic 20 by the addition of a 0.2% yeast extract solution to the growth. Uninoculated broth is used as a blank for this determination. The adjusted broth (30 ml.) is used to inoculate 1 liter of medium.

Nutrient agar (Difco) plus 0.2% yeast extract (Difco) is used as the assay medium. This medium is prepared, sterilized by autoclaving and allowed to cool to 50° C. After the medium is inoculated, 10 ml. is added to each of several sterile petri dishes and the medium is allowed to solidify.

Assays were run on these plates by the disc-plate procedure using 0.5 inch filter paper discs. The assay plates were incubated for 20–24 hours at 37° C. Assays are expressed as mm. diameter zone of inhibition. They are used to determine relative potencies or, when compared with a purified reference standard, the potency in μg./ml. When such an assay is performed in a quantitative fashion from 2 to 4 μg./ml. of antibiotic can be detected.

810A Assay Procedure Using Vibrio percolans: Assays were also run on 810A by the disc-plate procedure against *Vibrio percolans* (MB-1272) using 0.5 inch filter paper discs. The assay plates were prepared using Difco nutrient agar plus 2.0 g./liter Difco yeast extract at 10 ml. per plate. An overnight growth of the assay organism, *Vibrio percolans* (MB-1272) in nutrient broth plus 0.2% yeast extract was diluted in sterile saline solution to a suspension having 40% transmittance at a wave length of 660 mμ. This suspension was added at 20 ml./liter of medium prior to pouring the plates.

The assay plates were held at 4° C. until used (5 day maximum). Following the application of antibiotic-saturated assay discs the plates were incubated at 28° C. for a period of from 8 to 24 hours. Zones of inhibition were read as mm. diamter.

Bacterial Inactivation with 810A: An in vitro study was designed to determine the resistance of Antibiotic 810A, to bacterial inactivation as compared with cephalosporin C, cephaloridine and cephalothin. This study showed that Antibiotic 810A is more stable than the latter against certain microorganisms.

The degradative bacterium used in this study was an organism known to completely inactivate cephalosporin C, namely, *Alcaligenes faecalis* (MB-9).

a. Preparation of Bacterial Cells: *Alcaligenes faecalis* (MB-9) cells were prepared as follows: the contents of an L-tube were mixed with a few ml. of nutrient broth containing 0.2% yeast extract. A loopful of the slurry was spread over the surface of a nutrient agar slant and incubated for 18 hours at 37° C. All slants were stored at 5° C. and used within one week after incubation. A loopful of the surface growth from each slant culture was aseptically transferred to 50 ml. of nutrient broth containing 0.2% yeast extract and shake incubated for 18 hours at 28° C. The culture was then centrifuged at 4,000 rpm. for ten minutes. The supernatant was decanted and the residual pellet of cells was washed twice with sterile 0.1 M phosphate buffer, pH 7.5 (6.8 g. of potassium phosphate and 7.1 g. of sodium hydrogen phosphate per liter of distilled water). The washed cells were then resuspended in one-tenth original volume of a 4 mg./ml. solution of antibiotic in 0.1 M phosphate buffer. The test mixture was then incubated without shaking in a water bath set at 37° C. for up to 4 hours. The test mixtures were then centrifuged at 2,000 rpm. for 10 minutes and this produced a clear supernatent which was decanted into sterile tubes and immediately frozen in dry ice until ready for bioassay, usually within three hours. Controls were incubated in exactly the same manner, except for the absence of cells.

b. Extent of Antibiotic 810A Inactivation: The supernatants were tested for antibacterial activity in the following manner: ¼ inch diameter paper discs were moistened with the supernatants and placed on the surface of nutrient agar-yeast extract (0.2%) plates that had been previously seeded with the appropriate test organism. *B. subtilis* (MB-964) assay plates were seeded in the following manner: 5 ml. of a suspension of washed spores in 0.9% saline was added to each 150 ml. of nutrient agar-yeast extract (0.2%) of which 5 ml. was then dispensed into 15 × 100 mm. petri plates. All assay plates were stored at 5° C. and used within three days. Assay plates were incubated overnight at 25° C. before measurement of zones of inhibition around the test discs.

Cell-free controls of each antibiotic were assayed at 1:1, 1:2, 1:4, 1:8, 1:16 and 1:32 dilutions in order to obtain a standard reference curve. Solutions of test antibiotics were assayed at full strength after incubation in the presence of the washed bacterial cells. All samples were run in triplicate.

c. Results: Percents of inactivation were calculated taking the average of the three zones of inhibition obtained for each test and determining the amount of antibiotic remaining in the test solution as shown by the the standard curve. This value was then subtracted from the starting concentration (4 mg./ml.) and the remainder divided by the starting concentration and multiplied by 100 to obtain the percent of inactivation. The following Tables XII and XIII demonstrate the inactivation obtained for cephalosporin C, cephalothin and Antibiotic 810A under the conditions described above.

TABLE XII

Percent Inactivation After Incubation With Washed Bacterial Cells (Assayed on *B. subtilis* (MB-964) Plates)

| Antibiotic | 3 Hour Incubation With *Alcaligenes faecalis* |
|---|---|
| 810A | 0 |
| Cephalosporin C | 99+ |
| Cephalothin | 62.5 |

TABLE XIII

Percent Inactivation After Incubation With Washed Bacterial Cells (Assayed on *V. percolans* (MB-1272) Plates)

| Antibiotic | 3 Hour Incubation With *Alcaligenes faecalis* |
|---|---|
| 810A | 0 |
| Cephalosporin C | 99+ |
| Cephalothin | 50 |

The ability of Antibiotic 810A and cephalosporin C to withstand the degradative effect of the culture *Aerobacter cloacae* (MB-2646) was also determined. This culture is gram-negative and resistant to cephalosporin C. In conducting the assay individual mixtures of the organisms and one of the antibiotic mixtures were sampled after two hours incubation and assayed for residual antibiotic activity. The procedure is the same assay method as described above with *Alcaligenes faecalis*. The source of the inactivating substance is a 1:160 dilution of the filtrate of an 18 hour 37° C. shake culture of *Aerobacter cloacae* MB-2646 in nutrient broth containing 0.2% yeast extract. Table XIV, infra, indicates the percent inactivation of Antibotic 810A, cephalothin, cephaloridine and cephalosporin C on *Vibrio percolans* (MB-1272) via this method:

TABLE XIV

Percent Inactivation After Incubation With Cell-Free Extract
(Assayed on *V. percolans* (MB-1272) Plates)

| Antibiotic | 2 Hour Incubation With *Aerobacter cloacae* |
|---|---|
| 810A | 16 |
| Cephalothin | 66 |
| Cephaloridine | 96 |
| Cephalosporin C | 96 |

Using the same assay procedure as described above, Table XV, infra, indicates the relative resistance of Antibiotic 810A to enzymatic inactivation by *Aerobacter cloacae*. The starting concentration is 250 µg./ml. Results are expressed in µg./ml.

TABLE XV

Antibiotic Activity Remaining (µg./ml.)
(Starting Concentration = 250 µg./ml.)

| Antibiotic | Assay Organism | 2 Hour Incubation With *Aerobacter cloacae* |
|---|---|---|
| 810A | *B. subtilis* 964 | 190 |
| Cephalothin | " | 140 |
| Cephaloridine | " | <10 |
| 810A | *V. percolans* 1272 | 210 |
| Cephalothin | " | 85 |
| Cephaloridine | " | <10 |

*Cell-free extract

In view of the foregoing, Antibiotic 810A is, apparently, more resistant than cephalosporin C, cephalothin and cephaloridine to inactivation by *Aerobacter cloacae*.

842A Fermentation: Antibiotic 842A is produced during the aerobic fermentation of suitable aqueous nutrient mediums under controlled conditions via inoculation with the organisms *Streptomyces lactamdurans*. In general, many media which are a source of carbon and nitrogen may be used for the production of 842A. Illustrative of these are the aqueous mediums and carbohydrate and nitrogen sources described above in connection with the fermentation of 810A. The exact amount of the carbohydrate and nitrogen sources will depend upon the other ingredients comprising the fermentation medium but, in general, the amount of carbohydrate is usually about 1 to 6% by weight of the medium and the amount of available nitrogen, either alone or in combination is usually in the amount from about 0.2 to about 6% by weight of the medium. The several media described below are illustrative of those which are suitable for the preparation of Antibiotic 842A. These media are merely typical of the media which may be employed and are not intended to be limitative.

| Medium IX: | |
|---|---|
| Amber Yeast No. 300 | 10.0 g. |
| Distiller's Solubles | 20.0 g. |
| Dextrose | 10.0 g. |
| Distilled Water | 1000.0 ml. |
| pH 7.0 | |
| Medium X: | |
| Staley's 4S-Soybean Meal | 30.0 g. |
| Distiller's Solubles | 7.5 g. |
| Cerelose | 20.0 g. |
| NaCl | 2.5 g. |
| CaCO$_3$ (after pH to 7.0) | 10.0 g. |
| Distilled Water | 1000.0 ml. |
| Medium XI: | |
| Amber Yeast No. 300 | 10.0 g. |
| Distiller's Solubles | 20.0 g. |
| Distilled Water | 1000.0 ml. |
| pH 7.0 | |

The fermentation is carried out at temperatures ranging from about 20° to 37° C. but, for optimum results it is preferable to conduct the fermentation at temperatures of from about 24° to 32° C. The pH of the nutrient mediums suitable for growing the *Streptomyces lactamdurans* culture (MB-2908) and producing Antibiotic 842A should be in the range of from about 6.0 to about 8.0.

A small scale fermentation of Antibiotic 842A is conveniently carried out by inoculating a suitable nutrient medium with the antibiotic-producing culture and permitting the fermentation to proceed at a constant temperature of about 28° C. on a shaker for several days. At the end of the incubation period the mycelium is removed and the supernatant liquid is assayed.

In practice, this fermentation is conducted in a sterilized flask via a one, two, three or four stage seed development. The nutrient medium for the seed stage may be any suitable combination of carbon and nitrogen sources as, for example, any one of Mediums IX–XI described above. The seed flask is shaken in a constant temperature chamber at about 28° C. for a period of from 1 to about 3 days and the resulting growth is used to inoculate either a second stage seed or the production medium. Intermediate stage seed flasks, when used, and developed in essentially the same manner, that is, the contents of the flask are used to inoculate the production medium, the inoculated flasks are shaken at a constant temperature for several days and at the end of the incubation period the contents of the flasks are centrifuged to remove the mycelium. The supernatant liquid or broth is then concentrated and purified to afford Antibiotic 842A.

For larger scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with the producing culture and the fermentation is permitted to proceed for a period of several days as, for example, from 2 to 4 days while agitating and/or aerating the nutrient medium and maintaining the temperature at about 28° C. Through changes in inoculum development and changes in production medium it is also possible to achieve a several-fold improvement in production and increase the potency of this antibiotic.

842A Assay Procedure Using Vibrio percolans: Assays were run by the disc-plate procedure using 0.5 inch filter paper discs. The assay plates were prepared using Difco nutrient agar plus 2.0 g./l. Difco yeast extract at 10 ml. per plate. An overnight growth of the assay organism, *Vibrio percolans* (MB-1272) in nutrient broth and 0.2% yeast extract was diluted in sterile saline solution to a suspension having 40% transmittance at a wave length of 660 nm. This suspension was added at 20 ml./liter of medium prior to pouring the plates.

The assay plates were held at 4° C. until used (5 day maximum). Following the application of the antibiotic-saturated assay discs the plates were incubated at 28° C. for a period of from 8 to 24 hours. Zones of inhibition were read as mm. diameter. They were used to determine relative potencies or, when compared with a purified reference standard, the potency in μg./ml. When such an assay is performed in a quantitative fashion from 1 to 2 μg./ml. of antibiotic can be detected.

Bacterial Inactivation With 842A: An in vitro study was designed to determine the resistance of Antibiotic 842A to bacterial inactivation as compared with cephalosporin C, cephaloridine and cephalothin. This study showed that Antibiotic 842A is more stable than the latter against certain microorganisms.

The degradative bacteria used in the study were two organisms known to completely inactivate cephalosporin C, namely, *Alcaligenes faecalis* (MB-9) and *Alcaligenes viscosus* (MB-12).

a. Preparation of Bacterial Cells: *Alcaligenes viscosus* (MB-12) and *A. faecalis* (MB-9) cells were prepared as follows: tho contents of an L-tube were mixed with a few ml. of nutrient broth containing 0.2% yeast extract. A loopful of the slurry was spread over the surface of a nutrient agar slant and incubated for 18 hours at 37° C. All slants were stored at 5° C. and used within one week after incubation. A loopful of the surface growth from each slant culture was asceptically transferred to 50 ml. of nutrient broth containing 0.2% yeast extract and shake incubated for 18 hours at 28° C. The culture was then centrifuged at 4000 rpm. for ten minutes. The supernatant was decanted and the residual pellet of cells was washed twice with sterile 0.1 M phosphate buffer, pH 7.5 (6.8 g. of potassium phosphate, i.e., $KH_2PO_4$ and 7.1 g. of sodium hydrogen phosphate per liter of distilled water). The washed cells were then resuspended in one-tenth original volume of a 4 mg./ml. solution of antibiotic in 0.1 M phosphate buffer. The test mixture was then incubated without shaking in a water bath set at 37° C. for four hours. The test mixtures were then centrifuged at 2000 rpm. for 10 minutes and this produced a clear supernatant which was decanted into sterile tubes and inmediately frozen in dry ice until ready for bioassay, usually within three hours. Controls were incubated in exactly the same manner, except for the absence of cells.

b. Extent of Antibiotic 842A Inactivation: The supernatants were tested for antibacterial activity in the following manner: ¼ inch diameter paper discs were moistened with the supernatants and placed on the surface of nutrient agar-yeast extract (0.2%) plates that had been previously seeded with the appropriate test organism. *B. subtilis* (MB-964) assay plates were seeded in the following manner: 5 ml. of a suspension of washed spores in 0.9% saline was added to each 150 ml. of a 2% nutrient agar-yeast extract (45° C.) of which 5 ml. was then dispensed into 15 × 100 mm. petri plates. All assay plates were stored at 5° C. and used within three days. Assay plates were incubated overnight at 25° C. before measurement of zones of inhibition around the test discs.

Cell-free controls of each antibiotic were assayed at 1:1, 1:2, 1:4, 1:8, 1:16 and 1:32 dilutions in order to obtain a standard reference curve. Solutions of test antibiotics were assayed at full strength after incubation in the presence of the washed bacterial cells. All samples were run in triplicate.

c. Results: Percents of inactivation were calculated by taking the average of the three zones of inhibition obtained for each test and determining the amount of antibiotic remaining in the test solution as shown by the standard curve. This value was then subtracted from the starting concentration (4 mg./ml.) and the remainder divided by the starting concentration and multiplied by 100 to obtain the percent of inactivation. The following Table XVI demonstrates the inactivation obtained for cephalosporin C and Antibiotic 842A under the conditions described above.

TABLE XVI

| DEGRADATIVE ORGANISM | Percent Inactivation After Incubation With Washed Bacterial Cells (Asayed on *B. subtilis* (MB-964) Plates) 4 Hour Incubation | |
|---|---|---|
| | Ceph C | Antibiotic 842A |
| *Alcaligenes faecalis* MB-9 | 99+ | 0 |
| *A. viscosus* MB-12 | 99+ | 54.4 |

The ability of Antibiotic 842A and cephalosporin C to withstand the degradative effect of four other cultures was also determined. These cultures are: *Escherichia coli* 236, *Proteus morganii* 251, *Proteus morganii* 356 and *Proteus mirabilis* 241. Each is gram-negative and resistant to cephalosporin C. In conducting the assay, individual mixtures of the organisms and one of the antibiotics were sampled after four hours incubation and assayed for residual antibiotic activity. The procedure is the same assay method as described above against *Alcaligenes faecalis* MB-9 and *A. viscosus* MB-12. The following table indicates the percent inactivation of cephalosporin C and 842A on *B. subtilis* (MB-964) via this method:

TABLE XVII

| Culture | Ceph C | Antibiotic 842A |
|---|---|---|
| *Escherichia coli* 236 | >99 | 38 |
| *Proteus morganii* 251 | >99 | 80 |
| *Proteus morganii* 356 | >99 | 69 |
| *Proteus mirabilis* 241 | 72 | 5 |

The foregoing data indicates that Antibiotic 842A is, apparently, more resistant than cephalosporin C to inactivation by *A. faecalis*, *A. viscosus*, *Escherichia coli* 236, *Proteus morganii* 251, *Proteus morganii* 236 and *Proteus mirabilis* 241.

The antibiotic 842A which is obtained via the instant fermentation process is an amphoteric compound with an apparent isoelectric point of about pH 3.5; it is unstable above pH 9.0 but relatively stable at pH 1.5.

Since Antibiotic 810A and Antibiotic 842A and their salts effectively inhibit the growth of various species of Salmonella they can be used as disinfectants in various household and industrial applications. For example, 810A exhibits activity against *Salmonella schottmuelleri* and *S. gallinarum* and 842A exhibits activity against *Salmonella schottmuelleri* 3010, *S. gallinarum* and *S. typhosa* and this property is indicative of their usefulness as sanitizing agents in household and industrial applications.

ISOLATION AND PURIFICATION

Antibiotic 810A: Antibiotic 810A can be purified by adsorption on an ion exchange resin as, for example, on synthetic anion exchange resins derived from dextrose or acrylic copolymers or non-ionic cross-linked polymers. The adsorbed antibiotic is eluted from the resin or polymer adsorbate with water or with an aqueous alcoholic solution of a suitable salt such as ammonium chloride or sodium chloride and the like. Illustrative of the ion exchange resins and polymers which may be employed are, for example, the DEAE Sephadex A-25, Amberlite IRA-68 and Amberlite XAD-2 mediums described below. If desired the eluate obtained according to the foregoing procedure can be further purified by a second and third adsorption and elution step. Concentrates of all the eluates are then obtained to afford the purified product.

810A Components: Antibiotic 810A can be separated into its components, 7β-(D-5-amino-5-carboxyvaleramido)-3-(α-methoxy-p-sulfooxycinnamoyloxymethyl)-7-methoxy-3-cephem-4-carboxylic acid and 7β-(D-5-amino-5-carboxyvaleramido)-3-(α-methoxy-p-hydroxycinnamoyloxymethyl)-7-methoxy-3-cephem-4-carboxylic acid, by chromatographic means. These include:

1. Chromatography on a strongly hydrophylic anion exchange resin such as *DEAF Sephadex A-25, developed with an ammonium bromide-formic acid system. Various concentration of this system may be employed but, in practice, a 0.5 M ammonium bromide — 0.1 M formic acid solution is preferred.

*DEAE Sephadex A-25 is a synthetic anion exchange resin derived from the polysaccharide, dextran in its chloride form i.e., with chloride counter ions; Pharmacia Fine Chemicals, Inc., 800 Centenial Avenue, Piscataway, New Market, N.J. 08854.

2. Chromatography on a weakly basic anion exchange resin such as **Amberlite IRA-68. This is a group separation where material in crude form is fed at a pH of about 3 to 3.5 and eluted first with an acid at a pH of about 2 and then with NaCl/HCl at a pH of about 1.

** A synthetic anion exchange resin; a cross-linked acrylic copolymer containing weakly basic tertiary amino groups; Rohm & Haas Co., Philadelphia, Pa. 19105.

3. Chromatography on a non-inoic cross-linked polystyrene polymer such as ***Amberlite XAD-2. Elution is effected with a suitable aqueous system but, in general, it is most advantageous to employ a mixture of water and a lower alkyl ketone. Typical of the eluants which may be employed are, for example, 10% methanol in water followed by 50% methanol in water. Alternatively, 20% acetone in water can be substituted for the 50% methanol in water solution.

*** A non-ionic cross-linked polystyrene polymer sorbent; Rohm & Haas Co., Phila. Pa. 19105.

The individual products obtained via the above methods may be purified by rechromatography. Thus, for example, 7β-(D-5-amino-5-carboxyvaleramido)-3-(α-methoxy-p-sulfooxycinnamoyloxymethyl)-7-methoxy-3-cephem-4-carboxylic acid (Ic) may be repurified by subjecting that product to the purification method described in Method 1, supra, followed by desalting on Amberilite XAD-2 absorbent; and 7β-(D-5-amino-5-carboxyvaleramido)-3-(α-methoxy-p-hydroxycinnamoyloxymethyl)-7-methoxy-3-cephem-4-carboxylic acid may be repurified by rechromatography on a Sephadex A-25 anion exchange resin developed with 0.5 M ammonium bromide and 0.05 M acetic acid.

Antibiotic 842A: The Antibiotic 842A can be purified by adsorption on an ion exchange resin as, for example, on resins composed of quaternary ammonium or sulfonic acid exchange media. The adsorbed antibiotic is eluted from the resin adsorbate with aqueous solution or with an aqueous alcoholic solution of a suitable salt such as ammonium chloride, sodium chloride and the like. Suitable ion exchange resins which may be employed include, for example, the polystyrene nuclear sulfonic acid resins (45 or 53% water) or polystyrene trimethylbenzylammonium resins (43% water) which are known as Dowex 50 and Dowex 1, respectively. If desired the eluate obtained according to the foregoing procedure can be further purified by a second and third adsorption and elution step. Concentrates of all the eluates are then obtained to afford the purified 842A product.

FORMULATIONS

Antibiotic 810A and its individual components and Antibiotic 842A may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly. Suitable carriers which may be used in the composition include, for example, mannitol, sucrose, glucose or sterile liquids such as water, saline, glycols and oils of a petroleum, animal, vegetable or synthetic origin as, for example, peanut oil, mineral oil or sesame oil. Also, in addition to a carrier the instant compositions may also include other ingredients such as stabilizers, binders, antioxidants, preservatives, lubricators, suspending agents, viscosity agents, flavoring agents, and the like. In addition, there may also be included in the composition other active ingredients to provide a broader spectrum of antibiotic activity.

The dosage to be administered depends to a large extent upon the condition of the subject being treated and the weight of the host. The parenteral route being preferred for generalized infections and the oral route for intestinal infections. In general, a daily dosage consists of from about 15 to about 175 mg. of active ingredient per kg. of body weight of the subject in one or more applications per day. A preferred daily dosage for Antibiotic 810A of its individual components lies in the range of from about 20 to 40 mg. of active ingredient per kg. of body weight. The preferred daily dosage for antibiotic 842A is in the range of from about 40 to 80 mg. of active ingredient per kg. of body weight.

The instant compositions may be administered in several unit dosage forms as, for example, in solid or liquid orally ingestible dosage form. The compositions, per unit dosage, whether liquid or solid, will generally contain from about 15 mg. to about 700 mg. by weight of the active ingredient based upon the total of the compositions; however, in general, it is preferable to employ a dosage amount in the range of from about 80 mg. to 320 mg. In parenteral administration the unit dosage is usually the pure compound in a sterile water solution or in the form of a soluble powder intended for solution.

One typical unit dosage form consists in mixing 120 mg. of Antibiotic 810A or 120 mg. of one of its components or salt thereof, with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelation capsules and should it be necessary to mix more than 145 mg. of ingredients together, larger capsules may be employed. In a similar manner other unit dosages such as compressed tablets and pills can also be prepared. The following examples are illustrative:

| Dry-filled Capsule Containing 120 mg. of 7β-(D-5-amino-5-carboxyvaleramido)-3-(α-methoxy-p-sulfooxycinnamoyloxymethyl)-7-methoxy-3-cephem-4-carboxylic Acid (Ic) | |
|---|---|
| | Per Capsule |
| 7β-(D-5-amino-5-carboxyvaleramido)-3-(α-methoxy-p-sulfooxycinnamoyloxymethyl)-7-methoxy-3-cephem-4-carboxylic Acid (Ic) | 120 mg. |
| Lactose | 20 mg. |
| Magnesium Stearate | 5 mg. |
| Capsule Size No. 3 | 145 mg. |

The 7β-(D-5-amino-5-carboxyvaleramido)-3-(α-methoxy-p-sulfooxycinnamoyloxymethyl)-7-methoxy-3-cephem-4-carboxylic acid (Ic) is reduced to a No. 60 powder and then lactose and magnesium stearate are passed through a No. 60 bolting cloth onto the powder and the combined ingredients admixed for 10 minutes and then filled into No. 3 dry gelation capsules. By substituting 40 mg. of Antibiotic 842A and 100 mg. of lactose for the 120 mg. of active ingredient and 20 mg. of lactose recited in the foregoing formulation, there is thus obtained a 145 mg. capsule which is also suitable for oral administration.

| Tablet Containing 250 mg. of 7β-(D-5-amino-5-carboxyvaleramido)-3-(α-methoxy-p-sulfooxycinnamoyloxymethyl)-7-methoxy-3-cephem-4-carboxylic Acid (Ic) | |
|---|---|
| | Per Tablet |
| 7β-(D-5-amino-5-carboxyvaleramido)-3-(α-methoxy-p-sulfooxycinnamoyl-oxymethyl)-7-methoxy-3-cephem-4-carboxylic Acid (Ic) | 150 mg. |
| Dicalcium Phosphate, U.S.P. | 192 mg. |
| Magnesium Stearate | 5 mg. |
| Lactose, U.S.P. | 65 mg. |

The active component is blended with the dicalcium phosphate and lactose. The mixture is granulated with 15% cornstarch paste (6 mg.) and rough-screened. It is dried at 45° C. and screened again through a No. 16 screen. The magnesium stearate is added and the mixture is compressed into tablets approximately 0.5 inch in diameter.

| Tablet Containing 7β-(D-5-amino-5-carboxyvaleramido)-3-(carbamoyloxymethyl)-7-methoxy-3-cephem-4-carboxylic Acid (Ib) | |
|---|---|
| | Per Tablet |
| 7β-(D-5-amino-5-carboxyvaleramido)-3-(carbamoyloxymethyl)-7-methoxy-3-cephem-4-carboxylic Acid (Ib) | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| Parenteral Solution Containing 500 mg. of 7β-(D-5-amino-5-carboxyvaleramido)-3-(α-methoxy-p-sulfooxycinnamoyloxymethyl)-7-methoxy-3-cephem-4-carboxylic Acid (Ic) | |
|---|---|
| Ampoule: | |
| 7β-(D-5-amino-5-carboxyvaleramido)-3-(α-methoxy-p-sulfooxycinnamoyloxymethyl)-7-methoxy-3-cephem-4-carboxylic Acid (Ic) | 500 mg. |
| Ampoule: | |
| Diluent: Sterile Water for Injection | 2 cc. |

The 7β-(D-5-amino-5-carboxyvaleramido)-3-(α-methoxy-p-sulfooxycinnamoyloxymethyl)-7-methoxy-3-cephem-4-carboxylic acid (Ic) may be administered alone or in combination with other biologically active ingredients as, for example, with other antibacterial agents such as lincomycin, a penicillin, streptomycin, novobiocin, gentamicin, neomycin, colistin and kanamycin.

By substituting an equivalent amount of 7β-(D-5-amino-5-carboxyvaleramido)-3-(carbamoyloxymethyl)-7-methoxy-3-cephem-4-carboxylic acid (Ib) for the 500 mg. of 7β-(D-5-amino-5-carboxyvaleramido)-3-(α-methoxy-p-sulfooxycinnamoyloxymethyl)-7-methoxy-3-cephem-4-carboxylic acid (Ic) recited in the foregoing formulation, there is also obtained a formulation suitable for parenteral administration.

SYNTHETIC METHODS

In addition to the above-described fermentation products this invention includes derivatives in which the 3-carbamoyloxy moiety of 842A is replaced by a wide variety of substituents. In general, this replacement or substitution is effected by simply treating 842A with a reagent capable of converting the 3-carbamoyloxy moiety to the desired R substituent (see Formula I, supra). However, in practice, prior to the replacement of the 3-carbamoyloxy radical, it is frequently necessary to 'protect' the free amino and carboxy groups by treating 842A with a nitrogen-blocking agent such as a N-lower alkoxycarbonylphthalimide and an esterifying agent so as to afford the corresponding 7β-(D-5-phthaloylamino-5-carboxyvaleramido)-3-(carbamoyloxymethyl)-7-methoxy-3-cephem-4-carboxylic acid diester (Compound II, infra). Suitable esterifying agents include phenyldiazomethane or diphenyldiazomethane and the like. Also, other nitrogen-blocking agents which may be used in lieu of the N-lower alkoxycarbonylphthalimide include tertiary-butyloxyazide or trihaloethoxycarbonyl halides such as trichloroethyoxycarbonyl chloride and the like. The following equation wherein the nitrogen-blocking agent is an N-lower alkoxycarbonylphthalimide illustrates this reaction; however, it is to be understood that other nitrogen-blocking agents such as mentioned above may be substituted therefor in an otherwise similar reaction to afford the corresponding N-substituted derivative:

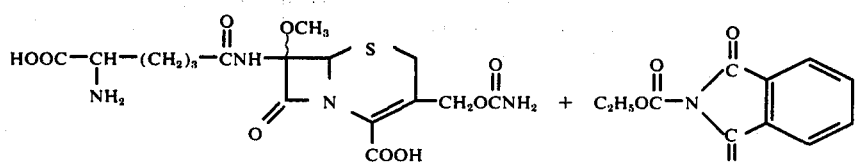

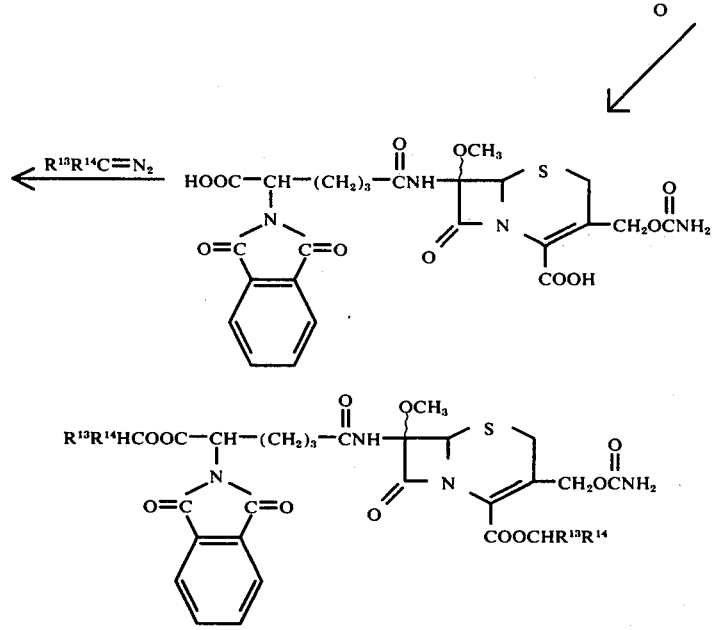

wherein $R^{13}R^{14}C=N_2$ is diazomethane or an aryl substituted diazomethane such as phenyldiazomethane or diphenyldiazomethane and the like and $R^{13}$ and $R^{14}$ are hydrogen or phenyl. The Compound (II) thus obtained is the starting material in the following synthetic methods.

The 3-hydroxymethyl analog of 842A is obtained by treating Compound II, supra, with a nitrosyl halide such as nitrosyl chloride in a suitable solvent such as methylene chloride. The following equation illustrates this method of preparation:

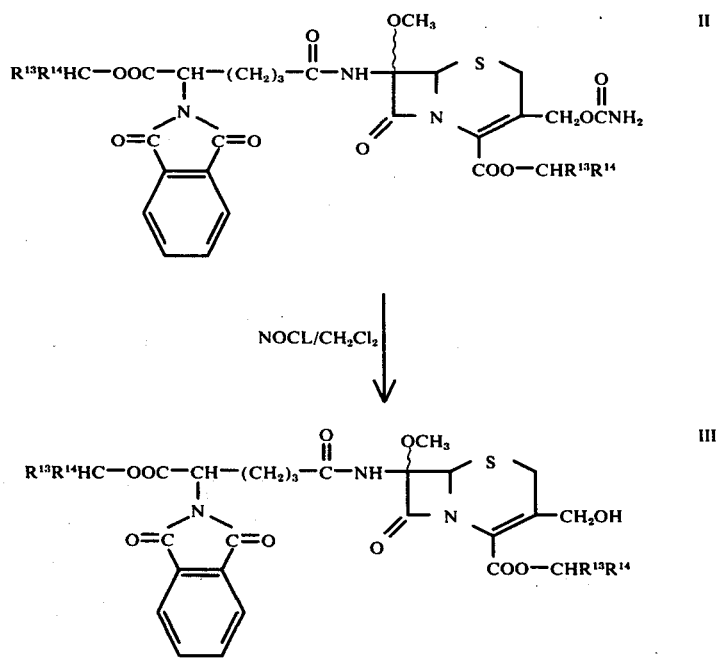

wherein $R^{13}$ and $R^{14}$ are as defined above. The diester thus obtained, preferably the di-benzhydryl ester (IIIa, infra), can then be converted to the corresponding free amino-acid (IV, infra) via acid hydrolysis and treatment with hydrazine hydrate in a basic solution. Deblocking by this method is most conveniently effected when the diester reactant is the dibenzhydryl ester (IIIa). The following equation illustrates this method of preparation:

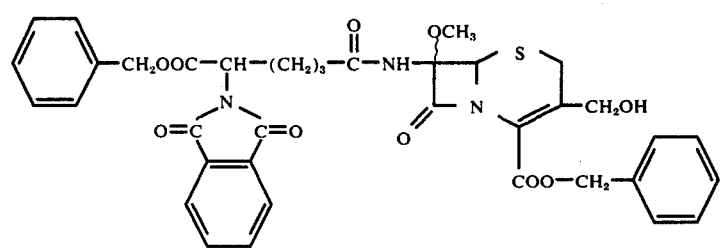

IIIa

↓ HPd

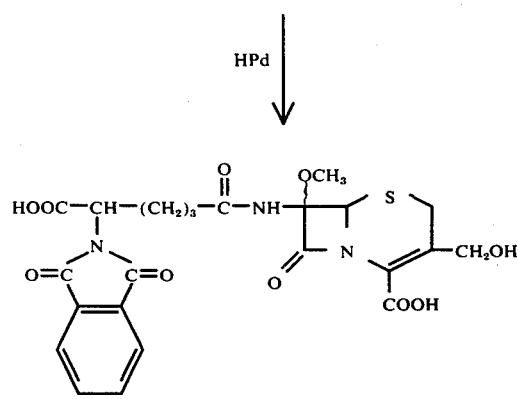

↓ NH₂NH₂.H₂O | Base

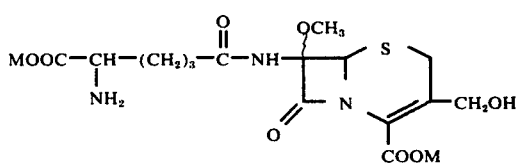

IV and M is the cation derived from an alkali metal or alkaline earth metal.

Compound IV in the preceding paragraph can be converted to its corresponding lactone by treating same or its corresponding mono-salt, with an acid. Suitable acids include any strong or weak organic or inorganic acid such as hydrochloric acid, sulfuric acid, nitric acid, para-toluenesulfuric acid, benzenesulfonic acid, aqueous acetic acid, sodium dihydrogenphosphate or a weakly acidic (aqueous) solution of mineral acid. Also, in practice, it is sometimes advantageous to employ a neutralizing agent such as sodium acetate trihydrate to neutralize any excess acid in the reaction mixture and thus avoid the formation of an acid salt with the free amino moiety. The following equation, wherein the hydroxymethyl analog of 842A is in the form of its mono salt, illustrates this method of preparation:

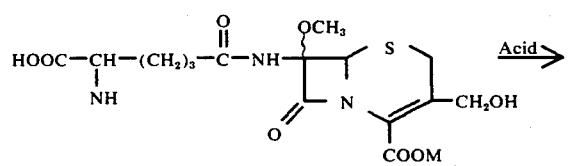

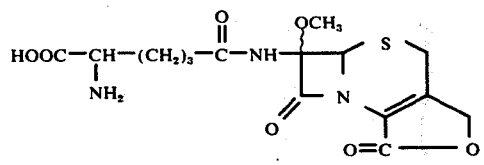

wherein M is as defined above.

The N-mono-substituted and N,N-di-substituted 3-carbamoyloxy analogs of 842A are conveniently obtained by by treating the diester of 7β-(D-5-phthaloylamino-5-carboxyvaleramido)-3-(hydroxymethyl)-7-methoxy-3-cephem-4-carboxylic acid, preferably in the form of its dibenzhydryl ester (IIIb, infra), with a carbonyl halide such as carbonyl chloride (i.e., phosgene) or carbonyl bromide, followed by the reaction of the dibenzhydryl ester of 7β-(D-5-phthaloylamino-5-carboxyvaleramido)-3-(haloformyloxymethyl)-7-methoxy-3-cephem-4-carboxylic acid (V, infra) thus obtained with the appropriate mono-lower alkylamine, di-lower alkylamine or heterocyclic amine:

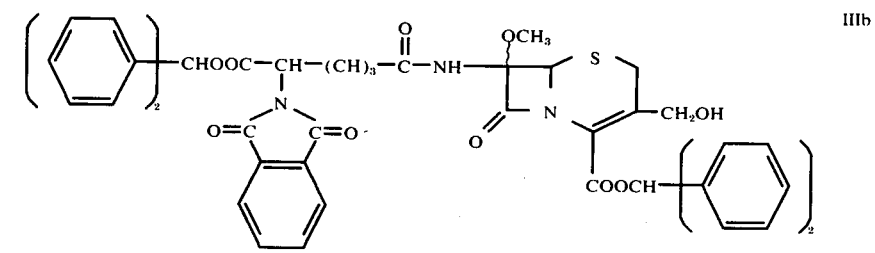

IIIb

↓ COX₂

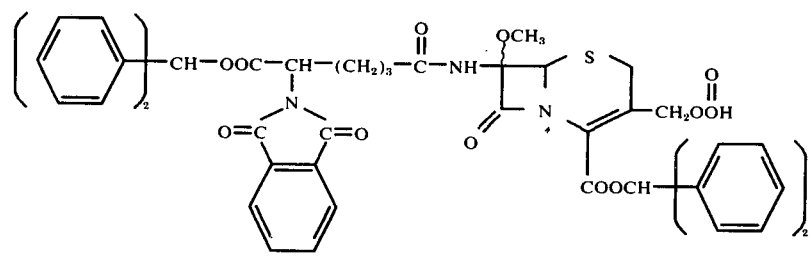

V

↓ HNR¹⁵R¹⁶

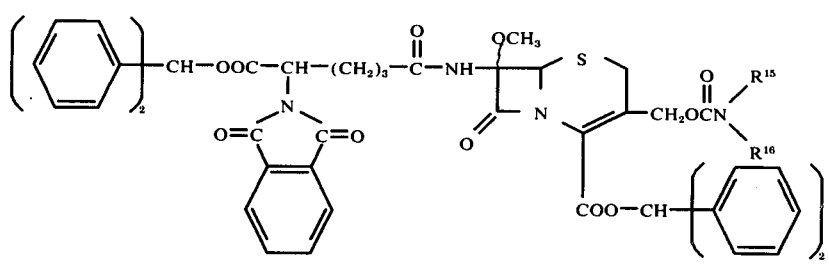

VI wherein COX₂ is a carbonyl halide such as carbonyl chloride (i.e., phosgene) or carbonyl bormide and X is halo as, for example, chloro, bromo and the like, HNR¹⁵R₁₆ is a primary or secondary amine selected from mono-lower alkylamines, di-lower alkylamines and heterocyclic amines and R¹⁵ and R¹⁶ represent lower alkyl such as methyl, ethyl, n-propyl, n-butyl and the like and, taken together R¹⁵ and R¹⁶ may be combined with the nitrogen atom to which they are attached to afford a mononuclear heterocyclic amine selected from pyrrolidine, piperidine and morpholine. The product (VI) thus obtained may then be converted to the corresponding free amino-acid by treatment with trifluoroacetic acid in xylene and then with hydrazine hydrate in a basic solution:

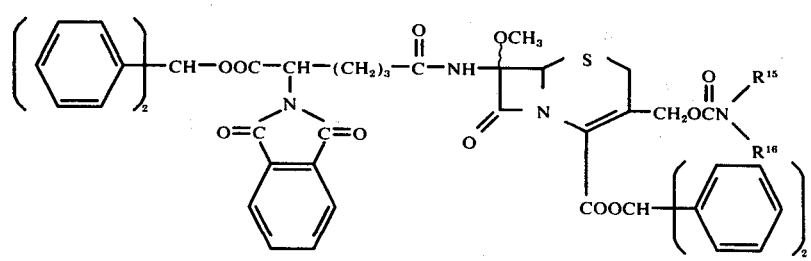

VI

↓ HOOCCF₃

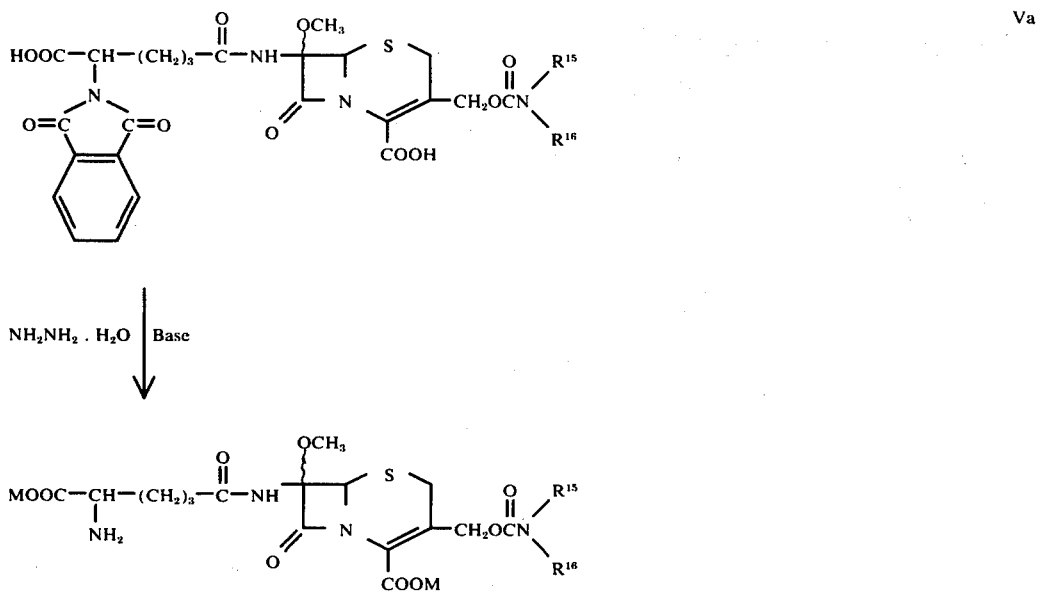

Va

NH₂NH₂ . H₂O | Base wherein M and $R^{15}$ and $R^{16}$ are as defined above.

Another method for preparing the N-mono-substituted derivatives of 842A consists in treating the compound III, infra, or a di-salt thereof, with an appropriate isocyanate. This reaction is most advantageously conducted in the presence of a strong organic base such as triethylamine and in the presence of an inert solvent such as dimethylformamide, methylene chloride, tetrahydrofuran or acetonitrile:

are, for example, methylisocyanate, ethylisocyanate, tertiary-butylisocyanate, chloromethylisocyanate, β-chloroethylisocyanate, carbethoxyisocyanate, phenylisocyanate and benzhydrylisocyanate. The products obtained by this method may then be converted to the corresponding free amino-acid via the method previously described, i.e., by treatment with trifluoroacetic acid in xylene followed by the reaction of the resulting intermediate with hydrazine hydrate in basic solution.

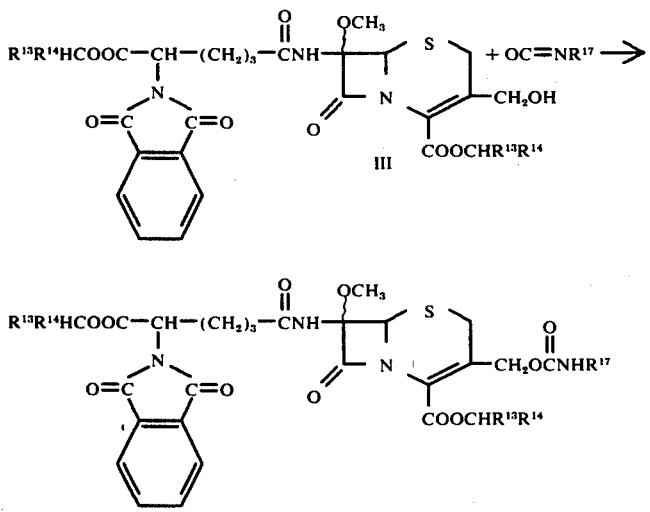

wherein $R^{17}$ is lower alkyl, halo substituted lower alkyl such as chloromethyl, 2-chloroethyl or chloro-tertiarybutyl and the like, lower alkoxycarbonyl such as ethoxycarbonyl and the like, mono-nuclear and bi-nuclear aryl such as phenyl, naphthyl and the like, mono-nuclear alkarylsulfonyl such as p-tolysulfonyl and the like or benzhydryl. Typical of the isocyanate reactants (i.e., OC—$NR^{17}$) which may be employed The 3-acylated derivatives of this invention corresponding to Formula I wherein R is lower alkanoyloxy, aromatic-carbonyloxy, aralkanoyloxy or cycloalkane-carbonyloxy are conveniently obtained by treating the dibenzhydryl ester of 7β-(D-5-phthaloylamino-5-carboxyvaleramido)-3-(hydroxy-methyl)-7-methoxy-3-cephem-4-carboxylic acid (IIIb) with a suitable acyl halide. The following equation illustrates this method of preparation:

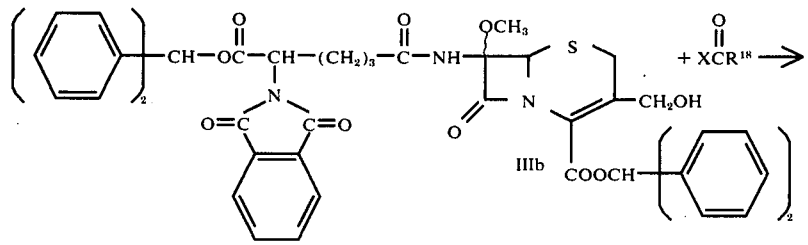

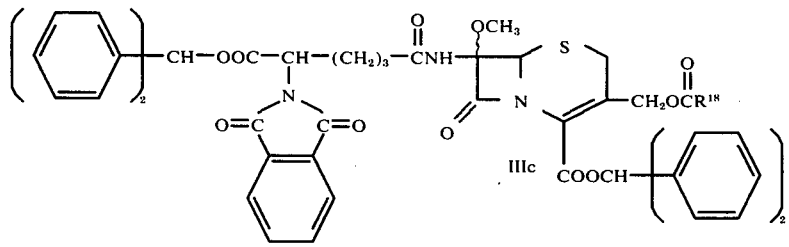

wherein $R^{18}$ is lower alkyl such as methyl, ethyl and the like, mono-nuclear and bi-nuclear aryl such as phenyl, naphthyl and the like, a mononuclear nitrogen-containing heterocycle such as 4-pyridyl and the like, mononuclear and binuclear lower aralkyl such as benzyl, phenethyl, menaphthyl and the like or cycloalkyl containing from 5–6 nuclear carbon atoms such as cyclopentyl or cyclohexyl and the like and X is as defined above. Again, the product thus obtained may be converted to the corresponding free amino-acid by treatment with trifluoroacetic acid in xylene followed by the reaction of the resulting intermediate with hydrazine hydrate in a basic solution.

The 3-methyl analogs of 842A are conveniently obtained via the reduction of 842A or a salt thereof as, for example, by the catalytic hydrogenation of the corresponding alkali metal or alkaline earth metal salt. Catalysts which may be used in this process include, for example, any of the metals in Group VIII of the Periodic Table as, for example, palladium, platinum or nickel. The following equation illustrates this method of pareparation:

carbamate, dithiocarboxylate, amine, pyridine, nuclear substituted pyridine, alkali-metal sulfinate, azide, polyhydroxybenzene or N-lower alkylindole. The resulting products can then be purified by conventional means as, for example, by recrystallization from suitable solvents such as methanol and water or by fractionation through a suitable ion-exchange resin.

In addition to the 3-acyloxymethyl analog of 842A it has be4n found that 842A may be employed per se as a starting material in the reaction with thiourea and alkali metal azides, etc. Thus, for example, 842A may be treated with the appropriate thiourea, N-substituted thiourea, N,N-disubstituted thiourea, alkali metal azide, thiazole, thiadiazole, halogenating agent or alkali metal thiocyanate to afford the corresponding 3-thiouroniummethyl, 3-azidomethyl, 3-thiazolylmercaptomethyl, 3-thiadiazolylmercaptomethyl, halomethyl and 3-thiocyanatomethyl analogs of 842A. In principle, it is only necessary to combine the starting materials to effect the synthesis but, in practice, it is usually desirable to catalyze the reaction by the application of heat as, for example, by heating at temperatures in the range

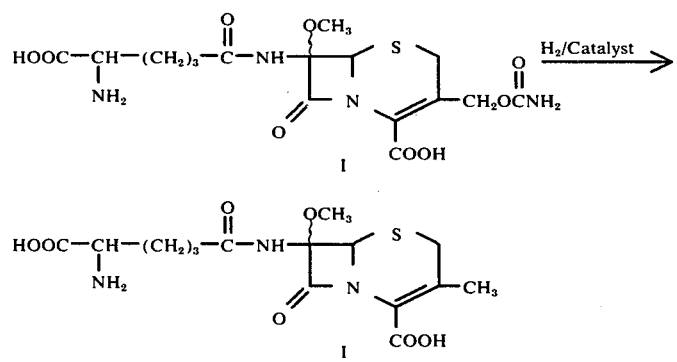

Those derivatives of 842A which are not prepared via the foregoing methods can be obtained by treating a 3-acyloxymethyl analog of 842A as, for example, the 3-lower alkanoyloxymethyl analog such as 7β-(D-5-amino-5-carboxyvaleramido)-3-(acetoxymethyl)-7-methoxy-3-cephem-4-carboxylic acid, with the appropriate thiourea or N-substituted thiourea, thiol, dithioof from about 45° C. to 95° C. for a period of from about 2.5 days to several minutes. A preferred operating temperature lies in the range of from about 75°–80° C. and good yields have also been obtained upon heating the reactants at 95° C. for about eight minutes. Also, in some instances, it is desirable to protect the free amino group in the 5-amino-5-carboxyvaleramido side chain of 842A by treating the latter with tertiarybutoxycarbonylazide or similar blocking group. The resulting 7β-(D-5-N-tertiarybutoxycarbonylamino-5-carboxyvaleramido)-3-(carbamoyloxymethyl)-7-methoxy-3-cephem-4-carboxylic acid can then be treated with the appropriate thiourea, alkali metal azide, thiazole, thiadiazole, halogenating agent or thiocyanate reactant so as to introduce the desired substituent into the 3-position of the 842A nucleus without the risk of any untoward side reactions. The intermediate thus obtained can then be deblocked via treatment with a suitable reagent such as trifluoroacetic acid, to obtain the desired product.

The 3-azidomethyl derivative of 842A obtained via the foregoing method is converted to its corresponding 3-aminomethyl analog by reduction. Suitable means include, for example, molecular reduction and hydrogenation over a suitable metal catalyst such as the metals in Group VIII of the Periodic System. Typical of the metals which may be employed include, for example, platinum, palladium and nickel and combinations thereof.

The molecular reduction of the 3-azidomethyl derivative is most advantageously conducted by adding zinc dust to an acidic solution of the 3-azidomethyl reactant. The resulting solution is then treated with hydrogen sulfide or an equivalent material to remove the soluble zinc from the solution in the form of a precipitate. The product thus obtained is the substantially pure 3-aminomethyl analog of 842A.

The products of this invention (I) form a wide variety of pharmacologically acceptable salts with inorganic and organic bases; these include, for example, metal salts such as are derived from alkali metal and alkaline earth metal hydroxides, carbonates and bicarbonates and salts derived from primary, secondary, and tertiary amines such as monoalkylamines, dialkylamines, trialkylamines, lower alkanolamines, di-lower alkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples of these salts include salts derived from sodium hydroxide, sodium carbonate, sodium bicarbonate, potassium carbonate, potassium hydroxide, calcium carbonate and the like and salts derived from such amines as trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline and N-methylglucamine and the like.

The aforementioned salts can be mono-salts such as the monosodium salt obtained, for example, by treating one equivalent of sodium or calcium hydroxide with one equivalent of product (I), or mixed di-salts obtained by treating one equivalent of the mono-salt with one equivalent of a different base. Alternatively, the said di-salts can be obtained by treatment with two equivalents of a base such as sodium hydroxide or calcium hydroxide with one equivalent of the said product (I). In addition, mixed salts and esters such as those obtained by treating the product (I) with one equivalent of sodium hydroxide and then with one equivalent of lactic acid are also contemplated.

The salts of this invention are pharmacologically acceptable nontoxic derivatives which can be used as the active ingredient in suitable unit-dosage pharmaceutical forms. Also, they may be combined with other drugs to provide compositions having a broad spectrum of activity. In addition, the instant salts and, also, the corresponding ester and amide derivatives, have utility as intermediates in preparing the carboxylic acid product illustrated by formula I, supra. And too, the said salts may be used to prepare other pharmaceutically acceptable salts.

In addition to salts the instant products (I) may also be converted to their corresponding mono- and diesters and mono- and diamides as, for example, the pivaloyloxymethyl or dibenzhydryl esters or alkyl, cycloalkyl, aryl or aralkyl esters as, for example, the methyl, ethyl, cyclohexyl, phenyl and benzyl esters or amides, diamides, N-lower alkyl amides, N,N-di-lower alkylamides, N-aralkylamides, N,N-diaralkylamides or heterocyclic amides such as the N-methyl and N-ethylamide, N,N-dimethylamide, N,N-diethylamide, N-benzylamide, N,N-dibenzylamide, piperidide, pyrrolidide or morpholide and the like.

Methods for the preparation of the aforementioned esters and amide derivatives include the reaction of the carboxylic acid product (I) or corresponding acid halide with methanol, ethanol, cyclohexanol, phenol, benzylalcohol or dibenzhydrol. In a similar manner the amide derivatives may be obtained by treating the corresponding acid halide with ammonia or with the appropriate alkylamine, dialkylamine, aralkylamine or heterocyclic amine. These and other conventional methods for the preparation of the said esters and amides will be obvious to those skilled in the art.

The examples which follow illustrate the methods by which the products of this invention may be obtained. However, the examples are illustrative only and it should be apparent to those having ordinary skill in the art that this invention includes other functionally equivalent products and methods for their preparation. Therefore, any modification of this synthesis which results in the formation of an identical product should be construed as constituting an analogous method. The claimed process is capable of wide variation and modification and, therefore, any minor departure therefrom or extension thereof is considered as being within the skill or the artisan and as falling within the scope of this invention.

EXAMPLE 1

Antibiotic 810A

A lyophilized tube of *Streptomyces griseus* culture (MA-2837) was opened aseptically. The contents were used to inoculate four slants of a nutrient medium having the following composition:

| Medium I: | | |
|---|---|---|
| Difco Yeast Extract | 10.0 | g. |
| Glucose | 10.0 | g. |
| *Phosphate Buffer | 2.0 | ml. |
| MgSO$_4$ . 7H$_2$O | 0.05 | g. |
| Distilled Water | 1000.0 | ml. |
| Difco Agar | 25.0 | g. |
| *Phosphate Buffer: | | |
| KH$_2$PO$_4$ | 91.0 | g. |
| Na$_2$HPO$_4$ | 95.0 | g. |
| Distilled Water | 1000.0 | ml. |

The slants were prepared by dispensing 14 ml./22 × 75 mm. culture tube. The tube was then stoppered with cotton, heated at 120° C. for 15 minutes to effect sterilization and the medium allowed to solidify in a slanted position. The inoculated slants were incubated at 28° C. for one week and then stored at 4° C. until used. The culture on one of these slants was then used to inoculate baffled Erlenmeyer flasks (250 ml.) containing 50 ml. of Medium II, infra, by the addition of 5 ml. of sterile medium, scraping the slant surface to suspend the growth and aseptically pipetting 1 ml. into each of three seed flasks. Medium II has the following composition:

| Medium II: | | |
|---|---|---|
| Beef Extract | 3.0 | g. |
| *NZ Amine | 10.0 | g. |
| Dextrose | 10.0 | g. |
| NaCl | 5.0 | g. |
| Distilled Water | 1000.0 | ml. |
| pH adjusted to 7.2 with NaOH | | |

*An enzymatic digested casein

The seed flask was shaken on a 220 rpm. rotary shaker with a 2 inch throw for three days. The seed flask culture was then used to inoculate 11 two-liter baffled Erlenmeyer flasks each containing 350 ml. of Medium III using a 2–3% inoculum. Medium III has the following composition:

| Medium III: | | |
|---|---|---|
| Dextrose | 10.0 | g. |
| Asparagine | 1.0 | g. |
| $K_2HPO_4$ | 0.1 | g. |
| $MgSO_4 \cdot 7H_2O$ | 0.5 | g. |
| Yeast Extract | 0.5 | g. |
| *Trace Element Mix No. 2 | 10.0 | ml. |
| Distilled Water | 1000.0 | ml. |
| pH adjusted to 7.2 with NaOH | | |
| *Trace Element Mix No. 2: | | |
| $FeSO_4 \cdot 7H_2O$ | 1.0 | g. |
| $MnSO_4 \cdot H_2O$ | 1.0 | g. |
| $CuCl_2 \cdot 2H_2O$ | 25.0 | mg. |
| $CaCl_2$ | 100.0 | mg. |
| $H_3BO_3$ | 56.0 | mg. |
| $(NH_4)_6MO_7O_{24} \cdot 4H_2O$ | 19.0 | mg. |
| $ZnSO_4 \cdot 7H_2O$ | 200.0 | mg. |
| Distilled Water | 1000.0 | ml. |

The flasks were then shaken on a 135–150 rpm. shaker with a 2 inch throw for four days at 28° C. At the end of the incubation period the contents of the eleven flasks were combined and assayed. The assay on the combined, centrifuged broth showed an inhibition zone of 22 mm. (½ inch discs) against Proteus vulgaris on a standard assay plate. This antibiotic was identified as 810A, that is, an antibiotic mixture comprising 7β-(D-5-amino-5-carboxyvaleramido)-3-(α-methoxy-p-sulfooxycinnamoyloxymethyl)-7-methoxy-3-cephem-4-carboxylic acid and 7β-(D-5-amino-5-carboxyvaleramido)-3-(α-methoxy-p-hydroxycinnamoyloxymethyl)-7-methoxy-3-cephem-4-carboxylic acid (Ia).

EXAMPLE 2

Antibiotic 810A

A lyophilized tube of Streptomyces griseus (MA-2837) was opened aseptically and the contents were used to inoculate the nutrient medium slants described as Medium I in Example 1. These slants were incubated at 28° C. for 1 week after which they were stored at 4° C. A portion of the culture on one of these slants was then used to inoculate a 250 ml. baffled Erlenmeyer seed flask containing 50 ml. of the medium described as Medium II in Example 1. This inoculated medium was incubated at 28° C. for two days on a 220 rpm. rotary shaker with a 2 inch throw. The inoculum was then washed aseptically by centifuging down the mycelia, pouring off the supernatant, resuspending in an equal volume of saline solution, re-centrifuging and again resuspending in a 0.9% sodium chloride solution. The washed mycelia was then used to inoculate (2% inoculum) two 250 ml. baffled Erlenmeyer flasks each containing 50 ml. of a chemically defined production medium which has been sterilized at 120° C. for 15 minutes. The chemically defined production medium has the following composition:

| Production Medium: | | |
|---|---|---|
| L-Proline | 15.0 | g. |
| Glycerol | 20.0 | g. |
| Sucrose | 2.5 | g. |
| Monosodium glutamate | 1.5 | g. |
| NaCl | 5.0 | g. |
| $K_2HPO_4$ | 2.0 | g. |
| $CaCl_2$ | 0.4 | g. |
| $MnCl_2 \cdot 4H_2O$ | 0.1 | g. |
| $FeCl_3 \cdot 6H_2O$ | 0.1 | g. |
| $ZnCl_2$ | 0.05 | g. |
| $MgSO_4 \cdot 7H_2O$ | 1.0 | g. |
| Distilled Water | 1000.0 | ml. |
| pH (unadjusted) 7.1 | | |

The production flasks were then shaken at 220 rpm. on a shaker with a two inch throw for four days at 28° C. Assays were run at three and four days. Samples were centrifuged and the supernatants assayed by the disc-Petri plate procedure. Using ½ inch discs these broths gave inhibition zones against Proteus vulgaris (MB-838) of 21 mm. after three days and 26 mm. after four days. The product was identified as Antibiotic 810A.

EXAMPLE 3

Antibiotic 810A

A lyophilized tube of Streptomyces griseus (MA-4125a; a natural subisolate of MA-2837) was opened aseptically and the contents transferred onto slants of the following composition:

| Medium IV: | | |
|---|---|---|
| V8 Juice | 100 | ml. |
| Staley's 4S-Soybean Meal | 20.0 | g. |
| Dextrose | 2.0 | g. |
| Agar | 25.0 | g. |
| Distilled Water | to 1000.0 | ml. |
| pH 7.9–8.0 | | |

The slants thus obtained were then used to inoculate several Erlenmeyer flasks (250 ml.) each containing 50 ml. of Medium V, infra.

| Medium V: | | |
|---|---|---|
| Yeast Autolysate (Ardamine) | 10.0 | g. |
| Glucose | 10.0 | g. |
| *Phosphate Buffer | 2.0 | ml. |
| $MgSO_4 \cdot 7H_2O$ | 0.05 | g. |
| Distilled Water | 1000.0 | ml. |
| pH - adjust to 6.5 using NaOH | | |
| *Phosphate Buffer Solution: | | |
| $KH_2PO_4$ | 91.0 | g. |

-continued

Medium V:

| | | |
|---|---|---|
| Na₂HPO₄ | 95.0 | g. |
| Distilled Water | 1000.0 | ml. |

The seed flasks were shaken for one day at 220 rpm. at 28° C.

The contents of the flasks were then used to inoculate 39 unbaffled Erlenmeyer flasks (250 ml.) containing 40 ml. of the Medium VI, infra; at 3.5 ml. of inoculum per flask.

Medium VI:

| | | |
|---|---|---|
| Corn Steep Liquor (wet basis) | 40.0 | g. |
| Dextrose | 20.0 | g. |
| NaCl | 2.5 | g. |
| MgSO₄ . 7H₂O | 0.5 | g./liter |
| Polyglycol 2000 | 0.25% | by volume (add to each flask individually) |
| Distilled Water | 1000.0 | ml. |
| pH - adjust to 7.0 with NaOH | | |

The production flasks were shaken on a rotary shaker with a 2-inch throw at 220 rpm. and at 24° C. for 40 hours after which time the flasks were pooled, an aliquot was taken for assay and the remainder delivered for extraction studies. The sample for assay was acidified to pH 4.0 using hydrochloric acid, filtered, diluted 1:4 in pH 5.0 phosphate buffer and placed onto *Proteus vulgaris* MB-838 plates using ½ inch discs. The zone of inhibition was 26.5 mm. The product was identified as Antibiotic 810A but primarily it consisted of 7β-(D-5-amino-5-carboxyvaleramido)-3-(α-methoxy-p-sulfooxycinnamoyloxymethyl)-7-methoxy-3-cephem-4-carboxylic acid with only trace amounts of 7β-(D-5-amino-5-carboxyvaleramido)-3-(α-methoxy-p-hydroxycinnamoyloxymethyl)-7-methoxy-3-cephem-4-carboxylic acid.

EXAMPLE 4

Antibiotic 810A

A V8 medium slant of the *Streptomyces griseus* culture (MA-4125a) was used to inoculate 50 ml. of Medium V in a 250 ml. baffled Erlenmeyer flask.

| Medium V: | | |
|---|---|---|
| Yeast Autolysate (Ardamine) | 10.0 | g. |
| Glucose | 10.0 | g. |
| *Phosphate Buffer | 2.0 | ml. |
| MgSO₄ . 7H₂O | 0.05 | g. |
| Distilled H₂O | 1000.0 | ml. |
| pH adjusted to 6.5 with NaOH | | |
| *Phosphate Buffer: | | |
| KH₂PO₄ | 91.0 | g. |
| Na₂HPO₄ | 95.0 | g. |
| Distilled H₂O | 1000.0 | ml. |

The flask was then shaken on a rotary shaker at 220 rpm. for 1 day at 28° C. Three ml. of this vegetative inoculum was used to inoculate a seed flask containing 50 ml. of the following synthetic medium (Medium VII) in a 250 ml. baffled Erlenmeyer flask.

| Medium VII: | Seed | Production |
|---|---|---|
| L-Asparagine | 5.0 g. | 5.0 g. |
| L-Histidine | 4.0 g. | 4.0 g. |
| DL-Phenylalanine | — | 2.0 g. |
| Monosodium glutamate | — | 1.5 g. |
| NaCl | 5.0 g. | 5.0 g. |
| K₂HPO₄ | 2.0 g. | 2.0 g. |
| CaCl₂ . 2H₂O | 0.4 g. | 0.4 g. |
| MnSO₄ . H₂O | 0.1 g. | 0.1 g. |
| FeSO₄ . 7H₂O | 0.1 g. | 0.1 g. |
| ZnSO₄ . 7H₂O | 0.05 g. | 0.05 g. |
| MgSO₄ . 7H₂O | 1.0 g. | 1.0 g. |
| Glycerol | 20.0 g. | 20.0 g. |
| Sucrose | 2.5 g. | 2.5 g. |
| Distilled H₂O | *1000.0 ml. | **1000.0 ml. |

*pH adjusted to 7.0 with NaOH
**pH adjusted to 7.1 with NaOH

The seed flask was again shaken at 220 rpm. for 1 day at 28° C. This synthetic seed was then used to inoculate several 250 ml. unbaffled Erlenmeyer flasks containing 38 ml. of Medium VII production, supra, at 1.5 ml. of inoculum per flask. The production flasks were shaken at 220 rpm. and 24° C. and their contents were then pooled and assayed at 4 and 5 days age. In the assay the whole broth was acidified to pH 4.0 using hydrochloric acid and the broth was then filtered and diluted 1:4 in pH 5.0 phosphate buffer. The assay was run on *Proteus vulgaris* MB-838 using 0.5 inch discs. An inhibition zone of 25.5 mm. was obtained with this fermentation broth after four days incubation and the product thus obtained was identified as 810A.

EXAMPLE 5

Preparation of Antibiotic 810A and Separation into Components

Step A: Fermentation

Stage 1: The contents of a lyophilized tube of *Streptomyces griseus* (MA-2837) was suspended in two ml. of Medium I (described in Example 1) and the resulting inoculum was used to inoculate slants of the same medium. These slants were incubated at 28° C. for five days or until well-sporulated and then ten ml. of Medium VIII, infra, was added to the slants.

| Medium VIII: | |
|---|---|
| Meat Extract | 0.3% |
| NaCl | 0.5% |
| NZ Amine | 1 % |
| Dextrose | 1 % |
| pH 7.0 | |

The growth on each slant was scraped into suspension and the suspension was used as the inoculum in Stage 2, infra.

Stage 2: The suspension obtained in Stage 1 was used to inoculate a 250 ml. baffled Erlenmeyer flask containing 50 ml. of sterilized Medium VII (described in Stage 1). The inoculated flask was then placed on a 220 rpm. rotary shaker and incubated for 48 hours at 28° C.

Stage 3: The contents of an inoculum flask from Stage 2 was used to inoculate a two-liter baffled Erlenmeyer flask containing 500 ml. of the medium identified as Medium VIII in Stage 1. The inoculated flask was then placed on a 220 rpm. rotary shaker and incubated for 48 hours at 28° C.

Stage 4: An inoculum of 500 ml. of the resulting growth from Stage 3 was used to inoculate a 200 gallon stainless steel fermentor containing 467 liters of a sterile Medium VIII (described in Stage 1). The fermentation was allowed to proceed at a temperature of 28° C. with agitation (130 rpm.) while maintaining an air flow of 10 cfm for 65 hours. During the fermentation an antifoam agent, Polyglycol 2000, was added in small quantities to prevent excessive foaming.

Stage 5: An inoculum of 100 gallons of the resulting growth from Stage 4 was used to inoculate a 1500 gallon stainless steel fermentor containing 1200 gallons of Medium IX, infra.

| Medium IX: | |
|---|---|
| Corn Steep Liquor | 4% |
| Dextrose | 3% |
| adjusted to 7.2 with NaOH | |

The fermentation was allowed to proceed at a temperature of 28° c. with agitation (120 rpm). While maintaining an air flow of 55.3 cfm for 30–36 hours. During the fermentation Polyglycol 2000 was added in small quantities to prevent excess foaming. The batch was harvested and activity was determined by disc-plate assay. Using 0.5 inch discs this broth gave an inhibition zone of 32.5 mm. against *Proteus vulgaris* MB-838 when harvested at 31 hours age.

Step B: Isolation of Antibiotic Mixture 810A

Filtered broth (1075 gal.) from Step A, Stage 5, was harvested after 36 hours and the pH adjusted from the range of 7–8 to 3.0 in the fermentor by the addition of phosphoric acid. The mycelia were removed by passage through a plate-screen type filter press and discarded. The filtered broth was then passed through a 100 gal. bed of Amberlite XAD-2 adsorbent resin at a flow rate of 10 gallons per minute. The spent broth was assayed and discarded and the resin bed was washed with two volumes of water. The antibiotic was eluted from the resin bed with a 60% solution of methanol and water at a flow rate of 5 gallons per minute. Forty fractions, each 5 gallons, were collected and assayed. Fractions 2 through 40 were combined and the methanol was removed by vacuum evaporation. The final concentrate (41.5 gal.) was adjusted to pH 3.5 by the addition of ammonium hydroxide and held frozen.

Samples were bio-assayed be the disc-plate method against *Proteus vulgaris*.

Filtered Broth: Assays run on 1060 gallons of filtered broth gave the following zone diameters.

| Filtered Broth | |
|---|---|
| Dilution | Zone Size |
| 1:2 | 26.8 mm. |
| 1:4 | 23.8 mm. |
| 1:8 | 21.1 mm. |

Spent Broth and Wash: Ten fractions of 100 gallons each assayed zero without dilution. The water wash assayed zero.

Eluate Fractions: Assays were run on all fractions. The zone diameters are tabulated below:

| Eluate Fractions | | | |
|---|---|---|---|
| Fraction | Zone Size | Fraction | Zone Size |
| 1 | 0 | 21 | 33 mm. |
| 2 | 28 mm. | 22 | 33 |
| 3 | 35 | 23 | 34 |
| 4 | 34 | 24 | 34 |
| 5 | 36 | 25 | 33 |
| 6 | 36 | 26 | 34 |
| 7 | 36 | 27 | 32 |
| 8 | 38 | 28 | 33 |
| 9 | 38 | 29 | 32 |
| 10 | 36 | 30 | 32 |
| 11 | 36 | 31 | 32 |
| 12 | 38 | 32 | 30 |
| 13 | 40 | 33 | 30 |
| 14 | 37 | 34 | 30 |
| 15 | 36 | 35 | 28 |
| 16 | 37 | 36 | 27 |
| 17 | 38 | 37 | 29 |
| 18 | 36 | 38 | 26 |
| 19 | 36 | 39 | 26 |
| 20 | 35 | 40 | 26 |

Eluate Composite and Eluate Concentrate: Assays were also run on 195 gallons of eluate composite and 41.5 gallons of Antibiotic 810A in the form of eluate concentrate.

| Eluate Composite | | Eluate Concentrate 810A | |
|---|---|---|---|
| Dilution | Zone Size | Dilution | Zone Size |
| 1:5 | 28.8 mm. | 1:16 | 17.25 mm. |
| 1:10 | 27.0 mm. | 1:32 | 14.5 mm. |
| 1:20 | 23.8 mm. | | |
| 1:40 | 21.0 mm. | | |

| Total Solid Assay: | |
|---|---|
| Filtered Broth | 119 kg. |
| 195 Gallon Eluate Composite | 7.23 kg. |
| 41.5 Gallon Eluate Concentrate | 7.20 kg. |

Step C: Adsorption on an Anion Exchange Resin

The concentrate from Step B (20.7 gal.) was diluted to 31 gallons with water and adsorbed on a 22.5 liter bed of weakly basic anion exchange resin (Amberlite IRA-68 resin on the chloride cycle) at pH 4.0 and a flow of 2 gallons per minute. This was followed by a 45 liter water wash whereafter te resin bed was eluted with a pH 7.5 solution of 1 M sodium nitrate and 0.1 M sodium acetate at a flow rate of 1.5 liters per minute. Ten five gallon eluate fractions were then collected and the pH adjusted to 4 with hydrochloric acid as collected.

All fractions were bio-assayed by the disc-plate method against *Proteus vulgaris* as follows:

| Feed Solution | | Eluate Fractions; Dilution 1:10 | | | |
|---|---|---|---|---|---|
| Dilution | Zone Size | Fraction | Zone Size | Fraction | Zone Size |
| 1:10 | 28.5 mm. | 1 | 27 mm. | 6 | 25 mm. |
| 1:20 | 26.5 mm. | 2 | 30 mm. | 7 | 23 mm. |
| 1:40 | 24 mm. | 3 | 28.5 mm. | 8 | 22 mm. |
| | | 4 | 26 mm. | 9 | 21 mm. |
| | | 5 | 26 mm. | 10 | 17.5 mm. |

The spent stream assayed 25 mm. without dilution and the water wash assayed 23 mm. without dilution.

Step D: Adsorption on a Non-Ionic Resin

Fractions 1 through 10 from Step C were combined and fed to a 45 liter bed of Amberlite XAD-2 adsorbent at pH 3.0 and at a flow rate of 5 liters per minute. The resin bed was washed with 90 liters of water at the same rate. The antibiotic was then eluted from the resin by a 25% solution of acetone and water at a flow rate of 5 liters per minute. Sixteen 5 gallon fractions were collected.

All fractions were assayed by disc-plate method against *Proteus vulgaris* as follows: the feed (190 liters) gave the following zone diameters:

| Feed Solution | |
|---|---|
| Dilution | Zone Size |
| 1:5 | 30 mm. |
| 1:10 | 27.5 mm. |
| 1:20 | 24.2 mm. |

The zone diameters of the eluate fractions are tabulated below:

| Fraction | Eluate Fraction Dilution | Zone Size | Fraction | Eluate Fraction Dilution | Zone Size |
|---|---|---|---|---|---|
| 1 | 1:10 | 20.5 mm. | 9 | 1:00 | 25 mm. |
| 2 | 1:10 | 29 mm. | 10 | 1:00 | 26.5 mm. |
| 3 | 1:10 | 29 mm. | 11 | 1:6 | 26 mm. |
| 4 | 1:10 | 29 mm. | 12 | 1:6 | 28 mm. |
| 5 | 1:10 | 28 mm. | 13 | 1:6 | 27.5 mm. |
| 6 | 1:10 | 27 mm. | 14 | 1:6 | 25 mm. |
| 7 | 1:10 | 26 mm. | 15 | 1:6 | 25 mm. |
| 8 | 1:10 | 26 mm. | 16 | 1:6 | 24.5 mm. |

The eluate fractions 2 through 16, supra, were combined and the acetone removed by vacuum evaporation to a final volume of 17.4 liters. The 17.4 liter concentrate was adjusted to pH 4.0 by ammonium hydroxide and freeze dried to yield 620 g. of Antibiotic 810A, i.e., a mixture consisting essentially of 7β-(D-5-amino-5-carboxyvaleramido)-3-(α-methoxy-p-sulfooxycinnamoylmethyl)-7-methoxy-3-cephem-4-carboxylic acid and 7β-(D-5-amino-5-carboxyvaleramido)-3-(α-methoxy-p-hydroxycinnamoyloxymethyl)-7-methoxy-3-cephem-4-carboxylic acid. This dry product had a bioassay potency of 320 mcg./ml. for a 25 mm. zone.

Step E: 7β-(D-5-amino-5-carboxylvaleramido)-3-(α-methoxy-p-hydroxycinnamoyloxymethyl)-7-methoxy-3-cephem-4-carboxylic Acid A one inch diameter chromatography column was packed to a bed height of 100 centimeters with DEAE Sephadex A-25 anion exchange resin in a system containing 0.5 M ammonium bromide and 0.05 M acetic acid. The mixture of Antibiotic 810A (10.0 g.) obtained in Step D was dissolved in 18 ml. of a solution of 0.5 M ammonium bromide and 0.05 M acetic acid and charged to the column. Eluting solution was pumped through the bed at a rate of 81 ml./hour and 10 ml. fractions of eluate were collected by machine. The eluate stream was monitored by a differential refractometer. The refractometer record showed mass peaks at tubes 19, 36, 79, 109 and 206. Disc plate assays against *Proteus vulgaris* (MB-838) were run on every third fraction using 0.5 inch diameter discs buffered at pH 7.0. The zone diameters are tabulated below: (Fractions 1 through 66 assayed zero).

| Fraction | Zone Diameter | Fraction | Zone Diameter | Fraction | Zone Diameter |
|---|---|---|---|---|---|
| 69 | 18 mm. | 122 | 29 | 204 | 40+ |
| 72 | 24 | 125 | 28 | 207 | 40+ |
| 75 | 26 | 128 | 27 | 210 | 40+ |
| 78 | 31 | 131 | 26 | 213 | 40+ |
| 81 | — | 134 | 24 | 216 | 40+ |
| 83 | 35 | 137 | 21 | 219 | 40 |
| 86 | 37 | 140 | 20 | 222 | 38 |
| 89 | 38 | 150 | 18 | 225 | 35 |
| 92 | 38 | 160 | 20 | 228 | 32 |
| 95 | 40+ | 170 | 29 | 231 | 31 |
| 98 | 40+ | 180 | 35 | 234 | 27 |
| 101 | 40+ | 183 | 38 | 237 | 24 |
| 104 | 40+ | 186 | 40 | 240 | 23 |
| 107 | 40+ | 189 | 40+ | 243 | 19 |
| 110 | 40+ | 192 | 40+ | 246 | 17 |
| 113 | 40 | 195 | 40+ | 249 | 0 |
| 116 | 38 | 198 | 40+ | 252 | 0 |
| 119 | 33 | 201 | 40+ | | |

Fractions 80 through 133 were combined and fractions 170 through 230 were combined.

A repeat of the above run was made and fractions 82–130 were combined and fractions 180–234 were combined.

The fractions containing the first active component from the two above runs were combined and adsorbed on a 100 ml. bed of Amberlite XAD-2 resin. The bed was washed with one volume of water and then eluted with three volumes of a 90% solution of methanol and water. The methanol was removed by vacuum evaporation and the aqueous concentrate was freeze dried to afford 810 mg. of a product identified as 7β-(D-5-amino-5-carboxyvaleramido)-3-(α-methoxy-p-hydroxycinnamoyloxymethyl)-7-methoxy-3-cephem-4-carboxylic acid. The bio-potency of this product determined by disc plate assay against *Proteus vulgaris* was 18 μg./ml. affording a 25 mm. zone. Analysis by ultraviolet adsorption gave the following characterizing data:

U.V. adsorption in 0.1 N HCL λmax. 305 $E_{1cm}^{\%}$ 524
U.V. adsorption in 0.1 N NaOH λmax. 328 $E_{1cm}^{\%}$ 564

Step F: 7β-(D-5-amino-5-carboxyvaleramido)-3-(α-methoxy-p-sulfooxycinnamoyloxymethyl)-7-methoxy-3-cephem-4-carboxylic Acid The fractions from the two runs on Sephadex A-25 containing the second active component were combined and adsorbed on a 100 ml. bed of Amberlite XAD-2 resin. The bed was washed with one volume of water and then eluted with three volumes of a 90% solution of methanol and water. The rich eluates were combined and methanol was removed by vacuum evaporation. The aqueous concentrate was freeze dried and yielded 720 mg. of 7β-(D-5-amino-5-carboxyvaleramido)-3-(α-methoxy-p-sulfooxycinnamoyloxymethyl)-7-methoxy-3-cephem-4-carboxylic acid (Ic).

Analysis by ultraviolet absorption gave the following characterizing data:

U.V. adsorption in 0.1 N HCl max. 287 mm. $E_{1cm.}^{\%}$ 432

U.V. adsorption in 0.1 N NaOH max. 280 mm. $E_{1cm.}^{\%}$ 432

EXAMPLE 6

Separation of 7β-(D-5-amino-5-carboxyvaleramido)-3-α-methoxy-p-sulfooxycinnamoyloxymethyl)-7-methoxy-3-cephem-4-carboxylic Acid from the Antibiotic Mixture 810A The antibiotic mixture 810A comprising 7β-(D-5-amino-5-carboxyvaleramido)-3-(α-methoxy-p-sulfooxycinnamoyloxymethyl)-7-methoxy-3-cephem-4-carboxylic acid (Ic) and 7β-(D-5-amino-5-carboxyvaleramide)-3-(α-methoxy-p-hydroxycinnamoyloxymethyl)-7-methoxy-3-cephem-4-carboxylic acid (20.0 g.) from Example 5, Step D, was dissolved in water (200 ml.) and the pH of the solution adjusted to 3.5. This solution was passed thru a 200 ml. bed of Amberlite IRA-68 anion exchange resin on the chloride cycle followed by the addition of 300 ml. of water wash. The bed was then eluted with 1 liter of 1% (v/v) formic acid in water. This was followed by the addition of two portions of dilute hydrochloric acid pH 0.95. The fed solution, spent and wash, and eluates 1, 2 and 3 were analyzed by paper electrophoresis at pH 4.0 run one hour at 1,000 volts D.C. The papergram was dried, exposed to ammonia vapor to neutralize acid and incubated on a nutrient agar plate seeded with Proteus vulgaris (MB-838). Examination after 17 hours incubation at 37° C. showed two zones of inhibition in the feed material (in the direction of the anode), only a single component (slower of the two) in the spent and formic acid eluates and a single component in the second hydrochloric acid eluate corresponding with the faster component in the feed. The following table indicates total-solid and bio-assay data:

|  | Mass | Volume | Total Biological Units | Product (s) |
|---|---|---|---|---|
| Feed | 20 g. | 200 ml. | 60,000 units | Ia |
| Spent & Wash | 11.15 g. | 500 ml. | 7,500 units | — |
| Formic Acid Eluate | 4.52 g. | 1000 ml. | 20,000 units | — |
| 1st Hydrochloric Acid Eluate | — | 500 ml. | 1,000 units | — |
| 2nd Hydrochloric Acid Eluate | 2.10 g. | 500 ml. | 10,000 units | Ic |

The last fractions were recovered by adsorption on Amberlite XAD-2 resin to separate out 7β-(D-5-amino-5-carboxyvaleramido)-3-(α-methoxy-p-sulfooxycinnamoyloxymethyl)-7-methoxy-3-cephem-4-carboxylic acid (Ic) and this was eluted by a 50% solution of methanol and water to afford substantially pure product (Ic).

EXAMPLE 7

Separation of 7β-(D-5-amino-5-carboxyvaleramido)-3-(α-methoxy-p-sulfooxycinnamoyloxymethyl)-7-methoxy-3-cephem-4-carboxylic Acid from Antibiotic 810A The Antibiotic 810A mixture of 7β-(D-5-amino-5-carboxyvaleramido)-3-(α-methoxy-p-sulfooxycinnamoyloxymethyl)-7-methoxy-3-cephem-4-carboxylic acid (Ic) and 7β-(D-amino-5-carboxyvaleramido)-3-(α-methoxy-p-hydroxycinnamoyloxymethyl)-7-methoxy-3-cephem-4-carboxylic acid (5.0 g.) obtained according to Example 5, Step D, was dissolved in a 20% solution of acetone and water (20 ml.) and the pH adjusted to 4.0. This solution was fed to a 2 inch diameter × 100 cm. height bed of Amberlite XAD-2 adsorbent in 20% acetone and water solution. A solution of 20% acetone and water was pumped through the bed at a rate of 880 ml./hour and 20 ml. fractions were collected automatically.

Disc plate assays against Proteus vulgaris (MB-838) were run on every third fraction using 0.25 inch discs. The zone diameters are tabulated below:

| Fraction | Zone Diameter | Fraction | Zone Diameter | Fraction | Zone Diameter |
|---|---|---|---|---|---|
| 1–41 | 0 | 131 | 0 | 221 | 18 |
| 44 | 12 mm. | 134 | 0 | 224 | 18 |
| 47 | 22 | 137 | 0 | 227 | 18 |
| 50 | 25 | 140 | 8 | 230 | 17 |
| 53 | 29 | 143 | 11 | 233 | 17 |
| 56 | 31 | 146 | 13 | 236 | 15 |
| 59 | 35 | 149 | 13 | 239 | 15 |
| 62 | 30 | 152 | 15 | 242 | 15 |
| 65 | 28 | 155 | 15 | 245 | 15 |
| 68 | 27 | 158 | 16 | 248 | 14 |
| 71 | 25 | 161 | 17 | 251 | 14 |
| 74 | 24 | 164 | 18 | 254 | 14 |
| 77 | 21 | 167 | 17 | 257 | 13 |
| 80 | 20 | 170 | 18 | 260 | 13 |
| 83 | 19 | 173 | 20 | 263 | 12 |
| 86 | 16 | 176 | 21 | 266 | 12 |
| 89 | 14 | 179 | 21 | 269 | 12 |
| 92 | 13 | 182 | 21 | 272 | 11 |
| 95 | 13 | 185 | 21 | 275 | 11 |
| 98 | 13 | 188 | 22 | 278 | 10 |
| 101 | 13 | 191 | 23 | 281 | 10 |
| 104 | 14 | 194 | 23 | 284 | 9 |
| 107 | 13 | 197 | 23 | 287 | 8 |
| 110 | 13 | 200 | 22 | 290 | 0 |
| 113 | 11 | 203 | 24 | 293 | 0 |
| 116 | 10 | 206 | 24 | 296 | 0 |
| 119 | 9 | 209 | 24 | 299 | 0 |
| 122 | 8 | 212 | 24 | 302 | 0 |
| 125 | 8 | 215 | 24 |  |  |
| 128 | 8 | 218 | 19 | 330 | zero |

Fractions 44 through 90 were combined, acetone was removed by vacuum evaporation and the aqueous concentrate was freeze dried to yield 3.3 g. of crude 7β-(D-5-amino-5-carboxyvaleramido)-3-(α-methoxy-p-sulfooxycinnamoyloxymethyl)-7-methoxy-3-cephem-4-carboxylic acid (Ic).

Fractions 150 through 225 were combined and by similar treatment afforded 700 mg. of 7β-(D-5-amino-5-carboxyvaleramido)-3-(α-methoxy-p-hydroxycinnamoyloxymethyl)-7-methoxy-3-cephem-4-carboxylic acid.

A repeat of the above run afforded 3.1 g. of crude 7β-(D-amino-5-carboxyvaleramido)-3-(α-methoxy-p-sulfooxycinnamoyloxymethyl)-7-methoxy-3-cephem-4-carboxylic acid (Ic) and 400 mg. of 7β-(D-5-amino-5-carboxyvaleramido)-3-(α-methoxy-p-hydroxycinnamoyloxymethyl)-7-methoxy-3-cephem-4-carboxylic acid.

The two quantities of 7β-(D-5-amino-5-carboxyvaleramido)-3-(α-methoxy-p-sulfooxycinnamoyloxymethyl)-7-methoxy-3-cephem-4-carboxylic acid (Ic) obtained according to the foregoing method were combined and the 6.4 g. of material was charged to a 2 inch diameter × 100 cm. height bed of Amberlite XAD-2 adsorbent in a 5% solution of methanol and water. A 5% methanol and water solution was pumped through the bed at a flow rate of 880 ml./hour and 20 ml. fractions were collected automatically. Two hundred and eighty-seven fractions were collected and every fourth fraction was assayed by the disc-plate method against *Proteus vulgaris* (MB-838) using 0.25 inch discs. The assay results are tabulated below. Fractions 1 through 50 were not assayed.

| Fraction | Zone Size | Fraction | Zone Size |
|---|---|---|---|
| 51 | 23 mm. | 115 | 20 |
| 55 | 26 | 119 | 20 |
| 59 | 23 | 123 | 19 |
| 63 | 18 | 127 | 18 |
| 67 | 12 | 131 | 19 |
| 71 | 0 | 155 | 16 |
| 75 | 0 | 139 | 17 |
| 79 | 0 | 143 | 15 |
| 83 | 7 | 147 | 16 |
| 87 | 9 | 151 | 15 |
| 91 | 13 | 155 | 13 |
| 95 | 19 | 159 | 11 |
| 99 | 21 | 163 | 9 |
| 103 | 22 | 167 | 0 |
| 107 | 22 | 171 | 0 |
| 111 | 21 | 287 | zero |

Fractions 95 through 159 were combined, methanol vacuum evaporated, and the aqueous concentrate freeze dried to yield 700 mg. of 7β-(D-5-amino-5-carboxyvaleramido)-3-(α-methoxy-p-sulfooxycinnamoyloxymethyl)-7-methoxy-3-cephem-4-carboxylic acid (Ic). The ultra violet spectra of 7β-(D-5-amino-5-carboxyvaleramido)-3-(α-methoxy-p-sulfooxycinnamoyloxymethyl)-7-methoxy-3-cephem-4-carboxylic acid (Ic) gave the following adsorption data:

U.V. adsorption in 0.1 N HCl max. 285 $E_{1cm.}^{\%}$ 160
U.V. adsorption in 0.1 N NaOH max. 277 $E_{1cm.}$ 166

When assayed with 0.5 inch diameter discs by the disc-plate method against *Proteus vulgaris* the 7β-(D-5-amino-5-carboxyvaleramido)-3-(α-methoxy-p-sulfooxycinnamoyloxymethyl)-7-methoxy-3-cephem-4-carboxylic acid (Ic) sample gave a 25 mm. zone at 88 mcg./ml. and 7β-(D-5-amino-5-carboxyvaleramido)-3-(α-methoxy-p-hydroxycinnamoyloxymethyl)-7-methoxy-3-cephem-4-carboxylic acid gave a 25 mm. zone at 167 mcg./ml..

EXAMPLE 8

Antibiotic 842A

Step A: Shake Flask Production

A lyophilized tube of *Streptomyces lactamdurans* culture (MA-2908) was opened asceptically. The tube was then used to inoculate a 250 ml. baffled Erlenmeyer flask containing 50 ml. of nutrient Medium V by breaking the tube in sterile gauze and transferring the pellet asceptically into the flask. The Medium V has the following composition:

| Medium V: | | |
|---|---|---|
| Yeast Autolysate (Ardamine) | 10.0 | g. |
| Glucose | 10.0 | g. |

-continued

| Medium V: | | |
|---|---|---|
| *Phosphate Buffer | 2.0 | ml. |
| MgSo₄ . 7H₂O | 1.05 | g. |
| Distilled Water | 1000.0 | ml. |
| pH 6.5 | | |
| *Phosphate Buffer* | | |
| KH₂PO₄ | 91.0 | g. |
| Na₂HPO₄ | 95.0 | g. |
| Distilled Water | 1000.0 | ml. |

This seed flask was shaken at 28° C. on a 220 rpm. rotary shaker with a two inch throw for 3 days. Five ml. aliquots (10% inoculum of this growth were then transferred, using sterile pipettes, to four second-stage seed flasks of the same size and containing the same medium as described above and these flasks were then shaken in the manner indicated above. The second-stage seed flasks were then pooled asceptically into one flask and used to inoculate 11 two-liter baffled Erlenmeyer flasks, each containing 350 ml. of Medium IX with 2–3% inoculum using sterile pipettes. Medium IX has the following composition:

| Medium IX: | | |
|---|---|---|
| Amber Yeast No. 300 | 10.0 | g. |
| Distiller's Solubles | 20.0 | g. |
| Dextrose | 10.0 | g. |
| Distilled Water | 1000.0 | ml. |
| pH 7.0 | | |

The production flasks were then shaken at 28° C. on a 145 rpm. shaker with a two inch throw for four days. At the end of the incubation period the contents of 10 such flasks were combined and a sample was centrifuged to remove the mycelium.

The presence of Antibiotic 842A, i.e., the product 7β-(D-5-amino-5-carboxyvaleramido)-3-(carbamoyloxymethyl)-7-methoxy-3-cephem-4-carboxylic acid (Ib), in the broth was determined by agar diffusion assays performed with 0.5 inch filter paper discs soaked in the broth and set on the surface of assay plates containing 10 ml. of nutrient agar (Difco) plus 0.2% yeast extract (Difco) medium seeded with the bacterial inoculum. The zones of inhibition were measured in mm. after overnight incubation at 28° C. The assays of broth harvested after fermentation for four days showed an inhibition zone of 31.5 mm. diameter on plates seeded with *Vibrio percolans* (MB-1272).

Step B: Adsorption On An Anion Exchange Resin

The filtered broth was adjusted to pH 7.0 with dilute hydrochloric acid and 2,900 ml. was adsorbed on 100 ml. of a strongly basic anion exchange resin having a styrene-divinylbenzene matrix (Dowex 1 × 2 chloride cycle resin) at 10 ml/minute. The spent was collected in 500 ml. fractions. The resin column was washed with water and eluted with 3% NH₄Cl in 90% methanol. The eluate was collected in 100 ml. fractions.

Disc plate assays against *Vibrio Percolans* (MB-1272) were run on all fractions; the zone diameters are tabulated below.

| Filtered Broth | | Spent Fraction | | Eluate Fraction | |
|---|---|---|---|---|---|
| Dilution | Zone Size | Fraction | Zone Size | Fraction | Zone Size |
| None | 26.5 mm. | 1. | 0 | 1. | 25 |
| 1:2 | 24 | 2. | 16 | 2. | 29 |
| 1:4 | 20 | 3. | 23 | 3. | 29 |

-continued

| Filtered Broth | | Spent Fraction | | Eluate Fraction | |
|---|---|---|---|---|---|
| Dilution | Zone Size | Fraction | Zone Size | Fraction | Zone Size |
| | | 4. | 25 | 4. | 26.5 |
| | | 5. | 27 | 5. | 22 |
| | | 6. | 27 | 6. | 18 |
| | | | | 7. | 15 |
| | | 8–10. | 0 | | |

These assays indicate about 60% of the activity is in the spent and about 18% is in the eluates. This eluate is the ammonium salt of 842A. Furthermore, they indicate that the resin capacity is only two fractions or 10 column volumes of broth. Eluate fractions 1 through 4 were combined and concentrated to remove methanol. Spent fractions 3 through 6 were combined to give 1960 ml. of solution. An 1860 ml. portion of the solution was adjusted from pH 7.2 to 8.0 with dilute sodium hydroxide and adsorbed on 100 ml. of a strongly basic anion exchange resin having a styrene-divinylbenzene matrix (Dowex 1 × 2 chloride cycle resin) at 14 ml/minute. The spent was collected in four equal fractions and assays indicate that 5% of the activity was present. The column was washed with water and eluted with 5% aqueous sodium chloride. The eluate, which contains the sodium salt of 842A, was collected in 50 ml. fractions and assayed. The assays indicated that 90% of the activity was present in cuts 3 through 16 so these were combined.

Step C: Adsorption On A Cation Exchange Resin

A 50 ml. portion of a concentrate as prepared in Step B was diluted to 500 ml., adjusted from pH 8.8 to pH 2.0 with dilute hydrochloric acid and adsorbed on 25 ml. of a strongly acidic cation exchange resin of the sulfonate type having a styrene-divinylbenzene matrix (Dowex 50 × 2 hydrogen cycle resin) at 2.5 ml/minute. The column was washed with 25 ml. of water then eluted with 2% pyridine until the pH of the column effluent rose to pH 7 (54 ml.). Assays of the spent fraction and eluate indicated 9% of the activity in the spent and 90% in the eluate. The eluate was identified as the pyridinium salt of Antibiotic 842A.

The 842A product is amphoteric with an apparent isoelectric point at about pH 3.5. The product is unstable above pH 7 but stable at pH 1.5. The eluate thus obtained was adjusted to pH 8.0 with dilute sodium hydroxide and concentrated under vacuum to remove pyridine. The product thus obtained was identified as the monosodium salt of Antibiotic 842A. The molecular weight is 468 based on the empirical formula.

Analysis for $C_{16}H_{21}N_4SO_9Na$:

Calc: C, 41.0% H, 4.5%; N, 12.0%; S, 6.8%; O, 30.8%, Na, 4.9%.

Found: C, 39.31%; H, 4.76%; N, 11.16%; S, 6.46%; O, 34.12%; Na, 4.19%.

In in vitro studies this product, i.e., Antibiotic 842A, inhibits the growth of the following gram-negative bacteria: *Escherichia coli, Proteus vulgaris, Alcaligenes faecalis, Brucella bronchiseptica, Salmonella gallinarum, Vibrio percolans* and *Xanthomonas vesicatoria*. Also the product inhibits the growth of the following gram-positive bacteria: *Staphylococcus aureus, Sarcina lutea* and *Bacillus subtilis*.

In in vivo studies in mice Antibiotic 842A also exhibits the following activities. Administration was by subcutaneous injection. At the completion of the test period, usually seven days after administration, the amount of product required to protect 50% of the mice ($ED_{50}$) from this otherwise fatal injection was calculated:

| | $ED_{50}$ by Subcutaneous Route X Two Doses |
|---|---|
| *Proteus vulgaris* | 51 μg. |
| *Proteus mirabilis* | 276 μg. |
| *Proteus morganii* 3202 | 276 μg. |
| *Salmonella schottmuelleri* | 103 μg. |
| *Klebsiella pneumoniae* AD | 125 μg. |
| *Klebsiella pneumoniae* B | 125 μg. |
| *Paracolobactrum arizonae* | 125 μg. |
| *Escherichia coli* | 200 μg. |
| *Aerobacter aerogenes* | 49 μg. |
| *Pasteurella multocida* | 57 μg. |
| *Salmonella typhosa* | 34 μg. |
| *Diplococcus pneumoniae* 2400 | 566 μg. |

*Cephaloridine and Cephalothin failed to protect at 4000 mg. × 2 doses

In addition to the aforementioned in vivo trials of the product, a clinical isolate of *Proteus morganii* 356 which is resistant to cephalosporins and capable of degrading cephalosporin C, was employed in a mouse protection test performed in the same manner as reported above. The $ED_{50}$ for these tests is as follows:

| Infection | Antibiotic | $ED_{50}$ by Subcutaneous Route × 2 Doses (average of Two Trials) |
|---|---|---|
| *Proteus moganii* 356 | 842A | 273 μg. |
| *Proteus morganii* 356 | Cephalothin | >20,000 μg. |
| *Proteus morganii* 356 | Cephaloridine | 9,270 μg. |

EXAMPLE 9

Antibiotic 842A

Shake Flask Production:

The inoculum was prepared as described in Example 8. Two second-stage seed flasks were pooled and the broth used to inoculate (at 1 ml./flask) 62 Erlenmeyer flasks (250 ml.) each containing 50 ml. of Medium X. The Medium X has the following composition:

| Medium X: | |
|---|---|
| Staley's 4S-Soybean Meal | 30.0 g. |
| Distiller's Solubles | 7.5 g. |
| Cerelose | 20.0 g. |
| NaCl | 2.5 g. |
| $CaCO_3$ (after pH to 7.0) | 10.0 g. |
| Distilled Water | 1000.0 ml. |

The flasks were shaken at 28° C. on a 220 rpm. shaker with a 2 inch throw for 5 days. At the end of the incubation period the contents of 60 such flasks were combined and a sample was centrifuged to remove the mycelium.

The presence of Antibiotic 842A was determined by following the procedure described in Example 8 via agar diffusion assays performed in 0.5 inch filter paper assay discs. After incubation for 4 days, assay of broth gave an inhibition zone of 33 mm. versus Vibrio percolans (MB-1272).

EXAMPLE 10

Antibiotic 842A
Fermentation:

Stage 1: a lyophilized tube of *Streptomyces lactamdurans* culture (MA-2908) was used to inoculate 50 ml. of sterile Medium V in a baffled 200 ml. Erlenmeyer flask.

| Medium V: | | |
|---|---|---|
| Yeast Autolysate (Ardamine) | 10.0 | g. |
| Glucose | 10.0 | g. |
| *Phosphate Buffer | 2.0 | ml. |
| $MgSO_4 \cdot 7H_2O$ | 0.05 | g. |
| Distilled Water | 1000.0 | ml. |
| pH - adjust to 6.5 using NaOH | | |
| *Phosphate Buffer: | | |
| $KH_2PO_4$ | 91.0 | g. |
| $Na_2HPO_4$ | 95.0 | g. |
| Distilled Water | 1000.0 | ml. |

The inoculated flask was placed on a 220 rpm. rotary shaker with a two inch throw and incubated for 72 hours at 28° C.

Stage 2: An inoculum of 10.0 ml. of the resulting vegetative growth was then used to inoculate a two-liter baffled Erlenmeyer flask containing 50 ml. of the sterilized Medium V described above. The inoculated flask was then placed on a 220 rpm. rotary shaker and incubated for 48 hours at 28° C.

Stage 3: The contents of the inoculum flask was then used to inoculate a 50 gallon stainless fermentor containing 160 liters of the same Medium V described above. The inoculated medium was incubated at 28° C. for 48 hours with agitation while maintaining an airflow of 3 cfm through the fermenting broth. During the fermentation period, small amounts of Polyglycol 2000 were added to control foaming.

Stage 4: An inoculum of 43 liters of the resulting growth was then used to inoculate a 200 gallon stainless steel fermentor containing 467 liters of a sterile Medium XII having the following composition:

| Medium XI: | |
|---|---|
| Amber Yeast No. 300 | 10.0 g. |
| Distiller's Solubles | 20.0 g. |
| Distilled Water | 1000.0 ml. |
| pH 7.0 | |

The fermentation was allowed to proceed at a temperature of 28° C. with agitation while maintaining an airflow of 10 cfm for 72 hours. During the fermentation an antifoam agent, Polyglycol 2000 was added in small quantities to prevent excessive foaming. The batch was harvested and activity was determined by disc plate assay. The fermentation broth was then filtered through diatomaceous earth at a pH of 7.8 and the product thus obtained was identified as 842A by following the procedure described in Example 8. Disc-plate assays of a 1:10 dilution gave an inhibition zone of 21.5 mm. v. *Vibrio percolans* (MB-1272).

EXAMPLE 11

Purification; Monosodium Salt of 7β-(D-5-Amino-5-Carboxy-valeramido)-3-(Carbamoyloxymethyl)-7-Methoxy-3-Cephem-4-Carboxylic Acid Adsorption on Carbon: Four fermentation batches harvested according to Example 8, were each adsorbed on 100 ml. of a strongly basic anion exchange resin having a styrenedivinylbenzene matrix (Dowex 1 × 2 chloride cycle resin) and eluted with 1% aqueous sodium chloride. The eluate was collected in 50 ml. fractions and assayed. Eluate fractions from all four batches were adjusted to pH 5 with dilute hydrochloric acid and combined to give 4300 ml. of solution. 4,200 ml. of this solution was stirred with 42 g. of carbon (Darco G-60) for one-half hour. The carbon was collected by filtration and washed with water. The filtrate and wash were void of activity. The carbon cake was eluted twice with a one liter portion of 60% aqueous acetone by stirring the mixture for one-half hour and filtering each time. The eluates were concentrated under vacuum to 108 ml. and 100 ml., respectively. Assays indicated that the first eluate contained 76% of the activity, 18 times as potent as the starting material and that the second contained 17% of the activity, 14 times as potent as the starting material. The two concentrates were combined and concentrated further to 61 ml. and adjusted from pH 4 to pH 5 with dilute sodium hydroxide. This concentrate contained 40 mg/ml. of dry solids and gave a 25 mm. zone against MB-1272 at a dilution of 1:100 (400 μg./ml.). The product was identified as the monosodium salt of 7β-(D-5-amino-5-carboxyvaleramido)-3-(carbamoyloxymethyl)-7-methoxy-3-cephem-4-carboxylic acid (Ib).

EXAMPLE 12

Purification; Monosodium Salt of 7β-(D-5-Amino-5-Carboxyvaleramido)-3-(Carbamoyloxymethyl)-7-Methoxy-3-Cephem-4-Carboxylic Acid Separation on Gel: A 22 ml. portion of the eluate obtained according to Example 8, Step B, was adjusted to pH 7.0 with dilute sodium hydroxide and chromatographed on a column containing 388 ml. of BioGel P-2. The column was developed with water, the effluent monitored with a differential refractometer and 5 ml. fractions collected automatically and bioassayed. The bioactivity appeared in fractions 47 through 63 while sodium chloride appeared in fractions 62 through 72. Fractions 50 through 60 were pooled, reassayed and concentrated to dryness yielding 10.8 mg. of residue identified as the monosodium salt of 7β-(D-5-amino-5-carboxyvaleramido)-3-(carbamoyloxymethyl)-7-methoxy-3-cephem-4-carboxylic acid (Ib). On assay with *Vibrio percolans* this product gave a 25 mm. zone at 8 meg./ml.

EXAMPLE 13

7β-(D-5-Amino-5-Carboxyvaleramido)-3-(Carbamoyloxymethyl)-7-Methoxy-3-Cephem-4-Carboxylic Acid Modified Fermentation Process:
Step A: Slants
A lyophilized tube of *Streptomyces lactamdurans* culture (MA-2908) was opened aseptically and the organism transferred to a medium of the following composition:

Medium XII:
1% Blackstrap Molasses
1% National Brewer's Yeast
2.5% Difco agar pH 7.0
Water to volume The slants are incubated for seven days at 28° C. When stored in the cold, the slants are stable for more than 13 weeks.

Step B: Seed Stages: Two Stage System

First Seed: The first seed is inoculated directly from the slant of Step A to 40 ml. of 1% Primary Dried Yeast N.F., pH 7.0 (obtained from the Yeast Product Corporation) in a 250 ml. baffled Erlenmeyer flask. The flasks were then shaken on a 220 rpm. rotary shaker with a 2 inch throw at 28° C. for a period of from 2 to 3 days.

Second Seed: A 2.5% inoculum from the first seed stage was added to a flask containing a 2% Fleischmann S-150 yeast autolysate, pH 7.0. The growth in this stage is characteristically light and the incubation, performed as in the first stage, was not extended beyond 48 hours.

Step C: Production Medium

The production medium contains per liter of distilled water: 30 g. distiller's solubles; 7.5 g. Primary Dried Yeast N.F. and 0.25% v/v Mobilpar-S deformer. The medium is adjusted to pH 7.0 with a small amount of concentrated NaOH solution, dispensed into 250 ml. Erlenmeyer flasks and autoclaved for 15 or 20 minutes at 121° C. After cooling the medium received a 2.5% inoculum of the seed obtained in Step B. The time of incubation can vary from about 50 hours to 100 hours but an incubation period of about 72 hours is preferred. The volume of media in each flask can vary from 30 to 50 ml. but 40 ml. was used routinely. The level of inoculum can vary from 1% to 5%; but, in practice, a 2.5% level is generally employed.

Step D: Assay

When the fermentation was complete, the cells were removed by centrifugation and the broth was diluted with phosphate buffer, pH 7.0. The concentration of 7β-(D-5-amino-5-carboxyvaleramido)-3-(carbamoyloxymethyl)-7-methoxy-3-cephem-4-carboxylic acid in the fermentation broth was determined by the standard biological-disc assay method. The assay organism employed was *Vibrio percolans* (ATCC 8461). Filter paper discs are emersed into the diluted broths and placed on the surface of agar-containing Petri dishes that has been inoculated with the assay organism *Vibrio percolans* (ATCC 8461). Also placed on these Petri dishes are discs that had been dipped previously in standard solutions containing known concentrations of 842A. The discs were incubated overnight at 28° C. and the diameters of the zones of inhibition recorded. The concentration of 842A and the fermented broth is calculated by interpolation from the standard curve which relates zone diameter with the known concentrations of standard 842A solutions. By this procedure it was calculated that *Streptomyces lactamdurans* MB-2908 produced 78.6 μg./ml. of 842A in the modified fermentation process.

EXAMPLE 14

Disodium Salt of 7β-(D-5-Amino-5-Carboxyvaleramido)-3-(N,N-Dimethylcarbamoyloxymethyl)-7-Methoxy-3-Cephem-4-Carboxylic Acid Step A: 7β-(D-5-Phthaloylamino-5-Carboxyvaleramido)-3-(Carbamoyloxymethyl)-7-Methoxy-3-Cephem-4-Carboxylic Acid 7β-(D-5-Amino-5-carboxyvaleramido)-3-(carbamoyloxymethyl)-7-methoxy-3-cephem-4-carboxylic acid (2.005 g., 4.27 m. moles) is dissolved in a solution of 10% aqueous dipotassium hydrogen phosphate (26 ml.). The mixture is then filtered and the resulting solid washed with 10% aqueous dipotassium hydrogen phosphate (2 ml.).

To the filtrate is added 10 ml. of acetone. The solution becomes slightly cloudy and a has a pH of 8.45. To this solution was added 50% aqueous tripotassium phosphate to adjust the pH to 9.18. N-Ethoxycarbonylphthalimide (1.492 g., 6.69 m. moles) in acetone (5.0 ml.) is then added over a five minute period. The pH is adjusted to 9.1 by adding increments of 50% aqueous tripotassium phosphate over the next 1.5 hours. The mixture is then evaporated to remove acetone and the pH adjusted to 2 to 2.5 with 2.5 N hydrochloric acid. The mixture is extracted with four washes of ethyl acetate (25 ml.) and the combined pale yellow extracts are washed with 25 ml. of water, dried with anhydrous sodium sulfate overnight and evaporated to afford 2.356 g. of a yellow foam. Nuclear magnetic resonance and electrophoresis confirm that the product thus obtained is 7β-(D-5-phthaloylamino-5-carboxyvaleramido)-3-(carbamoyloxymethyl)-7-methoxy-3-cephem-4-carboxylic acid.

Step B: Dibenzhydryl Ester of 7β-(D-5-Phthaloylamino-5-Carboxyvaleramido)-3-(Carbamoyloxymethyl)-7-Methoxy-3-Cephem-4-Carboxylic Acid A solution of 7β-(D-5-phthaloylamino-5-carboxyvaleramido)-3-(carbamoyloxymethyl)-7-methoxy-3-cephem-4-carboxylic acid (0.653 mg.) in methanol is treated with a slight excess of freshly prepared diphenyldiazomethane. After standing overnight at room temperature the solution is evaporated to afford 1.053 g. of residue identified as the dibenzhydryl ester of 7β-(D-5-phthaloylamino-5-carboxyvaleramido)-3-(carbamoylxoymethyl)-7-methoxy-3-cephem-4-carboxylic acid.

Step C: Dibenzhydryl Ester of 7β-(D-5-Phthaloylamino-5-Carboxyvaleramido)-3-(Hydroxymethyl)-7-Methoxy-3-Cephem-4-Carboxylic Acid The dibenzhydryl ester of 7β-(D-5-phthaloylamino-5-carboxyvaleramido)-3-(carbamoyloxymethyl)-7-methoxy-3-cephem-4-carboxylic acid (0.5 g.) obtained in Step B is dissolved in purified dioxane (5 ml.) containing 1.5 equivalents of pyridine. A solution of nitrosylchloride (1.3 equivalents) in methylene chloride is added and the solution stirred in an ice bath for one hour. The product thus obtained is a solution of the dibenzhydryl ester of 7β-(D-5-phthaloylamino-5-carboxyvaleramido)-3-(hydroxymethyl)-7-methoxy-3-cephem-4-carboxylic acid which is used directly in the following step.

Step D: Dibenzhydryl Ester of 7β-(D-5Phthaloylamino-5-Carboxyvaleramido)-3-

(Chlorocarbonyloxymethyl)-7-Methoxy-3-Cephem-4-Carboxylic Acid

An excess of phosgene is bubbled into a stirred solution of the 7β-(D-5-phthaloylamino-5-carboxyvaleramido)-3-(hydroxymethyl)-7-methoxy-3-cephem-4-carboxylic acid obtained in Step C and the mixture is allowed to stand at room temperature overnight. The excess phosgene is removed by bubbling dried nitrogen through the solution for several hours. The product thus obtained is identified as the dibenzhydryl ester of 7β-(D-5-phthaloylamino-5-carboxyvaleramido)-3-(chlorocarbonyloxymethyl)-7-methoxy-3-cephem-4-carboxylic acid.

Step E: Dibenzhydryl Ester of 7β-(D-5-Phthaloylamino-5-Carboxyvaleramido)-3-(N,N-Dimethylcarbamoyloxymethyl-7-Methoxy-3-Cephem-4-Carboxylic Acid The dibenzhydryl ester of 7β-(D-5-phthaloylamino-5-carboxyvaleramido)-3-(chlorocarbonyloxymethyl-7-methoxy-3-cephem-4-carboxylic acid obtained according to Step D is cooled in an ice bath and 2.5 equivalents of dimethylamine is added. The mixture is stirred at room temperature for one hour and the excess amine hydrochloride filtered off. The product thus obtained is identified as the dibenzhydryl ester of 7β-(D-5-phthaloylamino-5-carboxyvaleramido)-3-(N,N-dimethylcarbamoyloxymethyl)-7-methoxy-3-cephem-4-carboxylic acid.

Step F: Disodium Salt of 7β-(D-5-Phthaloylamino-5-Carboxyvaleramido)-3-(N,N-Dimethylcarbamoyloxymethyl-7-Methoxy-3-Cephem-4-Carboxylic Acid The dibenzhydryl ester of 7β-(D-5-phthaloylamino-5-carboxyvaleramido)-3-(N,N-dimethylcarbamoyloxymethyl)-7-methoxy-3-cephem-4-carboxylic acid obtained in Step E is dissolved in anisole (3.5 ml.) and treated with trifluoroacetic acid (10 ml.) at room temperature for 10 minutes. The trifluoroacetic acid and anisole are then removed under reduced pressure while maintaining the temperature below 40° C., and the residue is taken up in 25 ml. of chloroform and treated with 20 ml. of water, containing 0.120 g. of sodium bicarbonate. The mixture is stirred for 0.5 hour at room temperature and the organic phase is separated and washed with water. The combined aqueous phase is then washed twice with methylene chloride and lyophilized to afford the disodium salt of 7β-(D-5-phthaloylamino-5-carboxyvaleramido)-3-(N,N-dimethylcarbamoyloxymethyl)-7-methoxy-3-cephem-4-carboxylic acid.

Step G: Disodium Salt of 7β-(D-5-Amino-5-Carboxyvaleramido)-3-(N,N-dimethylcarbamoyloxymethyl)-7-Methoxy-3-Cephem-4-Carboxylic Acid The disodium salt of 7β-(D-5-phthaloylamino-5-carboxyvaleramido)-3-(N,N-dimethylcarbamoyloxymethyl)-7-methoxy-3-cephem-4-carboxylic acid obtained in Step F is dissolved in water. One equivalent of hydrazine hydrate is then added and the mixture is allowed to stand at room temperature overnight. The aqueous solution is extracted with ethyl acetate before lyophilization to afford the disodium salt of 7β-(D-5-amino-5-carboxyvaleramido)-3-(N,N-dimethylcarbamoyloxymethyl)-7-methoxy-3-cephem-4-carboxylic acid.

EXAMPLE 15

Disodium Salt of 7β-(D-5-Amino-5-Carboxyvaleramido)-3-(Piperidinocarbonyloxymethyl)-7-Methoxy-3-Cephem-4-Carboxylic Acid Step A: Dibenzhydryl Ester of 7β-(D-5-Phthaloylamino-5-Carboxyvaleramido)-3-(Piperidinocarbonyloxymethyl)-7-Methoxy-3-Cephem-4-Carboxylic Acid Upon substituting an equivalent amount of piperidine for the dimethylamine of Example 14, Step E, and following the procedure described therein there is thus obtained the dibenzhydryl ester of 7β-(D-5-phthaloylamino-5-carboxyvaleramido)-3-(piperidinocarbonyloxymethyl)-7-methoxy-3-cephem-4-carboxylic acid.

Step B: Disodium Salt of 7β-(D-5-Amino-5-Carboxyvaleramido)-3-(Piperidino carbonyloxymethyl)-7-Methoxy-3-Cephem-4-Carboxylic Acid Upon substituting the dibenzhydryl ester of 7β-(D-5-phthaloylamino-5-carboxyvaleramido)-3-(piperidinocarbonyloxymethyl)-7-methoxy-3-cephem-4-carboxylic acid obtained according to Step A for the dibenzhydryl ester of 7β-(D-5-phthaloylamino-5-carboxyvaleramido)-3-(N,N-dimethylcarbamoyloxymethyl)-7-methoxy-3-cephem-4-carboxylic acid recited in Example 14, Step F, and following the de-esterification method described therein there is thus obtained the disodium salt of 7β-(D-5-phthaloylamino-5-carboxyvaleramido)-3-(piperidinocarbonyloxymethyl)-7-methoxy-3-cephem-4-carboxylic acid which, when treated with hydrazine hydrate according to the method described in Example 14, Step G, affords the disodium salt of 7β-(D-5-amino-5-carboxyvaleramido)-3-(piperidinocarbonyloxymethyl)-7-methoxy-3-cephem-4-carboxylic acid.

EXAMPLE 16

Disodium Salt of 7β-(D-5-Amino-5-Carboxyvaleramido)-3-(Pyrrolidinylcarbonyloxymethyl)-7-Methoxy-3-Cephem-4-Carboxylic Acid Step A: Dibenzhydryl Ester of 7β-(D-5-Phthaloylamino-5-Carboxyvaleramido)-3-(Pyrrolidinylcarbonyloxymethyl)-7-Methoxy-3-Cephem-4-Carboxylic Acid Upon substituting an equivalent amount of pyrrolidine for the dimethylamine of Example 14, Step E, and following the procedure described therein there is thus obtained the dibenzhydryl ester of 7β-(D-5-phthaloylamino-5-carboxyvaleramido)-3-(pyrrolidinylcarbonyloxymethyl)-7-methoxy-3-cephem-4-carboxylic acid.

Step B: Disodium Salt of 7β-(D-5-Amino-5-Carboxyvaleramido)-3-(Pyrrolidinylcarbonyloxymethyl)-7-Methoxy-3-Cephem-4-Carboxylic Acid.

Upon substituting the dibenzhydryl ester of 7β-(D-5-phthaloylamino-5-carboxyvaleramido)-3-(pyrrolidinylcarbonyloxymethyl)-7-methoxy-3-cephem-4-carboxylic acid obtained according to Step A for the dibenzhydryl ester of 7β-(D-5-phthaloylamino-5-carboxyvaleramido)-3-(N,N-dimethylcarbamoyloxymethyl)-7-methoxy-3-cephem-4-carboxylic acid recited in Example 14, Step F, and following the de-esterification method described therein there is thus obtained the di-sodium salt of 7β-(D-5-phthaloylamino-5-carboxyvaleramido)-3-(pyrrolidinylcarbonyloxymethyl)-7-methoxy-3-cephem-4-carboxylic acid which, when treated with hydrazine hydrate according to the method described in Example 14, Step G, affords the disodium salt of 7β-(D-5-amino-5-carboxy leramido)-3-(pyrrolidinylcarbonyloxymethyl)-7-methoxy-3-cephem-4-carboxylic acid.

EXAMPLE 17

Disodium Salt of 7β-(D-5-Amino-5-Carboxyvaleramido)-3-(Morpholinocarbonyloxymethyl)-7-Methoxy-3-Cephem-4-Carboxylic Acid Step A: Dibenzhydryl Ester of 7β-(D-5-Phthaloylamino-5-Carboxyvaleramido)-3-(Morpholinocarbonyloxymethyl)-7-Methoxy-3-Cephem-4-Carboxylic Acid Upon substituting an equivalent amount of morpholine for the dimethylamine of Example 14, Step E, and following the procedure described therein there is thus obtained the dibenzhydryl ester of 7β-(D-5-phthaloylamino-5-carboxyvaleramido)-3-(morpholinocarbonyloxymethyl)-7-methoxy-3-cephem-4-carboxylic acid.

Step B: Disodium Salt of 7β-(D-5-Amino-5-Carboxyvaleramido)-3-(Morpholinocarbonyloxymethyl)-7-Methoxy-3-Cephem-4-Carboxylic Acid Upon substituting the dibenzhydryl ester of 7β-(D-5-phthaloylamino-5-carboxyvaleramido)-3-(morpholinocarbonyloxymethyl)-7-methoxy-3-cephem-4-carboxylic acid obtained according to Step A for the dibenzhydryl ester of 7β-(D-5-phthaloylamino-5-carboxyvaleramido)-3-(N,N-dimethylcarbamoyloxymethyl)-7-methoxy-3-cephem-4-carboxylic acid recited in Example 14, Step F, and following the de-esterification method described therein there is thus obtained the disodium salt of 7β-(D-5-phthaloylamino-5-carboxyvaleramido)-3-(morpholinocarbonyloxymethyl-7-methoxy-3-cephem-4-carboxylic acid which, when treated with hydrazine hydrate according to the method described in Example 14, Step G, affords the disodium salt of 7β-(D-5-amino-5-carboxyvaleramido)-3-(morpholinocarbonyloxymethyl)-7-methoxy-3-cephem-4-carboxylic acid.

EXAMPLE 18

Disodium Salt of 7β-(D-5-amino-5-Carboxyvaleramido)-3-(Acetoxymethyl)-7Methoxy-3-Cephem-4-Carboxylic Acid Step A: Dibenzhydryl Ester of 7β-(D-5-Phthaloylamino-5-Carboxyvaleramido)-3-(Acetoxymethyl)-7-Methoxy-3-Cephem-4Carboxylic Acid An excess of acetyl chloride is added with stirring to the dibenzhydryl ester of 7β-(D-5-phthaloylamino-5-carboxyvaleramido)-3-(hydroxymethyl)-7-methoxy-3-cephem-4-carboxylic acid obtained in Example 14, Step C. The mixture is allowed to stand for several hours at room temperature. The mixture is then concentrated in vacuo to remove excess acetyl chloride and solvent. The residue thus obtained is the dibenzhydryl ester of 7β-(D-5-phthaloylamino-5-carboxyvaleramido)-3-(acetoxymethyl)-7-methoxy-3-cephem-4-carboxylic acid.

The dibenzhydryl ester of 7β-(D-5-phthaloylamino-5-carboxyvaleramido)-3-(acetoxymethyl)-7-methoxy-3-cephem-4-carboxylic acid can also be obtained by substituting ketene for acetyl chloride and otherwise following the procedure described in this Step A.

Step B: Disodium Salt of 7β-(D-5-Phthaloylamino-5-Carboxyvaleramido)-3-(Acetoxymethyl)-7-Methoxy-3-Cephem-4-Carboxylic Acid The dibenzhydryl ester of 7β-(D-5-phthaloylamino-5-carboxyvaleramido)-3-(acetoxymethyl)-7-methoxy-3-cephem-4-carboxylic acid obtained in Step A is dissolved in dioxane and the mixture is subjected to the de-esterification method described in Example 14, Step F. There is thus obtained a residue comprising the disodium salt of 7β-(D-5-phthaloylamino-5-carboxyvaleramido)-3-(acetoxymethyl)-7-methoxy-3-cephem-4-carboxylic acid.

Step C: Disodium Salt of 7β2-(D-5-Amino-5-Carboxyvaleramido)-3-(Acetoxymethyl)-7-Methoxy-3-Cephem-4-Carboxylic Acid The disodium salt of 7β-(D-5-phthaloylamino-5-carboxyvaleramido)-3-(acetoxymethyl)-7-methoxy-3-cephem-4-carboxylic acid obtained in Step B is dissolved in methylene chloride and the solution extracted with 5% sodium bicarbonate solution. The resulting mixture is then acidified to pH 2 with sulfuric acid and extracted with ethyl acetate. Upon drying the extract is concentrated in vacuo and the residue is dissolved in water containing two equivalents of sodium bicarbonate. One equivalent of hydrazine hydrate is then added and the mixture is allowed to stand at room temperature overnight. The aqueous solution is extracted with ethyl acetate before lyophilization to afford the disodium salt of 7β-(D-5-amino-5-carboxyvaleramido)-3-(acetoxymethyl)-7-methoxy-3-cephem-4-carboxylic acid.

In a manner similar to that described in Example 18 all of the 3-acyloxy substituted derivatives of this invention may be obtained. Thus, for example, by substituting the appropriate acyl halide for the acetyl chloride of Example 18, Step A and following the procedure described in Steps A, B and C of that example all of the corresponding 3-alkanoyloxy, 3-aromatic-carbonyloxy, 3-aralkanoyloxy and 3-cycloalkanecarbonyloxy substituted derivatives of this invention may be obtained. The following equation and Table XVIII illustrate this method and the products obtained thereby.

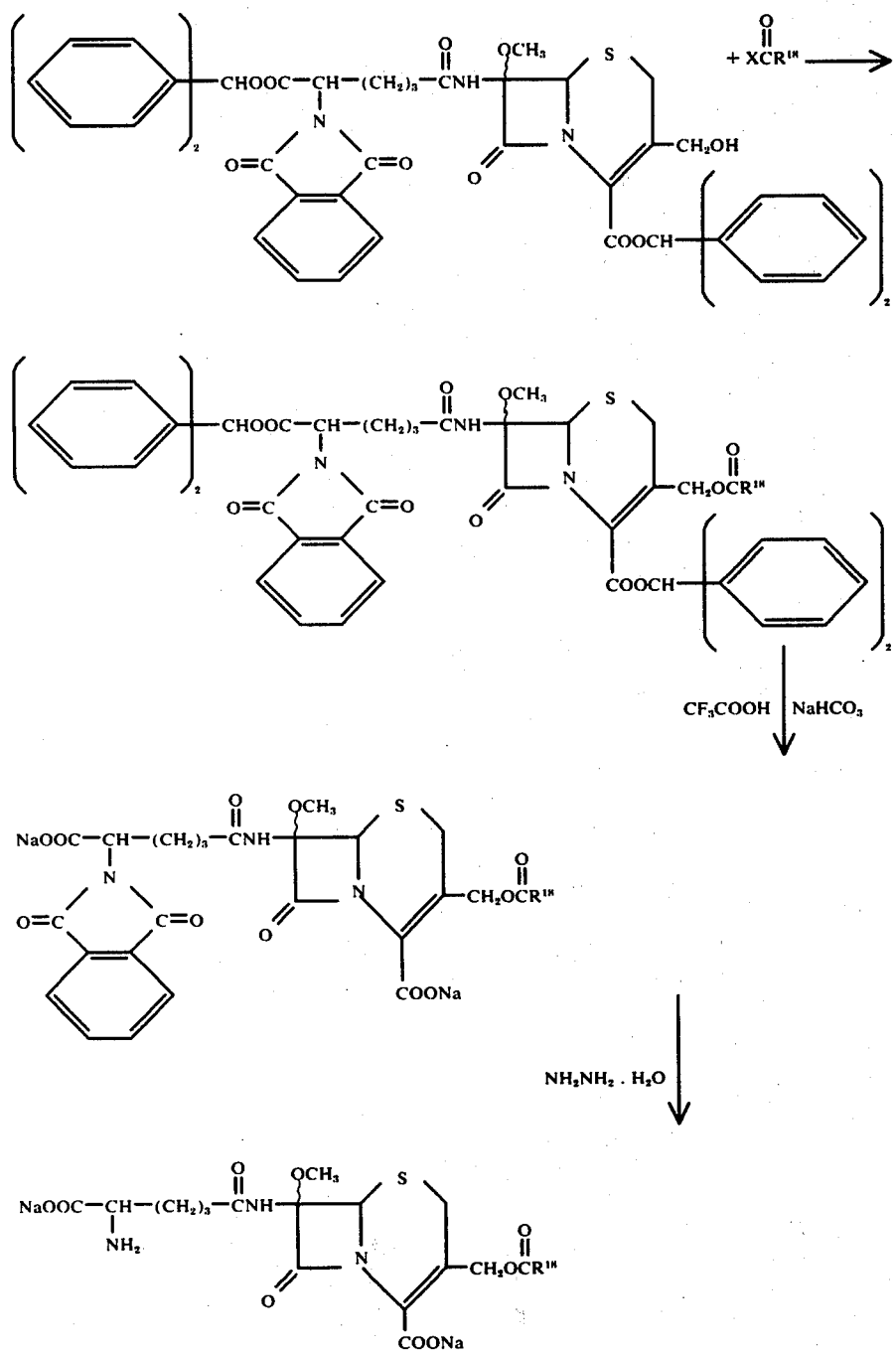
| TABLE XVIII | | |
|---|---|---|
| Ex. | X | $R^{1N}$ |
| 19 | Cl | $-C_2H_5$ |
| 20 | Br | ![phenyl] |
| 21 | Cl | ![naphthyl] |
| TABLE XVIII-continued | | |
|---|---|---|
| Ex. | X | $R^{1N}$ |
| 22 | Br | $-CH_2$-![phenyl] |
| 23 | Cl | $-CH_2$-![naphthyl] |

TABLE XVIII-continued

| Ex. | X | R¹⁸ |
|---|---|---|
| 24 | Cl | 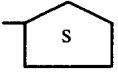 |
| 25 | Cl | 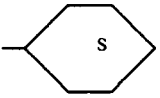 |
| 26 | Cl | —CH₂—CH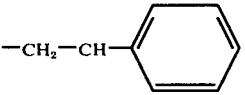 |
| 27 | Br | 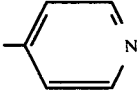 |

EXAMPLE 28

Disodium Salt of 7β-(D-5-Amino-5-Carboxyvaleramido)-3-(N-Methylcarbamoyloxymethyl)-7-Methoxy-3-Cephem-4-Carboxylic Acid Step A: Dibenzhydryl Ester of 7β-(D-5-Phthaloylamino-5-Carboxyvaleramido)-3-(N-Methylcarbamoyloxymethyl)-7-Methoxy-3-Cephem-4-Carboxylic Acid The dibenzhydryl ester of 7β-(D-5-phthaloylamino-5-carboxyvaleramido)-3-(hydroxymethyl)-7-methoxy-3-cephem-4-carboxylic acid (250 mg.) is suspended in dimethylformamide (5 ml.). The reaction mixture is placed under nitrogen and agitated by ultrasonic waves. Triethylamine (0.20 ml.) and methylisocyanate (0.625 ml.) are then added and after dissolving the mixture is allowed to stand for 0.5 hour.

Ethyl ether is added to the mixture and after centrifuging, the ether is decanted. An additional quantity of ethyl ether is added to the oily residue and solidification of the product is facilitated by scratching. The resulting solid is recrystallized from a hot mixture of methanol and isopropanol (180 mg.) in two crops and the combination of these two crops are recrystallized again to afford a product identified as the dibenzhydryl ester of 7β-(D-5-phthaloylamino-5-carboxyvaleramido)-3-(N-methylcarbamoyloxymethyl)-7-methoxy-3-cephem-4-carboxylic acid.

Step B: Disodium Salt of 7β-(D-5-Phthaloylamino-5-Carboxyvaleramido)-3-(N-Methylcarbamoyloxymethyl)-7-Methoxy-3-Cephem-4-Carboxylic Acid The dibenzhydryl ester of 7β-(D-5-phthaloylamino-5-carboxyvaleramido)-3-(N-methylcarbamoyloxymethyl)-7-methoxy-3-cephem-4-carboxylic acid obtained in Step A is dissolved in anisole (3.5 ml.) and treated with trifluoroacetic acid (10 ml.) at room temperature for 10 minutes. The trifluoroacetic acid and anisole are then removed under reduced pressure while maintaining the temperature below 40° C., and the residue is taken up in 25 ml. of chloroform and treated with 20 ml. of water, containing 0.120 g. of sodium bicarbonate. The mixture is stirred for 0.5 hour at room temperature and the organic phase is separated and washed with water. The combined aqueous phase is then washed twice with methylene chloride and lyophilized to afford the di-sodium salt of 7β-(D-5-phthaloylamino-5-carboxyvaleramido)-3-(N-methylcarbamoyloxymethyl)-7-methoxy-3-cephem-4-carboxylic acid.

Step C: Disodium Salt of 7β-(D-5-Amino-5-Carboxyvaleramido)-3-(N-Methylcarbamoyloxymethyl)-7-Methoxy-3-Cephem-4-Carboxylic Acid The disodium salt of 7β-(D-5-phthaloylamino-5-carboxyvaleramido)-3-(N-methylcarbamoyloxymethyl)-7-methoxy-3-cephem-4-carboxylic acid obtained in Step B is dissolved in water. One equivalent of hydrazine hydrate is then added and the mixture is allowed to stand at room temperature overnight. The aqueous solution is extracted with ethyl acetate before lyophilization to afford the disodium salt of 7β-(D-5-amino-5-carboxyvaleramido)-3-(N-methylcarbamoyloxymethyl)-7-methoxy-3-cephem-4-carboxylic acid.

By following the procedure described in Example 28 all of the 3-(N-mono-substituted carbamoyloxymethyl)-derivatives of this invention may be obtained. Thus, by substituting the appropriate isocyanate for the methylisocyanate of Example 2S, Step A, and following the procedure described in Steps A, B and C of that Example all of the corresponding 3-carbamoyloxymethyl substituted derivatives of this invention may be synthesized. The following equation illustrates the reaction of Example 28, Steps A, B and C and, together with Table IX, infra, illustrate the starting materials of this process and the products derived therefrom:

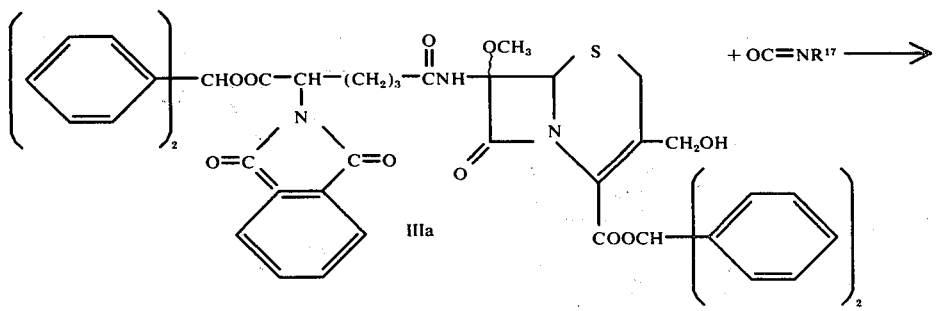

-continued

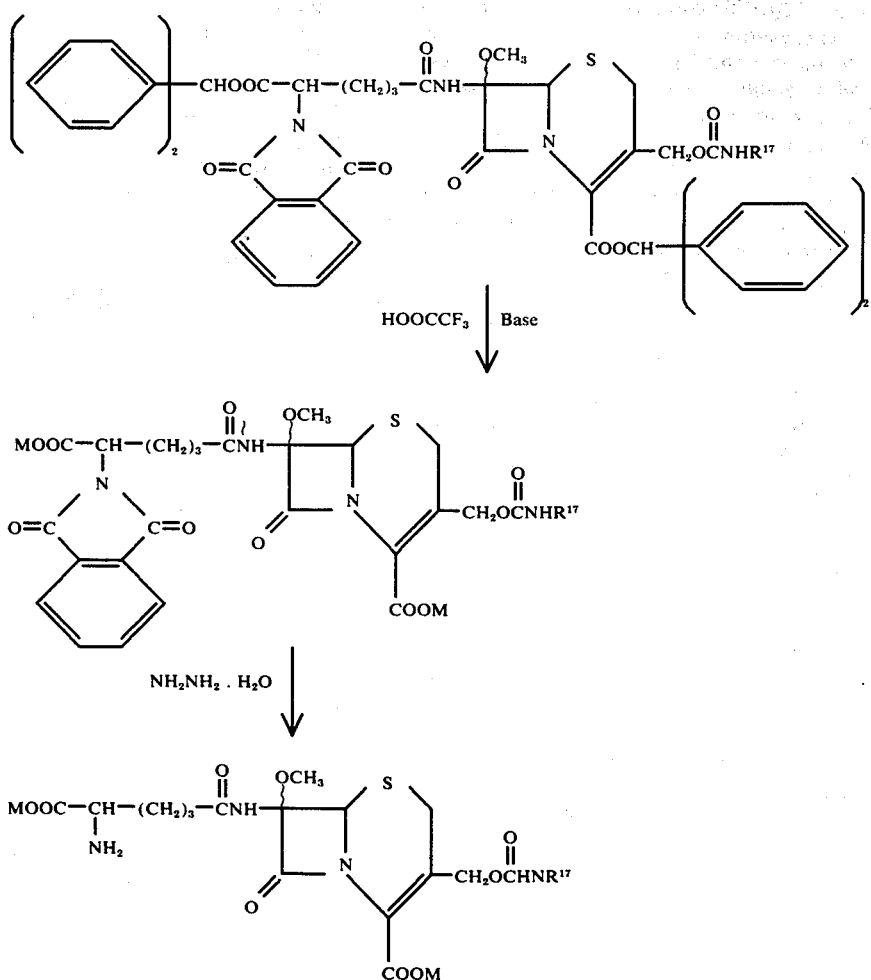

TABLE XIX

| Ex. | O=C=NR[17] | R[17] | Base | M |
|---|---|---|---|---|
| 29 | O=C=NCH₂CH₂Cl | —CH₂CH₂Cl | NaHCO₃ | —Na |
| 30 | O=C=NCH₂Cl | —CH₂Cl | KHCO₃ | —K |
| 31 | O=C=NC(CH₃)₃ | —C(CH₃)₃ | NaHCO₃ | —Na |
| 32 | O=C=NC₂H₅ | —C₂H₅ | KHCO₃ | —K |
| 33 | O=C=NC(CH₃)₂CH₂Cl | —C(CH₃)₂CH₂Cl | NaHCO₃ | —Na |
| 34 | O=C=NCOOC₂H₅ | —COOC₂H₅ | NaHCO₃ | —Na |
| 35 | O=C=NSO₂—⟨C₆H₄⟩—CH₃ | —SO₂—⟨C₆H₄⟩—CH₃ | NaHCO₃ | —Na |
| 36 | O=C=N—⟨C₆H₅⟩ | —⟨C₆H₅⟩ | NaHCO₃ | —K |
| 37 | O=C=NCH—(⟨C₆H₅⟩)₂ | —CH—(⟨C₆H₅⟩)₂ | NaHCO₃ | —Na |

EXAMPLE 38

7β-(D-5-Carboxyvaleramido)-3-(Pyridiniummethyl)-7-Methoxy-3-Cephem-4-Carboxylic Acid A solution of 7β-(D-5-amino-5-carboxyvaleramido)-3-(acetoxymethyl)-7-methoxy-3-cephem-4-carboxylic acid (1.0 g.) is brought to pH 2.5. Pyridine (8 ml.) is added and the solution is heated at 60° C. for 2 hours. The reaction mixture is then lyophilized and the residue is dissolved in water and passed through a polystyrene trimethylbenzylammonium anion exchange resin (43% H₂O). The resulting mixture of 7β-(D-5-amino-5-carboxyvaleramido)-3-(pyridinium-methyl)-7-methoxy-3-cephem-4-carboxylic acid is diluted with water and selected fractions are lyophilized to afford substantially pure 7β-(D-5-amino-5-caboxyvaleramido)-3-(pyridiniummethyl)-7-methoxy-3-cephem-4-carboxylic acid.

Upon substituting an equivalent amount of trimethylamine and triethylamine for pyridine in the foregoing process and otherwise following the procedure described therein, there is thus obtained 7β-(D-5-amino-5-carboxyvaleramido)-3-(trimethylammoniummethyl)-7-methyl-3-cephem-4-carboxylic acid and 7β-(D-5-amino-5-carboxyvaleramido)-3-(triethylammonium-methyl)-7-methoxy-3-cephem-4-carboxylic acid.

All of the 3-pyridiniummethyl derivatives of this invention may be obtained by substituting the appropriate mononuclear substituted pyridine for the pyridine reactant recited in the foregoing example. The following equation and accompanying Table illustrate this method of preparation and the products obtained thereby:

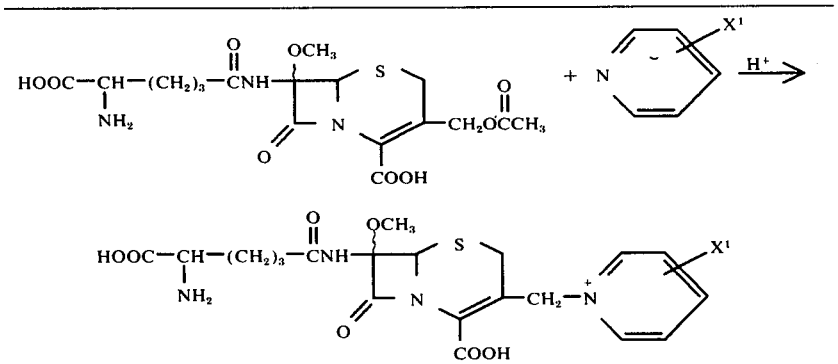

TABLE XX

| Ex. | X¹ | Ex. | X¹ |
|-----|----|-----|----|
| 39 | 3-F | 52 | 3-CON($C_2R_5$)$_2$ |
| 40 | 3-Cl | 53 | 3-$CH_2$COOH |
| 41 | 3-Br | 54 | 3-COCH$_3$ |
| 42 | 3-I | 55 | 4-COCH$_3$ |
| 43 | 4-CF$_3$ | 56 | 2-CH$_3$ |
| 44 | 3-COOH | 57 | 2-C$_2$H$_5$ |
| 45 | 4-COOH | 58 | 3-CH$_3$ |
| 46 | 3-CONH$_2$ | 59 | 4-C$_2$H$_5$ |
| 47 | 4-CONH$_2$ | 60 | 3-CH$_2$OH |
| 48 | 3-CONHCH$_3$ | 62 | 4-CH$_2$CH$_2$CH$_3$ |
| 50 | 4-CONHCH(CH$_3$)$_2$ | 63 | 3-SO$_3$H |
| 51 | 4-CON(CH$_3$)$_2$ | 64 | 3-CN |

EXAMPLE 65

S-[7β(D-5-amino-5-Carboxyvaleramido)-4-Carboxy-7-Methoxy-3-Cephem-3-ylmethyl)Isothiourea A solution of 7β-(D-5-amino-5-carboxyvaleramido)-3-(acetoxymethyl)-7-methoxy-3-cephem-4-carboxylic acid (1.0 g.) and thiourea (1.0 g.) in 25 ml. of water is maintained at 37° C. for 5 days. Acetone (200 ml.) is added and the mixture is chilled in an ice-bath. The resulting product is then filtered and fractionated through a polystyrene trimethylbenzylammonium anion exchange resin (43% H$_2$O). Selected fractions are lyophilized and the crude product is then recrystallized from a mixture of methanol and water to afford substantially pure S-[7β-(D-5-amino-5-carboxyvaleramido)-4-carboxy-7-methoxy-3-cephem-3-ylmethyl]-isothiourea.

Upon substituting an equivalent amount of N-methylthiourea, N-ethylthiourea, N-propylthiourea, N,N-dimethylthiourea, N,N-diethylthiourea and N,N-dipropylthiourea for the thiourea recited in the foregoing process and otherwise following the procedure described therein, there is thus obtained N-methyl-S-[7β-(D-5-amino-5-carboxyvaleramido)-4-carboxy-7-methoxy-3-cephem-3-ylmethyl]isothiourea, N-ethyl-S-[7β-(D-5-amino-5-carboxyvaleramido)-4-carboxy-7-methoxy-3-cephem-3-ylmethyl]isothiourea, N-propyl-S-[7β-(D-5-amino-5-carboxyvaleramido)-4-carboxy-7-methoxy-3-cephem-3-ylmethyl]-isothiourea, N,N-dimethyl-S-[7β-(D-5-amino-5-carboxyvaleramido)-4-carboxy-7-methoxy-3-cephem-3-ylmethyl)isothiourea, N,N-diethyl-S-[7β-(D-5-amino-5-carboxyvaleramido)-4-carboxy-7-methoxy-3-ylmethyl]isothiourea and N,N-dipropyl-S-[7β-(D-5-amino-5-carboxyvaleramido)-4-carboxy-7-methoxy-3-cephem-3-ylmethyl]isothiourea.

EXAMPLE 66

7β-(D-5-Amino-5-Carboxyvaleramido)-3-(Ethylthiomethyl)-7-Methoxy-3-Cephem-4-Carboxylic Acid A mixture of 7β-(D-5-amino-5-carboxyvaleramido)-3-(acetoxymethyl)-7-methoxy-3-cephem-4-carboxylic acid (0.654 g.) and ethanethiol (0.37 ml.) in a mixture of one part acetone and one part water (10 ml.) is stirred at room temperature and a 10% sodium hydroxide solution (2.0 ml.) is added with stirring. The mixture is then heated in a sealed tube for 100 hours and the resulting mixture is concentrated in vacuo. The residue is dissolved in water and fractionated through a polystyrene trimethylbenzylammonium anion exchange resin (43% H$_2$O). Selected fractions are combined and lyophilized to afford 7β-(D-5-amino-5-carboxyvaleramido)-3-(ethylthiomethyl)-7-methoxy-3-cephem-4-carboxylic acid.

Upon substituting an equivalent amount of methanethiol, propanethiol, pyridine-2-thiol, pyridine-3-thiol, pyridine-4-thiol, benzothiazole-2-thiol, 4-methylpyrimidine-2-thiol and 2-methyl-3,4-thiadiazole-5-thiol for the ethanethiol recited in the foregoing process and otherwise following the procedure described therein, there is thus obtained 7β-(D-5-carboxyvaleramido)-3-(methylthiomethyl)-7-methoxy-3-cephem-4-carboxylic acid, 7β-(D-5-amino-5-carboxyvaleramido)-3-(propylthiomethyl)-7-methoxy-3-cephem-4-carboxylic acid, 7β-(D-5-amino-5-carboxyvaleramido)-3-(2- pyridylthiomethyl)-7-methoxy-3-cephem-4-carboxylic acid, 7β-(D-5-amino-5-carboxyvaleramido)-3-(3-pyridylthiomethyl)-7-methoxy-3-cephem-4-carboxylic acid, 7β-(D-5-amino-5-carboxyvaleramido)-3-(4-pyridylthiomethyl)-7-methoxy-3-cephem-4-carboxylic acid, 7β-(D-5-amino-5-carboxyvaleramido)-3-(2-benzothiazolylthiomethyl)-7-methoxy-3-cephem-4-carboxylic acid, 7β-(D-5-amino carboxyvaleramido)-3-(4-methylpyrimidin-2-ylthiomethyl)-7-methoxy-3-cephem-4-carboxylic acid and 7β-(D-5-amino-5-carboxyvaleramido)-3-(2-methyl-3,4-thiadiazol-5-ylthiomethyl)-7-methoxy-3-cephem-4-carboxylic acid.

EXAMPLE 67

S-[7β-(D-5-Amino-5-Carboxyvaleramido)-4-Carboxy-7-Methoxy-3-Cephem-3-ylmethyl]N,N-Dimethyldithiocarbamate A solution of 7β-(D-5-amino-5-carboxyvaleramido)-3-(acetoxymethyl)-7-methoxy-3-cephem-4-carboxylic acid (6.82 g.) and sodium N,N-dimethyldithiocarbamate (2.86 g.) in 60 ml. of water is heated to 50° C. for 24 hours. The product is lyophilized and then fractionated through a polystyrene trimethylbenzylammonium anion exchange resin (43% H₂O). Selected fractions are then lyophilized to afford S-[7β-(D-5-amino-5-carboxyvaleramido)-4-carboxy-7-methoxy-3-cephem-3-ylmethyl]-N,N-dimethyldithiocarbamate.

Upon substituting an equivalent amount of the following reactants: sodium N-methyldithiocarbamate, sodium N,N-diethyl-dithiocarbamate, sodium N,N-di-n-propyldithiocarbamate, sodium N-methyl-N-(2-dimethylaminoethyl)dithiocarbamate, sodium N-ethyl-N-(2-diethylaminoethyl)dithiocarbamate, sodium N-(2-di-n-propylaminoethyl)dithiocarbamate, sodium N-methyl-N-(2-morpholinoethyl)eithiocarbamate, sodium N-methyl-N-(3-diethylaminopropyl)dithiocarbamate, sodium N-phenyl-N-(2-methylaminoethyl)dithiocarbamate, sodium N,N-tetramethylenedithiocarbamate, sodium N,N-pentamethylene-dithiocarbamate, sodium N,N-bis-(2-hydroxyethyl)dithiocarbamate and the sodium salt of 4-methyl-piperazinodithiocarboxylate for the sodium dimethyldithiocarbamate recited in the foregoing process, omitting the sodium bicarbonate, but otherwise following the procedure described therein, there is thus obtained S-[7β-(D-5-amino-5-carboxyvaleramido)-4-carboxy-7-methoxy-3-cephem-4-ylmethyl)-N-methyldithiocarbamate, S-[7β-(D-5-amino-5-carboxyvaleramido)-4-carboxy-7-methoxy-3-cephem-3-ylmethyl)-N,N-diethyldithiocarbamate, S-[7β-(D-5-amino-5-carboxyvaleramido)-4-carboxy-7-methoxy-3-cephem-3-ylmethyl]-N,N-di-n-propyldithiocarbamate, S-[7β-(D-5-amino-5-carboxyvaleramido)-4-carboxy-7-methoxy-3-cephem-3-ylmethyl)-N-methyl-N-(2-dimethylaminoethyldithiocarbamate, S-[7β-(D-5-amino-5-carboxyvaleramido)-4-carboxy-7-methoxy-3-cephem-3-ylmethyl]-N-ethyl-N-(2-diethylaminoethyl)dithiocarbamate, S-[7β-(D-5-amino-5-carboxyvaleramido)-4-carboxy-7-methoxy-3-cephem-3-ylmethyl]-N-(2-di-n-propylaminoethyl)dithiocarbamate, S-[7β-(D-5-amino-5-carboxyvaleramido)-4-carboxy-7-methoxy-3-cephem-3-ylmethyl]-N-methyl-N-(2-(-morphollnoethyl)dithiocarbamate, S-[7β-(D-5-amino-5-carboxyvaleramido)-4-carboxy-7-methoxy-3-cephem-3-ylmethyl]-N-methyl-N-(3-diethylaminopropyl)dithiocarbamate, S-[7β-(D-5-amino-5-carboxyvaleramido)-4-carboxy-7-methoxy-3-cephem-3-ylmethyl]-N-phenyl-N-(2-methylaminoethyl)dithiocarbamate, S-[7β-(D-5-amino-5-carboxyvaleramido)-4-carboxy-7-methoxy-3-cephem-3-ylmethyl]-N,N-tetramethylenedithiocarbamate, S-[7β-(D-5-amino-5 -carboxyvaleramido)-4-carboxy-7-methoxy-3-cephem-3-ylmethyl]-N,N-pentamethylenedithiocarbamate, S-[7β-(D-5-amino-5-carboxyvaleramido)-4-carboxy-7-methoxy-3-cephem-3-ylmethyl]-N,N-bis-(2-hydroxyethyl)dithiocarbamate and S-[7β-(D-5-amino-5-carboxyvaleramido)-4-carboxy-7-methoxy-3-cephem-3-ylmethyl]-4-methyl-piperazinodithiocarboxylate.

EXAMPLE 68

7β-(D-5-Amino-5-Carboxyvaleramido)-3-(Benzoylthiomethyl)-7-Methoxy-3-Cephem-4-Carboxylic Acid A mixture of 7β-(D-5-amino-5-carboxyvaleramido)-3-(acetoxymethyl)-7-methoxy-3-cephem-4-carboxylic acid (0.654 g.), sodium bicarbonate (0.504 g.) and thiobenzoic acid (0.414 g.) in 5.0 ml. of water is heated at 50° C. overnight under a nitrogen atmosphere. The product is precipitated by the addition of acetone and crystallized from a mixture of alcohol and water to afford 7β-(D-5-amino-5-carboxyvaleramido)-3-(benzoylthiomethyl)-7-methoxy-3-cephem-4-carboxylic acid.

Upon substituting an equivalent amount of potassium ethyl xanthate, potassium n-propyl xanthate, potassium isopropyl xanthate, potassium n-butyl xanthate, potassium n-hexyl xanthate, potassium cyclopentyl xanthate and potassium cyclohexyl xanthate for the thiobenzoic acid recited in the foregong process and otherwise following the procedure described therein, there is thus obtained 7β-(D-5-amino-5-carboxyvaleramido)-3-(ethoxythiocarbonylthiomethyl)-7-methoxy-3cephem-4-carboxylic acid, 7β-(D-5-amino-5-carboxyvaleramido)-3-(n-propoxythiocarbonylthiomethyl)-7-methoxy-3-cephem-4-carboxylic acid, 7β-(D-5-amino-5-carboxyvaleramido)-3-(isopropoxythiocarbonylthiomethyl)-7-methoxy-3-cephem-4-carboxylic acid, 7β(D-5-amino-5-carboxyvaleramido)-3-(n-butoxythiocarbonylthiomethyl)-7-methoxy-3-cephem-4-carboxylic acid, 7β(D-5-amino-5-carboxyvaleramido)-3-(n-hexyloxythiocarbonylthiomethyl)-7-methoxy-3-cephem-4-carboxylic acid, 7β-(D-5-amino-5-carboxyvaleramido)-3-(cyclopentyloxythiocarbonylthiomethyl)-7methyoxy-3-cephem-4-carboxylic acid and 7β-(D-5-amino-5-carboxyvaleramido)-3-(cyclohexyloxythiocarbonylthiomethyl)-7-methoxy-3-cephem-4-carboxylic acid.

EXAMPLE 69

7β-(D-5-Amino-5-Carboxyvaleramido)-3-(Toluene-p-Sulfonylmethyl)-7-Methoxy-3-Cephem-4-Carboxylic Acid A mixture of 7β-(D-5-amino-5-carboxyvaleramido)-3-(acetoxymethyl)-7-methoxy-3-cephem-4-carboxylic acid (0.654 g.) and sodium toluene-p-sulfinate (1.0 g.) in 5.0 ml. of water is heated at 50° C. for 24 hours. The mixture is concentrated in vacuo and crystallized from a mixture of methanol and water to afford 7β-(D-5-amino-5-carboxyvaleramido)-3-(toluene-p-sulfonylmethyl)-7-methoxy-3-cephem-4-carboxylic acid.

A mixture of 7β-(D-5-amino-5-carboxyvaleramido)-3-(acetoxymethyl)-7-methoxy-3-cephem-4-carboxylic acid (2.0 g.) and sodium azide (1.0 g.) are dissolved in 10 ml. water and heated at 50° C. overnight. The mixture is then lyophilized to afford crude 7β-(D-5-amino- 5-carboxyvaleramido)-3-(azidomethyl)-7-methoxy-3-cephem-4-carboxylic acid.

Alternatively, in lieu of treating 7β-(D-5-amino-5-carboxyvaleramido)-3-(acetoxymethyl)-7-methoxy-3-cephem-4-carboxylic acid with sodium azide, it is possible to substitute 842A per se therefor in an otherwise analogous process to afford an identical product. The following example illustrates this method of preparation:

7β-(D-5-Amino-5-carboxyvaleramido)-3-(carbamoyloxymethyl)-7-methoxy-3-cephem-4-carboxylic acid (100 mg.) in a 0.5 M phosphate buffer solution (5 ml., obtained by adding 3.5 g. of sodium dihydrogen phosphate and 3.4 g. of disodium phosphate in 100 ml. of water followed by the addition of sufficient hydrochloric acid to bring the pH to 5) was heated in the presence of sodium azide (20 mg.) at 95° C. for eight minutes. Preparative thin layer chromatography gave 20 mg. of 7β-(D-5-amino-5-carboxyvaleramido)-3-(azidomethyl)-7-methoxy-3-cephem-4-carboxylic acid as indicated by infra-red and nuclear magnetic resonance identification. This material possessed bioactivity against several strains of bacteria. This product was characterized by the following data:

Thin Layer Chromatography: conducted on cellulose plates in a 75% aqueous acetonitrile solvent; the Rf value for this product was 0.7; the Rf for the disodium salt of 842A was 0.3.

Ultra-Violet: the λ maximum was 263 millimicrons (i.e., mµ); the Molecular Extinction Coefficient was approximately 3400 (theoretical: 8000); Infra-red in Nujol was 1780 cm$^{-1}$ indicating the presence of a β-lactam ring; also, the product gave a positive ninhydrin test indicating the presence of an α-aminoadipoyl side chain.

Bioassay: the disc zone sizes in the following table are expressed in mm. for 100γ/ml of antibiotic.

monium anion exchange resin (43% H$_2$O) and selected fractions are combined and lyophilized to afford 7β-(D-5-phthaloylamino-5-carboxyvaleramido)-3-(aminomethyl)-7-methoxy-3-cephem-4-carboxylic acid. This product is then subjected to the deblocking procedure described in Example 14, Step G, via treatment with hydrazine hydrate and extraction with ethyl acetate to afford 7β-(D-5-amino-5-carboxyvaleramido)-3-(aminomethyl)-7-methoxy-3-cephem-4-carboxylic acid.

Acylation of the 7β-(D-5-phthaloylamino-5-carboxyvaleramido)-3-(aminomethyl)-7-methoxy-3-cephem-4-carboxylic acid with acetyl halide, propionyl halide and 2-phenylacetyl halide according to the method described above, followed by deblocking, yields the corresponding N-acylated derivatives: 7β-(D-5-amino-5-carboxyvaleramido)-3-(acetamidomethyl)-7-methoxy-3-cephem-4-carboxylic acid, 7β-(D-5-amino-5-carboxyvaleramido)-3-(propioamidomethyl)-7-methoxy-3-cephem-4-carboxylic acid and 7β-(D-5-amino-5-carboxyvaleramido)-3-(2-phenylacetamidomethyl)-7-methoxy-3-cephem-4-carboxylic acid.

Alternatively, in lieu of the catalytic process recited above 7β-(D-5-amino-5-carboxyvaleramido)-3-(azidomethyl)-7-methoxy-3-cephem-4-carboxylic acid may also be reduced to the corresponding amine via molecular hydrogenation. The following example illustrates this method of preparation.

7β-(D-5-Amino-5-carboxyvaleramido)-3-(azidomethyl)-7-methoxy-3-cephem-4-carboxylic acid was dissolved in a solution of 90% acetic acid and 10% water. The mixture was cooled to 0°–5° C. and zinc dust (30 mg.) was added. After 10 minutes the mixture was filtered and treated with hydrogen sulfide to remove soluble zinc. The resulting mixture was then diluted with a large volume of water and lyophilized to afford

| Organism | Disodium Salt of 842A (100γ/ml) | 7β-(D-5-amino-5-carboxyvaleramido)-3-(azidomethyl)-7-methoxy-3-cephem-4-carboxylic acid |
|---|---|---|
| Escherichia coli W-MB-60 | 18 | 21 (100γ/ml) |
| Pseudomonas stutzeri MB-1231 | 22 | 20 (100γ/ml) |
| Vibrio percolans MB-1272 | 18 | 16 (5γ/ml) |

EXAMPLE 71

7β-(D-5-Amino-5-Carboxyvaleramido)-3-(Aminomethyl)-7-Methoxy-3-Cephem-4-Carboxylic Acid The crude sample of 7β-(D-5-amino-5-carboxyvaleramido)-3-(azidomethyl)-7-methoxy-3-cephem-4-carboxylic acid obtained in Example 70 is blocked according to the method described in Example 14, Step A and the 7β-(D-5-phthaloylamino-5-carboxyvaleramido)-3-(azidomethyl)-7-methoxy-3-cephem-4-carboxylic acid thus obtained is then hydrogenated over platinum oxide in an aqueous methanol solution containing acetic acid. The catalyst is filtered and the solution concentrated. A solution of the residue is then fractionated through a polystyrene trimethylbenzylamsubstantially pure 7β-(D-5-amino-5-carboxyvaleramido)-3-(aminomethyl)-7-methoxy-3-cephem-4-carboxylic acid. This product was characterized by the following data:

Thin Layer Chromatography: conducted on cellulose plates in a 75% aqueous acetonitrile solvent; the Rf value for this product was 0.2; the Rf for the disodium salt of 842A was 0.3.

Ultra-Violet: the λ maximum was 263 mµ; the Molecular Extinction Coefficient was approximately 3500 (theoretical: 8000); Infra-red in Nujol was 1780cm$^{-1}$ indicating the presence of a β-lactam ring; also, the product gave a positive ninhydrin test indicating the presence of an γ-aminoadipoyl side chain.

Bioassay: the disc zone sizes in the following table are expressed in mm. for equal concentrations of antibiotic.

| Organism | Disodium Salt of 842A (100γ/ml) | 7β-(D-5-amino-5-carboxy-valeramido)-3-(aminomethyl)-7-methoxy-3-cephem-4-carboxylic acid |
|---|---|---|
| *Vibrio* percolans MB-1272 | 18 | 20 (5γ/ml) |
| *Salmonella* gallinarum MB-1272 | 27 | 21 (100γ/ml) |
| *Pseudomonas* stutzeri MB-1231 | 21 | 21 (100γ/ml) |

EXAMPLE 72

7β-(D-5-Amino-5-Carboxyvaleramido)-3-(2,4-Dihydroxyybenzyl-7-Methoxy-3-Cephem-4-Carboxylic Acid A mixture of 7β-(D-5-amino-5-carboxyvaleramido)-3-(acetoxymethyl)-7-methoxy-3-cephem-4-carboxylic acid (0.654 g.), resorcinol (1.1 g.) and water 10 ml.) are heated at 50° C. for two days. The reaction mixture is then lyophilized to afford crude 7β-(D-5-amino-5-carboxyvaleramido)-3-(2,4-di-hydroxybenzyl)-7-methoxy-3-cephem-4-carboxylic acid.

EXAMPLE 73

7β-(D-5-Amino-5-Carboxyvaleramido)-3-(N-Methylindol-3-yl-Methyl)-7-Methoxy-3-Cephem-4-Carboxylic Acid A solution of N-methylindole (0.655 g.) in acetone (5 ml.) is added to a solution of 7β-(D-5-amino-5-carboxyvaleramido)-3-(acetoxymethyl)-7-methoxy-3-cephem-4-carboxylic acid (0.654 g.) in water (5 ml.) at 50° C. The mixture is heated for 48 hours and the solvent is then removed in vacuo and the residue triturated with ether to afford crude 7β-(D-5-amino-5-carboxyvaleramido)-3-(N-methylindol-3-ylmethyl)-7-methoxy-3-cephem-4-carboxylic acid.

EXAMPLE 74

Monosodium Salt of 7β-(D-5-Amino-5-Carboxyvaleramido)-3-(Hydroxymethyl)-7-Methoxy-3-Cephem-4-Carboxylic Acid Step A: Dibenzyl Ester of 7β-(D-5-Phthaloylamino-5-Carboxyvaleramido)-3-(Carbamoyloxymethyl)-7-Methoxy-3-Cephem-4-Carboxylic Acid A solution of 7β-(D-5-phthaloylamino-5-carboxyvaleramido)-3-(carbamoyloxymethyl)-7-methoxy-3-cephem-4-carboxylic acid (0.653 mg.) (Example 14, Step A) in methanol is treated with a slight excess of freshly prepared phenyldiazomethane. After standing overnight at room temperature the solution is evaporated to afford 1.053 g. of residue identified as the dibenzyl ester of 7β-(D-5-phthaloylamino-5carboxyvaleramido)-3-(carbamoyloxymethyl)-7-methoxy-3-cephem-4-carboxylic acid.

Step B: Dibenzyl Ester of 7β-(D-5-Phthaloylamino-5-Carboxyvaleramido)-3-(Hydroxymethyl)-7-Methoxy-3-Cephem-4-Carboxylic Acid The dibenzyl ester of 7β-(D-5-phthaloylamino-5-carboxyvaleramido)-3-(carbamoyloxymethyl)-7-methoxy-3-cephem-4-carboxylic acid (0.5 g.) obtained in Step A is dissolved in purified dioxane (5 ml.) containing 1.5 equivalents of pyridine. A solution of nitrosylchloride (1.3 equivalents) in methyl chloride is added and the solution stirred in an ice bath for one hour. The product thus obtained is a solution of the dibenzyl ester of 7β-(D-5-phthaloylamino-5-carboxyvaleramido)-3-(hydroxymethyl)-7-methoxy-3-cephem-4-carboxylic acid which is used directly in the following step.

Step C: Disodium Salt of 7β-(D-5-Phthaloylamino-5-Carboxyvaleramido)-3-(Hydroxymethyl)-7-Methoxy-3-Cephem-4-Carboxylic Acid A solution of 10% palladium (0.5 g.) on carbon is added, together with 0.5 ml. of glacial acetic acid, to the dibenzyl ester of 7β-(D-5-phthaloylamino-5-carboxyvaleramido)-3-(hydroxymethyl)-7-methoxy-3-cephem-4-carboxylic acid obtained in Step B. The mixture is hydrogenated at 40 lb. per square inch with agitation for two hours; the catalyst is removed by filtration through diatomaceous earth and the solvent removed by concentration in vacuo. The residue is dissolved in methylene chloride and the solution extracted with a 5% sodium bicarbonate solution. The resulting mixture is then acidified to pH 2 with sulfuric acid and extracted with ethyl acetate. Upon drying the extract is concentrated in vacuo to afford a residue identified as 7β-(D-5-phthaloylamino-5-carboxyvaleramido)-3-(hydroxymethyl)-7-methoxy-3-cephem-4-carboxylic acid. This product is then dissolved in water containing two equivalents of sodium bicarbonate and lyophilized to give the disodium salt of 7β-(D-5-phthaloylamino-5-carboxyvaleramido)-3-(hydroxymethyl)-7-methoxy-3-cephem-4-carboxylic acid.

Step D: Monosodium Salt of 7β-(D-5-Amino-5-Carboxyvaleramido)-3-(Hydroxymethyl)-7-Methoxy-3-Cephem-4-Carboxylic Acid The disodium salt of 7β-(D-5-phthaloylamino-5-carboxyvaleramido)-3-(hydroxymethyl)-7-methoxy-3-cephem-4-carboxylic acid obtained in Step F is dissolved in water. One equivalent of hydrazine hydrate is then added and the mixture is allowed to stand at room temperature overnight. The aqueous solution is extracted with ethyl acetate and the aqueous phase is acidified to pH 8.0 with dilute hydrochloric acid and lyophilized to afford the monosodium salt of 7β-(D-5-amino-5-carboxyvaleramido)-3-(hydroxymethyl)-7-methoxy-3-cephem-4-carboxylic acid. This product was characterized by the following data:

Ultra-Violet: the λH₂O maximum was 240 and 263 mμ; Infra-red in Nujol was 5.69μ indicating the presence of a β-lactam ring.

Electrophoresis: the product was streaked on the center line of 10 × 40 cm. Camag S & S 2040-B paper and ionized at 2,000 volts for 50 minutes in the following buffers. Visualization was by ultra-violet and/or ninhydrin. The product traveled the following distance (cm. to front of spot) from origin (+ means toward anode, − means toward cathode):

| pH 6.2; 0.1M to acetate lutidine—acetate | pH 4.0; 0.1M to acetate pyridine—acetate | pH 2.3 10% acetic acid |
| --- | --- | --- |
| +11 | +13 | −1.5. |

The positive ninhydrin test indicates the presence of an α-aminoadipoyl side chain.

Paper Chromatography: on circular Whatman 1 paper. Spots visualized by ultra-violet and ninhydrin in the following solvents:

a. 4 parts n-butanol, 1 part acetic acid, 1 part methanol and 2 parts water; $R_f$: 0.52.

b. 1 part n-propanol, 1 part water and 1 part acetonitrile; $R_f$: 0.50.

Proton Magnetic Resonance: the proton magnetic resonance (pmr) spectrum for the moieties shows the following absorbences:

| Proton Magnetic Resonance $D_2O(\tau)$ | | | | | | |
| --- | --- | --- | --- | --- | --- | --- |
| $CH_2CH_2(m)$ | $CH_2CO(m)$ | $2-CH_2(m)$ | $OCH_3(s)$ | $CH(m)$ | $3'-CH_2(s)$ | $6-H(s)$ |
| 8.4–7.9 | 7.7–7.3 | 6.7–6.3 | 6.47 | 6.3–6.1 | 5.77 | 4.83 |

(s) indicates singlet
(m) indicates multiplet

EXAMPLE 75

Purification; Monosodium Salt of 7β-(D-5-Amino-5-Carboxyvaleramido)-3-(Carbamoyloxymethyl)-7-Methoxy-3-Cephem-4-Carboxylic Acid The monosodium salt of 7β-(D-5-amino-5-carboxyvaleramido)-3-(carbamoyloxymethyl)-7-methoxy-3-cephem-4-carboxylic acid (1.0 g.) prepared according to Example 12 was dissolved in 20 ml. of 1% aqueous n-butanol and chromatographed on a column containing 2,530 ml. of Sephadex G-10, a modified dextran gel in bead form. The column was developed with 1% aqueous n-butanol at 10 ml/minute and 10.5 ml. fractions were collected automatically. The effluent was monitored with a recording refractometer and the fractions were bioassayed. The bioactivity appeared in fractions 99 through 122 and these were pooled and concentrated to dryness to yield 670 mg. of product containing primarily the monosodium salt of 7β-(D-5-amino-5carboxyvaleramido)3-(carbamoyloxymethyl)-7-methoxy-3-cephem-4-carboxylic acid.

The column was subsequently calibrated by chromatography on a mixture of Blue Dextran 2000 and sodium chloride under identical conditions. Blue Dextran 2000 was detected in fractions 85 through 93 and sodium chloride was detected in fractions 140 through 155, thus indicating that the bioactive product can be separated from impurities of this nature.

EXAMPLE 76

7β-(D-5-Amino-5-Carboxyvaleramido)-3-Methyl-7-Methoxy-3-Cephem-4-Carboxylic Acid A 10% palladium on charcoal catalyst was suspended in water (80 ml.) and treated with hydrogen. The catalyst was then filtered and suspended again in water (50 ml.) and to this mixture (2.67 g.) was added the sodium salt of 842A (1.0 g.) in water (10 ml.). The resulting mixture was shaken for 22 hours at room temperature in an hydrogen atmosphere.

The catalyst was removed by filtration was washed once with water (50 ml.). The combined wash and filtrate was then concentrated to dryness to afford a 52.8% yield of 7β-(D-5-amino-5-carboxyvaleramido)-3-methyl-7-methoxy-3-cephem-4-carboxylic acid (528 mg.).

The 7β-(D-5-amino-5-carboxyvaleramido)-3-methyl-7-methoxy-3-cephem-4-carboxylic acid thus obtained was compared with starting material using thin layer chromatography. Silica-gel plates were used with the upper phase consisting of 4 parts n-butyl alcohol, one part acetic acid and 4 parts water. The hydrogenolysis product exhibited two spots with a higher rate of flow (Rf) than the starting material. The spots were detected by ninhydrin and ultra-violet fluorescence. The following table lists the observed differences as between the sodium salt of 842A and the 7β-(D-5-carboxyvaleramido)-3-methyl-7-methoxy-3-cephem-4-carboxylic acid product.

| Measurement | Sodium Salt of 842A | 7β-(D-5-amino-5-carboxyvaleramido)-3-methyl-7-methoxy-3-cephem-4-carboxylic acid |
| --- | --- | --- |
| Bioactivity | 5 μg/ml gave a 25 mm zone against *Vibrio percolans* (MB-1272) | Inactive at 50 μg/ml (<2% of initial activity) |
| Thin Layer Chromatography ~15 μg/spot | Rf 0.1 ninhydrin (positive) ultra violet (positive) | Rf 0.25 ninhydrin (positive) ultra violet (positive) RF 0.35 ninhydrin (positive) ultra violet (negative) |
| Ultra Violet | λ maximum 266 nm $E^{1\%}_{1cm}$ 142 | λ maximum 265 nm $E^{1\%}_{1cm}$ 100 |

EXAMPLE 77

S-[7β-(D-5-Amino-5-Carboxyvaleramido)-4-Carboxy-7-Methoxy-3-Cephem-3-yl-Methyl]Thiouronium Antibiotic 842A (100 mg.) was heated for eight minutes with thiourea (26 mg.) at 95° C. in a 0.5 M phosphate buffer solution (5 ml.; obtained by adding 3.5 g. of sodium dihydrogen phosphate and 3.4 g. of disodium phosphate in 100 ml. of water followed by the addition of sufficient hydrochloric acid to bring the pH to 5).

Electrophoresis of the solution at pH 7 showed the thiouronium compound as a non-mobile entity whereas 842A had an Rf of about 0.2. The mixture was purified by absorption on a polystyrene nuclear sulfonic acid cation exchange resin on the hydrogen cycle (Dowex 50) to remove the phosphate buffer. Elution was carried out using a 0.1N pyridine solution. The pH was adjusted to 8 with 1N sodium hydroxide and evaporated under vacuum to remove residual pyridine. Lyophilization gave a tan powder identified as S-[7β-(D-5-amino-carboxyvaleramido)-4-carboxy-7-methoxy-3-cephem-3-yl-methyl]thiouronium. This product was characterized by the following data:

Thin Layer Chromatography: conducted on cellulose plates in a 25% aqueous acetonitrile solvent; the Rf value for this product was 0.15; the Rf for the disodium salt of 842A was 0.3.

Ultra-Violet: the λ maximum was 263 mμ; the Molecular Extinction Coefficient was approximately 5,700 (theoretical: 8,000); Infra-red in nujol was 1,780cm$^{-1}$ indicating the presence of a β-lactam ring; also, the product gave a positive ninhydrin test indicating the presence of an α-aminoadipoyl side chain.

Electrophoresis: the introduction of a positive charge into the product was confirmed by electrophoresis at 1,000 volts using 0.05 M phosphate buffer at pH 7; the Rf for the product was 0.01; the Rf for the disodium salt of 842A was 0.4.

Bioassay: The disc zone sizes in the following table are expressed in mm. for equal concentrations of antibiotic.

carded. One-half volume of ethyl acetate was added and the aqueous layer was adjusted to pH 2.5 with concentrated hydrochloric acid in an ice bath to maintain the temperature below 5° C. After separation of the ethyl acetate the aqueous solution was extracted twice more with one-half volumes of ethyl acetate at pH 2.5. Based on ultra-violet measurements 50% of the starting ultra-violet absorbent was in the extracts and 22% in the spent aqueous phase. The extracts were combined and concentrated to dryness to yield 645 mg. of 7β-(D-5N-tert-tertiary-butoxycarbonylamino-5-carboxyvaleramido)-3-(carbamoyloxymethyl)-7-methoxy-3-cephem-4-carboxylic acid having one-tenth the biopotency of the starting material.

Thin-layer chromatograms were run using Analtech silica gel G.F. plates and the upper phase of a 4:1:4 n-butanol, acetic acid, water system. The product had an Rf of 0.54 by ultra-violet detection and was ninhydrin negative. Starting material had an Rf of 0.1 and was ultra-violet and ninhydrin positive.

Removal of the tertiary-butoxycarbonyl protecting group from a 10 mg. sample of the 7β-(D-5N-tert-tertiary-butoxycarbonylamino-5-carboxyvaleramido)-3-(carbamoyloxymethyl)-7-methoxy-3-cephem-4-carboxylic was accomplished by dissolving the material in trifluoroacetic acid (0.2 ml.) and allowing the solution to stand at room temperature for five minutes. The solution was then concentrated to dryness at room temperature. Thin-layer chromatography as previously described gave a spot for this product with an Rf of 0.1 which was ultra-violet and ninhydrin positive.

| Organism | Disodium Salt of 842A (100γ/ml) | S-[7β-(D-5-amino-5-carboxy-valeramido)-3-carboxy-7-methoxy-3-cephem-3-yl-methyl]-thiouronium (100γ/ml) |
|---|---|---|
| *Vibrio percolans* B-1272 | >35 | 27 |
| *Salmonella gallinarum* MB-1287 | 27 | 23 |
| *Pseudomonas stutzeri* MB-1231 | 22 | 22 |
| *Proteus vulgaris* MB-838 | 27 | 17 |

EXAMPLE 78

7β-(D-5-Amino-5-Carboxyvaleramido)-3-(4-Methylthiazol-2-ylmercaptomethyl)-7-Methoxy-3-Cephem-4-Carboxylic Acid Step A: 7β-(D-5-11-Tertiary-Butoxycarbonylamino-5-Carboxyvaleramido)-3-(Carbamoyloxymethyl)-7-Methoxy-3-Cephem-4-Carboxylic Acid The disodium salt of 842A (1.0 g.) was dissolved in 5% di-basic potassium phosphate (31.6 ml.) and acetone (20.8 ml.) was added with stirring. The pH of the solution was then adjusted to 9.5 to 9.6 with sodium hydroxide and tertiary-butoxycarbonylazide (1.0 ml.) was added with stirring. Stirring was continued for 4–6 hours at room temperature while maintaining the pH between 9.0 and 9.6 via the addition of sodium hydroxide. The reaction mixture was then stirred overnight, by which time the pH had dropped to 8.5. The pH was readjusted to 9.6 with sodium hydroxide and stirring was continued for an additional three hours while maintaining the pH between 9.0 and 9.6.

The resulting mixture was then extracted with one-half volume of ethyl acetate and the extract was dis- Step B: 7β-(D-5-Amino-5-Carboxyvaleramido)-3-(4-Methylthiazol-2-ylmercaptomethyl)-7-Methoxy-3-Cephem-4-Carboxylic Acid 7β-(D-5N-Tert-Tertiary-butoxycarbonylamino-5-carboxyvaleramido)-3-(carbamoyloxymethyl)-7-methoxy-3-cephem-4-carboxylic acid (100 mg.) in 5 ml. of a pH 7 buffer (a 0.5 M solution of a mixture of 3.5 g. sodium dihydrogen phosphate 3.4 g. of disodium phosphate in 100 ml. of water) containing 2-mercapto-4-methylthiazole (50 mg.) is heated at 95° C. for 8 minutes. There is thus obtained 7β-(D-5-N-tertiary-butoxycarbonylamino-5-carboxyvaleramido)-3-(4-methylthiazol-2-ylmercaptomethyl)-7-methoxy-3-cephem-4-carboxylic acid which, upon treatment with trifluoroacetic acid (0.2 ml.), generates 7β-(D-5-amino-5-carboxyvaleramido)-3-(4-methylthiazol-2-ylmercaptomethyl)-7-methoxy-3-cephem-4-carboxylic acid. This product was characterized by the following data:

Thin Layer Chromatography: conducted on cellulose plates in a 25% aqueous acetonitrile solvent; the Rf value for this product was 0.6; the Rf for the disodium salt of 842A was 0.3.

Ultra-Violet: the λ maximum was 269 mμ; the Molecular Extinction Coefficient was approximately 2,000 (theoretical: 3,000); Infra-red in nujol was 1,780cm$^{-1}$ indicating the presence of a β-lactam ring; also, the product gave a positive ninhydrin test indicating the presence of an α-aminoadipoyl side chain.

Bioassay: The disc zone sizes in the following table are expressed in mm. for equal concentrations of antibiotic.

| Organism | Disodium Salt of 842A (100γ/ml) | 7β-(D-5-amino-5-carboxyvaleramido)-3-(4-methylthiazol-2-ylmercaptomethyl)-7-methoxy-3-cephem-4-carboxylic acid (100γ/ml) |
|---|---|---|
| *Pseudomonas stutzeri* MB-1231 | 22 | 13.5 |
| *Escherichia coli* W-MB-60 | 18 | 14 |
| *Vibrio percolans* MB-1272 | 23 | 20 |

EXAMPLE 79

7β-(D-5-Amino-5-Carboxyvaleramido)-3-(1,3-4-Thiadiazol-2-ylmercaptomethyl)-7-Methoxy-3-Cephem-4-Carboxylic Acid By substituting 2-mercapto-1,3-4-thiadiazole for the 2-mercapto-4-methylthiazole of Example 78, Step B, and otherwise following the procedure described therein there is thus obtained 7β-(D-5-amino-5-carboxyvaleramido)-3-(1,3,4-thiadiazol-2-ylmercaptomethyl)-7-methoxy-3-cephem-4-carboxylic acid.

EXAMPLE 80

7β-(D-5-Amino-5-Carboxyvaleramido)-3-(Thiocyanatomethyl)-7-Methoxy-3-Cephem-4-Carboxylic Acid Antibiotic 842A (100 mg.) was added to a 0.5 M buffer solution (5 ml.) consisting of 3.5 g. sodium dihydrogen phosphate and 3.4 g. disodium phosphate in 100 ml. of water and the pH of the mixture was brought to pH 5 by the addition of hydrochloric acid. Sodium thiocyanate (20 mg.) was added and the mixture was heated at 95° C. for 8 minutes. There is thus obtained 7β-(D-5-amino-5-carboxyvaleramido)-3-(thiocyanatomethyl)-7-methoxy-3-cephem-4-carboxylic acid.

EXAMPLE 81

7β-(D-5-Amino-5-Carboxyvaleramido)-3-(Chloromethyl)-7-Methoxy-3-Cephem-4-Carboxylic Acid Step A: Dibenzhydryl Ester of 7β-(D-5-N-Tertiary-Butoxycarbonylamino-5-Carboxyvaleramido)-3(Carbamoyloxymethyl)-7-Methoxy-3-Cephem-4-Carboxylic Acid To a solution of 7β-(D-5-N-tertiary-butoxycarbonylamino-5-carboxyvaleramido)-3-(carbamoyloxymethyl)-7-methoxy-3-cephem-4-carboxylic acid (15.0 g.) in ethyl acetate (500 ml.) is added diphenyldiazomethane (5.5 g.) in 70 ml. of ether. The mixture is warmed to 40° C. with stirring and then treated after 30 minutes with additional diphenyldiazomethane (5.5 g.) in ether (70 ml.). After 3 hours the solvent is removed in vacuo and replaced by a mixture of methanol (500 ml.) and water (20 ml.). The methanol-water solution is extracted four times with hexane and then evaporated in vacuo. The residue is dissolved in ethyl acetate, dried over sodium sulfate and evaporated in vacuo to afford the dibenzhydryl ester of 7β-(D-5-N-tertiary-butoxycarbonylamino-5-carboxyvaleramido)-3-(carbamoyloxymethyl)-7-methoxy-3-cephem-4-carboxylic acid.

Step B: Dibenzhydryl Ester of 7β-(D-5-N-Tertiary-Butoxycarbonylamino-5-Carboxyvaleramido)-3-(Chloromethyl)-7-Methoxy-3-Cephem-4-Carboxylic Acid The dibenzhydryl ester of 7β-(D-5-N-tertiary-butoxycarbonylamino-5-carboxyvaleramido)-3-(carbamoyloxymethyl)-7-methoxy-3-cephem-4-carboxylic acid (1 m. mole) is dissolved in methylene chloride (5 ml.) and the mixture is cooled to 0° C. Collidine (1 m. mole) is added followed by the dropwise addition of a solution of phosphorous pentachloride (0.6 m. mole) in methylene chloride (5 ml.). The mixture is then stirred for an hour in an ice bath at 0° C. and the resulting solution is extracted with sodium bicarbonate, dilute hydrochloric acid and a saturated solution of sodium chloride. The mixture is evaporated to dryness and then isolated by chromatography on a cooled silica gel column using chloroform as the eluant. The product thus obtained is the dibenzhydryl ester of 7β-(D-5-N-tertiary-butoxycarbonylamino-5-carboxyvaleramido)-3-(chloromethyl)-7-methoxy-3-cephem-4-carboxylic acid.

Step C: Trifluoroacetic Acid Salt of 7β-(D-5-Amino-5-Carboxyvaleramido)-3-(Chloromethyl)-7-Methoxy-3-Cephem-4-Carboxylic Acid A solution of dibenzhydryl ester of 7β-(D-5-N-tertiary-butoxycarbonylamino-5-carboxyvaleramido)-3(chloromethyl)-7-methoxy-3-cephem-4-carboxylic acid (1 m. mole) in anisole (13 ml.) is poured into 6.5 ml. of cold (0° C.) trifluoroacetic acid with stirring. After 5 minutes the solution is poured, with stirring, into an ether solution (1800 ml.) maintained at 0° C. The solid precipitate which results is then collected and dried to afford 7β-(D-5-amino-5-carboxyvaleramido)-3-(chloromethyl)-7-methoxy-3-cephem-4-carboxylic acid trifluoroacetate.

EXAMPLE 82

3-Hydroxymethyl-7β-(D-5-Amino-5-Carboxyvaleramido)-7-Methoxy-3-Cephem-4-Carboxylic Acid Lactone and Hydrochloride A solution of monosodium salt of 3-hydroxymethyl-7β-(D-5-amino-5-carboxyvaleramido)-7-methoxy-3-cephem-4-carboxylic acid (9.4 mg., 0.022 m Mol) in 1.0 N hydrochloric acid (0.22 ml.) was kept at room temperature for 20 minutes and then treated with sodium acetate trihydrate (34 mg., 0.25 m Mol) and 1 ml. of water. Lyophilization of the solution left 24.5 mg. of a white solid. The crude product was purified by preparative paper chromatography on Whatman 3 MM paper using an equal parts mixture by volume of 1:1:1 n-propanol, water and acetonitriie as developing solvent. The product band was visualized by ultraviolet light, cut out, and stirred with water to a pulp. Filtration of the mixture followed by lyophilization of the clear filtrate afforded 9.1 mg. of nearly pure 3-hydroxymethyl-7β-(D-5-amino-5-carboxyvaleramido)-7-methoxy-3-cephem-4-carboxylic acid lactone as a white powder.

A sample of monosodium salt of 3-hydroxymethyl-7β-(D-5-amino-5-carboxyvaleramido)-7-methoxy-3-cephem-4-carboxylic acid was dissolved in 0.25 N hydrochloric acid and kept at room temperature for 30 minutes. The reaction was monitored by ultraviolet spectroscopy which showed no further change after 30 minutes (λmax 263 mμ). The solution was lyophilized to give 3-hydroxymethyl-7β-(D-5-amino-5-carboxyvaleramido)-7-methoxy-3-cephem-4-carboxylic acid lactone hydrochloride.

The compound was characterized by the following data:

Ultra Violet: the λH$_2$O maximum was 263 mμ; Infrared in Nujol was 5.60μ and 5.71μ indicating the presence of a β-lactam ring and a lactone ring, respectively.

Electrophoresis: the product was streaked on the center line of 10 × 40 cm. Camag S and S 2040-B paper and ionized at 2,000 volts for 50 minutes in the following buffers. Visualization was by ultra-violet and/or ninhydrin. The product traveled the following distances (cm. to front of spot) from origin (+ means toward anode, − means toward cathode):

| pH 4.0; 0.1M to acetate pyridine—acetate | pH 2.3 10% acetic acid |
|---|---|
| 0 | −6.5 |

The positive ninhydrin test indicates the presence of an α-aminoadipoyl side chain.

Paper Chromatography: on circular Whatman 1 paper. Spots visualized by ultra-violet and ninhydrin in the following solvents:
  a. 4 parts n-butanol, 1 part acetic acid, 1 part methanol and 2 parts water; R$_f$ 0.55.
  b. 1 part n-propanol, 1 part water and 1 part acetonitrile; R$_f$ 0.73.

The novel compounds of this invention have been described as having the 5-amino-5-carboxyvaleramido radical in the beta configuration with respect to the cephem nucleus. While this is based upon information currently available and is believed to be correct, applicants do not wish to be bound by this designation of spatial configuration in the event later information proves this to be incorrect.

The following organisms referred to in this specification are on deposit in the Culture Collection of the American Type Culture Collection where they are available under the following ATCC designations:

| | |
|---|---|
| *Escherichia coli* W-MB-60 | ATCC 9637 |
| *Proteus vulgaris* MB-838 | ATCC 21100 |
| *Alcaligenes faecalis* MB-9 | ATCC 212 |
| *Alcaligenes viscosus* MB-12 | ATCC 337 |
| *Vibrio percolans* MB-1272 | ATCC 8461 |
| *Bacillus subtilis* MB-964 | ATCC 6633 |

Also, in this specification several of the materials employed are referred to by trade name. These have the following composition and are available from the following suppliers:

1. Amber Yeast No. 300: a fraction of autolyzed brewers yeast; Amber Laboratories, Juneau, Wis.
2. Mobil par-S: an oil base defoamer (composition unknown); Mobil Oil Company, 150 E. 42nd Street, New York, N.Y.
3. Polyglycol 2000: a defoamer; polypropylene glycol polymer having an average molecular weight of 2000; Dow Chemical Company, Midland, Mich.
4. Biogel P-2: a gel filtration medium; a spherical polyacrylamide cross-linked with methylene bis-acrylamide; Bio-rad Laboratories, Richmond, Calif.
5. Dowex 50: a polystyrene nuclear sulfonic acid cation exchange resin; Dow Chemical Company, Midland, Mich.
6. Analtech G.F. Plates: silica gel with calcium sulfate binder and a fluorescent indicator 250 micrometers in thickness; Analtech Inc., 100 South Justison Street, Wilmington, Del. 19801.
7. Whatman 1: qualitative, chromatographic paper having an average thickness of 0.005 inches and an approximate ash weight of 0.0005 mg. per 11 cm. circle; W. and R. Balston, LTD., Address: H. Reeve Angel & Co., Inc., 52 Duane Street, New York 7, N.Y.
8. Whatman 3 MM: chromatographic paper having a medium flow rate with a capacity twice that of Whatman 1; approximate ash weight of 0.0009 mg. per 11 cm. circle; W. and R. Balston, LTD., Address: H. Reeve Angel & Co., Inc., 52 Duane Street, New York 7, N.Y.
9. Camag S and S 2040-B: chromatographic paper; Camag Inc., 11830 West Ripley Avenue, Milwaukee, Wis.

What is claimed is:

1. A compound according to the formula:

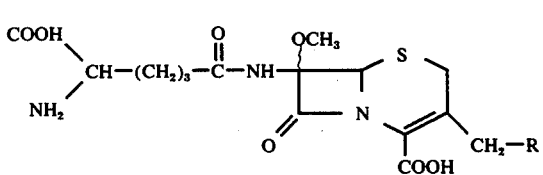

wherein R is hydroxy.

2. A compound according to the formula:

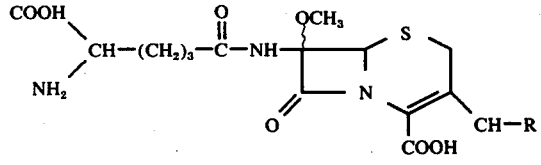

wherein R is hydroxy and pharmacologically acceptable salts.

* * * * *

UNITED STATES PATENT OFFICE
CERTIFICATE OF CORRECTION

Patent No. 4,017,487                      Dated April 12, 1977

Inventor(s) Edward O. Stapley et al.

It is certified that error appears in the above-identified patent and that said Letters Patent are hereby corrected as shown below:

Col. 26, Table VII, the title "Escherichia coli - Strain" should read ---Escherichia coli - Strain$^{xx}$---.
Col. 27, Table XI, the title "Escherichia coli - Strain" should read ---Escherichia coli - Strain$^{x}$---.
Col. 31, under "Medium IV:", the first line should read ---V8 Juice---.
Col. 31, under "Medium VI:", 4th line should read ---MgSO$_4$·7H$_2$O--
Col. 31, under "Medium VII:", 9th line should read ---FeSO$_4$·7H$_2$O---.
Col. 31, under "Medium VII:", 10th line should read ---ZnSO$_4$·7H$_2$O---.
Col. 41, line 37, the number "150" should read ---250---.
Col. 58, line 58, the number "VII" should read ---VIII---.
Col. 59, under "Medium IX:", 2nd line, "3%" should read ---2%---.
Col. 60, line 34, the number "17.25" should read ---27.25---.
Col. 60, line 35, the number "14.5" should read ---24.5---.

UNITED STATES PATENT OFFICE
CERTIFICATE OF CORRECTION

Patent No. 4,017,487     Dated April 12, 1977

Inventor(s) Edward C. Stanley et al

It is certified that error appears in the above-identified patent and that said Letters Patent are hereby corrected as shown below:

Col. 61, in the second tabulated table, the entire column second from the right under the heading "Eluate Fraction Dilution" should read as follows:
```
---1:10
   1:10
   1:5
   1:5
   1:5
   1:5
   1:5
   1:5---
```

Signed and Sealed this twenty-sixth Day of July 1977

[SEAL]

Attest:

RUTH C. MASON
*Attesting Officer*

C. MARSHALL DANN
*Commissioner of Patents and Trademarks*